US007531177B2

(12) United States Patent
Nascimento et al.

(10) Patent No.: US 7,531,177 B2
(45) Date of Patent: May 12, 2009

(54) SURFACE PROTEIN OF LEPTOSPIRA

(75) Inventors: Ana L. T. O. Nascimento, São Paulo (BR); Paulo L. Ho, São Paulo (BR); Elizabeth A. L. Martins, São Paulo (BR); Luciana C. C. Leite, São Paulo (BR); Marcia Gamberini, São Paulo (BR)

(73) Assignee: Fundacao de Amparo a Pesquisa do Estado se Sao Paulo, Sao Panlo (BR)

( * ) Notice: Subject to any disclaimer, the term of this patent is extended or adjusted under 35 U.S.C. 154(b) by 0 days.

(21) Appl. No.: 12/001,114

(22) Filed: Dec. 10, 2007

(65) Prior Publication Data

US 2009/0041796 A1    Feb. 12, 2009

Related U.S. Application Data

(62) Division of application No. 11/414,721, filed on Apr. 27, 2006, now Pat. No. 7,326,419, which is a division of application No. 11/264,728, filed on Nov. 1, 2005, now Pat. No. 7,108,853, which is a division of application No. 10/889,526, filed on Jul. 12, 2004, now Pat. No. 7,018,634, which is a division of application No. 10/376,397, filed on Feb. 28, 2003, now Pat. No. 6,852,322.

(60) Provisional application No. 60/360,566, filed on Feb. 28, 2002.

(51) Int. Cl.
*A61K 39/02* (2006.01)

(52) U.S. Cl. .............. 424/190.1; 424/130.1; 424/141.1; 424/150.1; 424/185.1; 424/234.1; 435/326; 435/331; 435/332; 435/340; 530/350; 530/387.1; 530/388.1

(58) Field of Classification Search ........................ None
See application file for complete search history.

(56) References Cited

U.S. PATENT DOCUMENTS 6,699,482 B2 *  3/2004  Haake et al. ............. 424/234.1

* cited by examiner

*Primary Examiner*—Jennifer E Graser
(74) *Attorney, Agent, or Firm*—Fulbright & Jaworski

(57) ABSTRACT

The invention relates to Leptospiral surface proteins, and the nucleic acid molecules which encode them. Various uses are described, including immunoprophylactic, diagnostic and therapeutic methods.

5 Claims, 11 Drawing Sheets

Figura 2

SURFACE PROTEIN OF LEPTOSPIRA

RELATED APPLICATION

Figure 1:
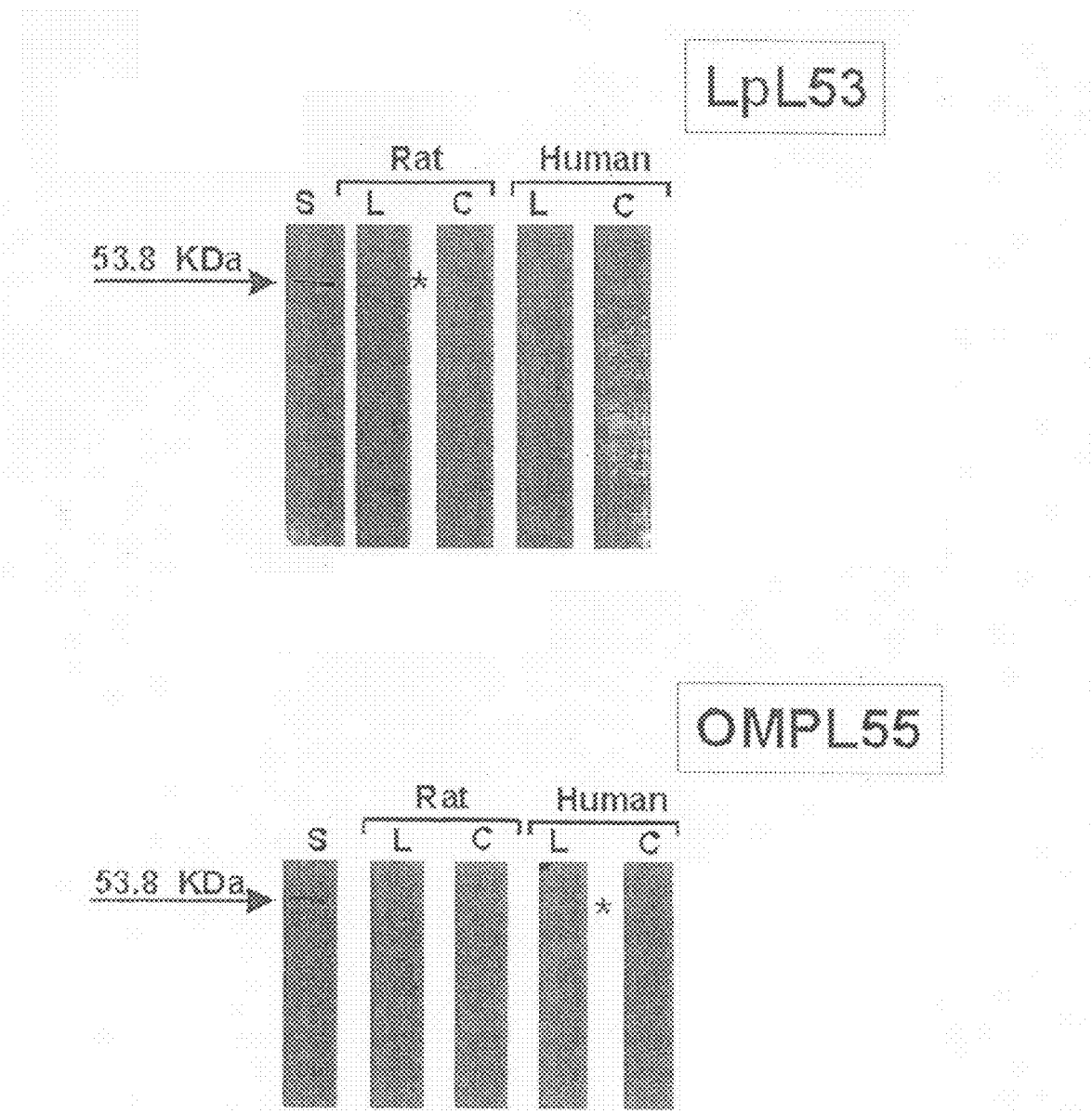

This application is a divisional of application Ser. No. 11/414,721, filed Apr. 27, 2006, now U.S. Pat. No. 7,326,419 which is a divisional application of application Ser. No. 11/264,728, filed Nov. 1, 2005, now U.S. Pat. No. 7,108,853, which is a divisional application of application Ser. No. 10/889,526 filed Jul. 12, 2004, now U.S. Pat. No. 7,018,634, which is a divisional application of application Ser. No. 10/376,397 filed Feb. 28, 2003, now U.S. Pat. No. 6,852,322, and claims priority of Application Ser. No. 60/360,566, filed Feb. 28, 2002, incorporated by reference in their entireties.

FIELD OF THE INVENTION

This invention relates to membrane associated proteins of *Leptospira* bacteria, *Leptospira Copenhageni* in particular. The proteins are useful both therapeutically, as, e.g., antisera, immunoprophylactically, as vaccines, as well as diagnostically. They can be used, for example, to detect antibodies in samples taken from subjects suspected of being infected, and also to generate antibodies which can then be used to detect the proteins, epitopic portions of the proteins, as well as the bacteria per se. Also a feature of the invention are nucleic acid molecules encoding these proteins, methods for purifying them, as well as various applications thereof.

BACKGROUND AND PRIOR ART

*Leptospira* is a genus of bacteria which is a member of the Spirochetes family. Other members of this family are *Borrelia* and *Treponema*. All three genuses are characterized by mobility, and a helical shape. All members of the family cause disease in animals, including humans, livestock, domesticated animals, and wild animals. For example, *Borrelia* is the causative agent for Lyme disease. Other diseases caused by Spirochetes include relapsing fever, syphilis and yaws.

*Leptospira* genus consists of a genetically diverse group of 12 species, eight of which are pathogenic, and four of which are non-pathogenic, and saprophytic. See Faine, et al. *Leptospira and Leptospirosis* ($2^{nd}$ edition, 1999, Melbourne, Australia, MediSci); Farr, *Clin. Infect. Dis* 21:1-8 (1995). Levett, *Clin. Microbiol. Rev.* 14:296-326 (2001), incorporated by reference. There are over 200 known pathogenic serovars of *Leptospira*. It is hypothesized that structural heterogeneity in lypopolysacchacide structure accounts for this. See, Levett, supra.

Leptospirosis, the disease caused by *Leptospira*, is zoonotic. Transmission to humans results from contact with domestic or wild animal reservoirs, or via contact with animal urine. Infected individuals show a wide spectrum of clinical manifestations in the early phases of the illness including fever, headache, chills and severe myalgia. In 5-15% of the clinical infections, severe multisystem complications result, including jaundice, renal failure and hemorrhaging. See Farr, supra, Faine, et al., supra. Severe leptospirosis has a mortality rate of 5-40%.

There is a large spectrum of animal species which serve as reservoirs for the bacteria. As a result, human leptospirosis is found throughout the world, and is considered to be the most widespread zoonotic disease. High risk groups include military personnel, farmers, miners, sewage and waste removal workers, veterinarians and abattoir workers. See, in this regard, Levett, supra, Faine, et al., supra. New patterns of transmission of the disease have emerged; however, emphasizing the public health issues associated with this disease. In "developed" countries outbreaks have been associated with recreational diseases, such as white water rafters in Costa Rica, and sporting events involving extensive outdoor activity, such as triathlons and "Eco-challenges." See, e.g., Levett, supra; Jackson, *Pediatr. Infect. Dis. J* 12:48-54 (1993); Center For Disease Control and Prevention: Outbreak of leptospirosis among white water rafters in Costa Rica (1997); Update: Leptospirosis and Unexplained Acute febrile illness among athletes participating in triathlons: Illinois and Wisconsin (1998). Update: Outbreak of Acute Illness Among Athletes Participating in Eco-Challenge—Sahah 2000—Borneo, Malaysia (2000). Underlying conditions associated with poverty have led to large, urban, epidemics of leptospirosis in Brazil and other countries, resulting in high mortality rates. See Lomor, et al., *Infect. Dis. Clin. North Am* 14:23-39 (2000); Ko, et al., *Lancet* 354:820-5 (1999).

Leptospirosis is a major issue in agriculture as well, due to its association with livestock and domestic animals. Among the manifestations of animal leptospirosis are spontaneous abortions, still births, infertility, failure to thrive, reduced milk production, and high fatality rates in diverse species such as cows, pigs, sheep, goats, horses and dogs. See Faine, et al., supra. Other manifestations of the disease are chronic infection, and shedding of pathogenic leptospires. Standard approaches to controlling this include international and national quarantines in the animal husbandry industry, with negative economic ramifications.

Clearly, there is a need to control leptospirosis; however, efforts have been hindered due to a lack of effective approaches. Long term survival of pathogenic leptospires in soil and water, as well as the abundance of animal reservoirs support long term survival of the pathogen so eradication is not a viable option. Hence, efforts have turned to approaches based upon vaccines.

Currently, available vaccines are based upon inactivated whole cell, or membrane preparations of pathogenic bacteria. These appear to induce protective responses via antibody induction. See Levett, supra, Faine, et al, supra. These vaccines do not produce long term protection against infection, and they do not confer cross protective immunity against serovars not included in the vaccines used. The number of serovars possible, and the cost of multicomponent serovar vaccines have thwarted development in this area.

A key mechanism in the pathogenesis of leptospirosis, as in other spirochetal diseases (such as Lyme disease and syphilis), is the ability of the pathogen to disseminate widely in the host during the early stage of infection. See Faine, et al., supra. It is presumed that surface associated leptospiral proteins, mediate interactions which facilitate entry and dissemination through host tissues. Virulence factors associated with the surface of the bacteria serve as vaccine candidates, in that any immune or other protective response would block dissemination in the host. Another important aspect of surface associated proteins is that they are, literally, "surface-associated," rendering them accessible to immune attack. Protective mechanisms associated with such surface associated proteins include antibody-dependent phagacytosis, and complement-mediated killing.

It would be desirable to have pure, or substantially pure *Leptospira* surface associated proteins available. Production of such proteins, in recombinant form, for example is cost effective, and provides a method to screen proteins to determine sub-unit or epitopic fragment based vaccines. Further, availability of recombinant proteins permits one to determine which proteins are conserved, especially among different pathogenic *Leptospira*, to determine which are the most suitable, cross-serovar vaccines.

There have been difficulties in identifying surface associated *Leptospira* proteins. using conventional biochemical and molecular biological methods. The genome of the spirochete *Borrelia burgdorferi* has been analyzed, and more than 100 surface associated lepoproteins were identified. The large size of the *Leptospira* genome (~4.6 Mb), and its complex life cycle suggest that a far greater number of surface associated proteins will be found. Using standard membrane extraction, isolation, and purification techniques, less than 10 *Leptospira* surface associated proteins have been identified and characterized. See Haake, et al., *Infect. Immun* 66:1579-1587 (1998); Haake et al., *Infect. Immun.* 6572-82 (1999); Haake, et al., *Infect. Immun* 68:2276-2285 (2000); Shang, et al., *Infect. Immun* 63:3174-3181 (1995); Shang, et al., *Infect. Immun* 64:2232-30 (1996). Also see U.S. Pat. Nos. 5,091, 301; 5,643,754; 5,638,757; 5,824,321; 6,140,083; 6,262,235; 6,306,623; and 6,308,641. All of these articles and patents are incorporated by reference. While Haake, et al., *Infect. Immun* 67:6572-82 (1999), describe immunization with recombinant protein L1pL41, OmpL1 and L1pL41 but, the response was not complete. None of these reference identify virulence associated proteins.

As has been pointed out, supra, the *Leptospira* genome is large. As a result, technical difficulties have prevented meaningful results in identifying surface associated proteins; however, the emerging field of bioinformatics has placed extremely powerful and valuable tools in the hands of those involved in Leptospiral research.

Via application of the techniques described supra, the inventors have discovered further *Leptospira* surface associated proteins useful in vaccine production, as well as in production of diagnostic kits for use in determining presence, onset, or decrease in Leptospiral infection. These, and other aspects of the invention will be clear from the disclosure which follows.

BRIEF DESCRIPTION OF THE FIGURES

FIGS. 1-11 inclusive, present data obtained from Western Blotting experiments, using the recombinant proteins of the invention. In all figures, control rat serum, and serum from rats that had been immunized with *Leptospira*, and control human sera as well as sera from patients diagnosed as suffering from Leptospirosis were used. FIG. 1 shows work done with the protein of SEQ ID NO: 2 & 4, FIG. 2 with SEQ ID NO: 6 & 8, and so forth.

FIG. 1 shows data from Western Blotting experiments using the proteins of SEQ ID NOS: 2 and 4.

FIG. 2 shows data from Western Blotting experiments using the proteins of SEQ ID NOS: 6 and 8.

FIG. 3 shows data from Western Blotting experiments using the proteins of SEQ ID NOS: 10 and 12.

FIG. 4 shows data from Western Blotting experiments using the proteins of SEQ ID NOS: 14 and 18.

FIG. 5 shows data from Western Blotting experiments using the proteins of SEQ ID NOS: 20 and 22.

FIG. 6 shows data from Western Blotting experiments using the proteins of SEQ ID NOS: 24 and 26.

FIG. 7 shows data from Western Blotting experiments using the proteins of SEQ ID NOS: 28 and 30.

FIG. 8 shows data from Western Blotting experiments using the proteins of SEQ ID NOS: 32 and 34.

FIG. 9 shows data from Western Blotting experiments using the proteins of SEQ ID NOS: 36 and 38.

FIG. 10 shows data from Western Blotting experiments using the proteins of SEQ ID NOS: 40 and 42.

FIG. 11 shows data from Western Blotting experiments using the proteins of SEQ ID NOS: 44 and 46.

DETAILED DESCRIPTION OF PREFERRED EMBODIMENTS

Example 1

A strain of *Leptospira*, referred to as "Fiocruz L1-30," was used. The strain was isolated from a patient with severe leptospirosis, contracted during an epidemic in 1996. See Ko, et al., *Lancet* 354:820-5 (1999), incorporated by reference. Leptospires were detected during dark field microscopy examination of a culture of tween-albumin media that had been inoculated with patient blood, following "Guidelines for the Control of Leptospirosis." WHO Offset Publ. (1982) incorporated by reference. The strain was identified as *Leptospira interrogans*, serovar *Copenhageni*, via biochemical and sera typing analysis. See Ko, et al., supra, Barocchi, et al., *J. Clin. Microbiol.* 39:191-195 (2001). A culture of the organism was then prepared in media with 10% glycerol, and stored at −70° C. Virulence capacity was determined by inoculating 28 day old weaning hamsters. Kidneys were removed from anesthetized animals, approximately 7 days after infection, macerated and were used to inoculate Tween-albumin media. Any cultures for which growth was detected were used to infect additional hamsters, as part of a second passage step. In all, three passage steps were performed. Isolates from the final passage were used to prepare large scale, two liter cultures, again in Tween albumin media. Following centrifugation (10, 000×g for 20 minutes), pellets were stored at −70° C., prior to use in DNA purification steps. The genomic DNA was extracted using standard methods, as set forth in, e.g., Sambrook and Maniatis, *Molecular Cloning: A Laboratory Manual* (2nd edition, Cold Spring Harbor, 1989).

Once the genomic DNA was isolated, it was partially digested with MboI, in order to generate fragments which ranged from 30 to 60 kilobase pairs. These were cloned into a cosmid vector "Lawrist 4," described by Hanke, et al., *Biotechniques* 21(4):686-8 and 690-3 (1996), incorporated by reference to produce a cosmid library. Any dephosphorylated DNA fragments were ligated to the cosmid vector, in the presence of T4 DNA ligase. The resulting, recombinant DNA was then packed into phage particles, using a commercially available product, and was then transfected into *E. coli* DH5*. Transfected cells were plated onto solid, Luria-Bertani medium supplemented with kanamycin, and were grown, overnight, at 37° C.

Following culture, the transfectants were used in a shotgun library construction protocol. To elaborate, genomic DNA was purified, in accordance with Fleischmann, et al., Science 269:496-512 (1995), incorporated by reference, and the purified DNA was sheared into fragments via nebulization.

The resulting fragments were repaired by end filling, using the Klenow fragment of *E. coli* DNA polymerase, or phage T7 DNA polymerase, or both, before ligation into the SmaI BAP site of pUC18. The resulting, recombinant DNA was transformed into *E. coli* DH10B cells, via electroporation. The transformants were plated, on Luria-Bertani agar medium containing ampicillin, and grown overnight at 37° C.

Single bacterial colonies resulting from the culture were inoculated in 96 well microtiter plates containing nutrient broth and ampicillin. These were grown, overnight, with shaking, at 37° C. DNA was purified via standard alkaline lysis, with one modification. Specifically, at the end of the procedure, supernatant was passed through a multi-screen filter prior to precipitation. Precipitated DNA was resuspended in water, and used as described in the following example.

Example 2

The purified DNA described in example 1 was sequenced, using commercially available reagents, and well known methods.

Specifically, commercially available products were used to carry out Taq dye deoxy terminator cycle sequencing reactions, using M13 reverse and forward matching primers, which flanked the inserts of the clones. Reaction products were analyzed on a commercially available genetic analyzer.

There were a total of 289,963 shotgun genomic sequences. Open reading frames were obtained from these, and assembled using phred/phrap software, as described by Ewing, et al., *Genome Res* 8(3):186-194 (1998) incorporated by reference. The assembly yielded 2,042 contigs. The "Glimmer" program of Delcher, et al., *Nucl. Acids Res* 27:4636-4641 (1999), incorporated by reference, was applied to the contigs, and yielded 5826 putative open reading frames. Each of these ORFs contained at least 90 base pairs, and overlapped other ORFs by 30 base pairs, or 10% of the ORF size, at most. Any ORFs with "N" or "X," which indicated either poor quality, or repetitive regions were discarded. The "PSORT" program described by Nakai, et al., *Proteins: Structure, Function and Genetics* 11:95-110 (1991), incorporated by reference, was used to predict protein location within the bacterium. Any ORF, with a PSORT score of 0.1 or more (outer membrane or periplasmic space localization), were considered to be potentially useful.

Protein coding genes were identified using known algorithms GeneMark and Glimmer, as described by Delcher, et al., Nucl. Acids Res. 27:4636-4641 (1999), incorporated by reference, after which the "PSORT" program, described by Nakai, et al., Proteins: Structure, Function and Genetics 11:95-110 (1991), incorporated by reference, was used to predict protein localization within the bacterium. The sequences chosen for further analysis were those which the program predicted to encode surface associated proteins. Such proteins are ideal candidates for generation of antibodies.

Once the relevant nucleotide sequences were identified, protocols were developed to amplify them for further work.

In each case, a pair of oligonucleotide primers were developed to hybridize specifically to the target sequence of interest. In general, primers from 18-28 nucleotides long were used. In each case, the forward primer was then modified to add the sequence "CACC" at the 5' end. This facilitates directional cloning in the vector used. As a general principle, the primers were designed to hybridize from 10-25 amino acids away from the start codon, so as to avoid hydrophobic regions that are characteristic of signal peptide sequences. The primer sequences follow

TABLE 1

Oligonucleotide primer sequences employed to amplify the target nucleic sequences by PCR methodology. Molecular weights are from the recombinant proteins obtained in *E. coli* expression systems.

|  | Molecular Weight (KDa) | Primers | SEQ ID NO: |
|---|---|---|---|
| LpL53 | 53.8 | LpL53F: CACCACCAATGTGTTTGGTATAGCG | 47 |
|  |  | LpL53R: CAGCGTTTTGTGATAAAATTAAC | 48 |
| OMPL55 | 53.8 | OMPL55F: CACCGATGCTTACTACGGACTGGATG | 49 |
|  |  | OMPL55R: CAGGAGTGTGATCGAGCTTG | 50 |
| OMPL16 | 15.9 | OMPL16F: CACCCCGTGTTCTTTTGGTTTAGAT | 51 |
|  |  | OMPL16R: TTCCAACAAATCGAATCATCT | 52 |
| OMPL31 | 32 | OMPL31F: CACCAAGAAGGATTCCAACGATGATG | 53 |
|  |  | OMPL31R: TCTCCTGCTTGACAGCCGAC | 54 |
| OMPL15 | 15.2 | OMPL15F: CACCATGCGTGCTGTCAGTAGAGAAAC | 55 |
|  |  | OMPL15R: GTCGACATTGGCAGAATTTACG | 56 |
| OMPL20 | 21.2 | OMPL20F: CACCTTTGCACAATCCAAAGAGAAATG | 57 |
|  |  | OMPL20R: TCATTTCCGAACCGGATGAC | 58 |
| LpL23 | 18.5 | LpL23F: ACCATGGGATCCGCTCTTTTGGTTGATCCAGAG | 59 |
|  |  | LpL23R: GAATTCCTAACAACCAGGACCTTCACAT | 60 |
| LpL40 | 39 | LpL40F: ACCATGGGACTCGAGACGCCTCCTCCTAAAGATCC | 61 |
|  |  | LpL40R: CTCCATGGTCATTTCAAAACTTCTACGGGGC | 62 |
| LpL22 | 22.8 | LpL22F: CACCCCTTCGAGGTTGGAAATCG | 63 |
|  |  | LpL22R: AATCGATGGATCACGTTACG | 64 |
| OMPL17 | 18.4 | OMPL17F: CACCAAACCTGGATATGGAATGGC | 65 |
|  |  | OMPL17R: TACAGAGGTAGAAGCGTTAGAAG | 66 |
| OMPL30 | 29.2 | OMPL30F: CACCAATCGACTTTTCACTGAGTTTCTT | 67 |
|  |  | OMPL30R: CGAAAGTATCAAGAAGAACCGTA | 68 |
| OMPL27 | 27.5 | OMPL27F: CACCCAGGAAACGGAAAACGCTAA | 69 |
|  |  | OMPL27R: CTTATTGTTTGCCGTAGGTTTC | 70 |
| OMPL21 | 21.9 | OMPL21F: CACCATGGGCGCTTTTAATCGG | 71 |
|  |  | OMPL21R: CGGAACTAGGGAACTTTTCAAC | 72 |
| OMPL22 | 20.6 | OMPL22F: CACCATCATTCCTTCGGGAAGTGAC | 73 |
|  |  | OMPL22R: CCATTCTCTGTTGTTTGATCCC | 74 |
| MPL17 | 15.4 | MPL17F: CACCGAAAGTCCCGTAAGGTTCAAA | 75 |
|  |  | MPL17R: TGCAGGAGTTCCCACATTTTA | 76 |
| MPL21 | 31.9 | MPL21F: CACCACGTCTCAAAGTTACGCTTCAG | 77 |
|  |  | MPL21R: TTCTCACCATCCAGCTCGG | 78 |
| OMPAL21 | 20.6 | OMPAL21F: CACCGAGCCTTCAACGCAAGAGCAA | 79 |
|  |  | OMPAL21R: AACGTAAGACGTTGAGTTGCCACA | 80 |

TABLE 1-continued

Oligonucleotide primer sequences employed to amplify the target nucleic sequences by PCR methodology. Molecular weights are from the recombinant proteins obtained in *E. coli* expression systems.

| | Molecular Weight (KDa) | Primers | SEQ ID NO: |
|---|---|---|---|
| OMPL63 | 64.3 | OMPL63F: CACCACGATGATTCAGCCTACTTGG | 81 |
| | | OMPL63R: GAAGTAGAACCGGAAGATTTATTT | 82 |
| OMPL14 | 18.6 | OMPL14F: CACCGGATGCAAACAAGATCCAGTAG | 83 |
| | | OMPL14R: GAAACGCCACTAAGTTAGATCAC | 84 |
| MPL36 | 35.1 | MPL36F: CACCACGTCTTGTGCGTCGGTAGAG | 85 |
| | | MPL36R: CCAAGTATTCTATTTATACGTCCGAG | 86 |
| MPL39 | 30.8 | MPL39F: CACCTCAGTAACTACTGGTCAGTGTAATG | 87 |
| | | MPL39R: CACGTGTTAGTTCTTTGGTTG | 88 |
| MPL40 | 43.2 | MPL40F: CACCTTGTTTTTAAAAAAAAGGAAAGC | 89 |
| | | MPL40R: AACTAAGGAACCGGAGTTGC | 90 |
| MPL21 | 18.6 | MPL21F: CACCGACATGCTTCCTACTTATTCCC | 91 |
| | | MPL21R: CGCTAAAAGTATCACAATGGTAA | 92 |

The amplification was carried out by combining template DNA (1.0 ng), nucleotide triphosphates (0.4 mM), Pfx polymerase (0.5 units, taken from a stock solution of 1 unit/μl), and 0.2 μM primers, at a pH of 8.0. The total reaction volume was 50 μl.

PCR was then carried out in a thermocycler, where the DNA denaturation step was carried out for 3 minutes at 94° C., followed by primer-DNA template annealing at 55° C., for 20 seconds, and nucleotide polymerization for 4 minutes at 68° C. This cycle was repeated, 45 times, except that in the repeats, denaturation was for 20 seconds.

Following amplification, the sequences were cloned into a commercially available vector, "pENTR.TOPO." This vector includes a kanamycin resistance sequence useful in *E. coli* selection a pUC ORI, two "attL1" and "attL2" sites for site-specific recombination, and a TOPO cloning site for directional cloning of blunt end PCR products. Specifically, this is the sequence "CCCTT", which serves as a topoisomerase I binding site.

Cloning was carried out according to manufacturer's instructions, which call for 15 ng of the PCR product, and 5 ng of pENTR.TOPO vector, in 5 mM Tris buffer, pH 7.4, at a total volume of 10 μl. The reaction proceeded for 10 minutes, at room temperature, i.e., about 25° C.

Positive clones were obtained via culture in kanamycin containing Luria Broth.

Following the reaction, the PCR products were integrated into the pENTR.TOPO vector, and were transferred to specific expression vectors very easily, via reaction at the forementioned attR1 and attR2 sites, in the presence of LR Clonase.

Expression was facilitated by use of an expression vector derived from T7, the commercially available pDEST17 vector. This vector includes an ORI, a promoter sequence to facilitate transcription of inserted sequences, a ribosomal binding site, and an ATG start codon.

In the practice of the invention, 2 μl of the cloning mixture described supra, 15 ng of pDEST17, & 4 μl of LR Clonase enzyme mix were combined in Tris-EDTA (10 mM Tris-HCl, 0.1 mM EDTA) buffer, at pH 8, for 60 minutes, at room temperature. After 60 minutes, proteinase K (4 μg) was added for 30 minutes, at 37° C., to inactivate enzymes. Positive clones were isolated from Luria Broth agar plates, which contained 20 μg/ml of ampicillin. DNA sequences, when cloned, included a sequence encoding six His residues, at the N terminus of the protein. This well known technique was used to facilitate the purification of protein via metal affinity chromatography.

Example 3

Figure 2:
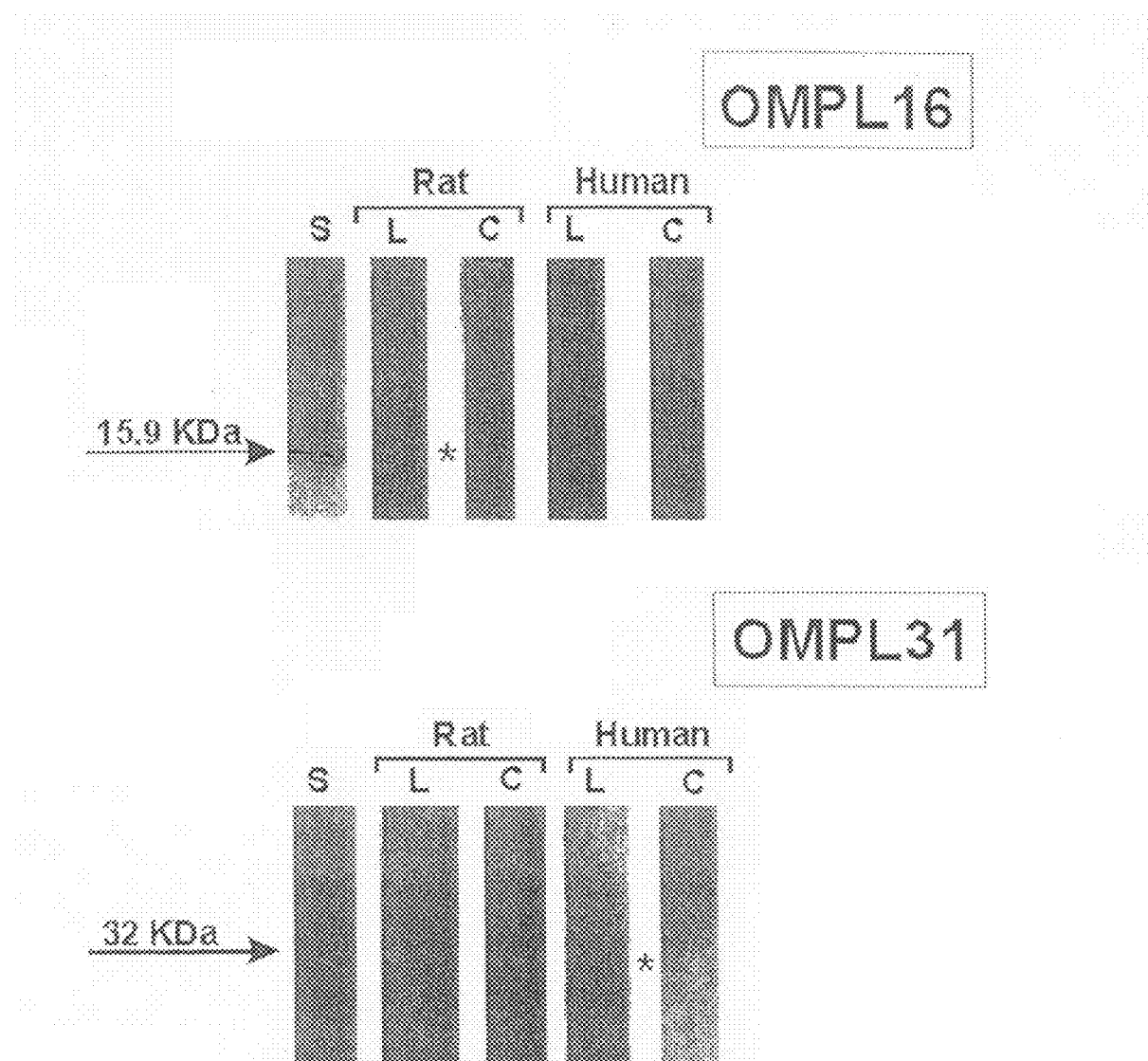
Figure 3:
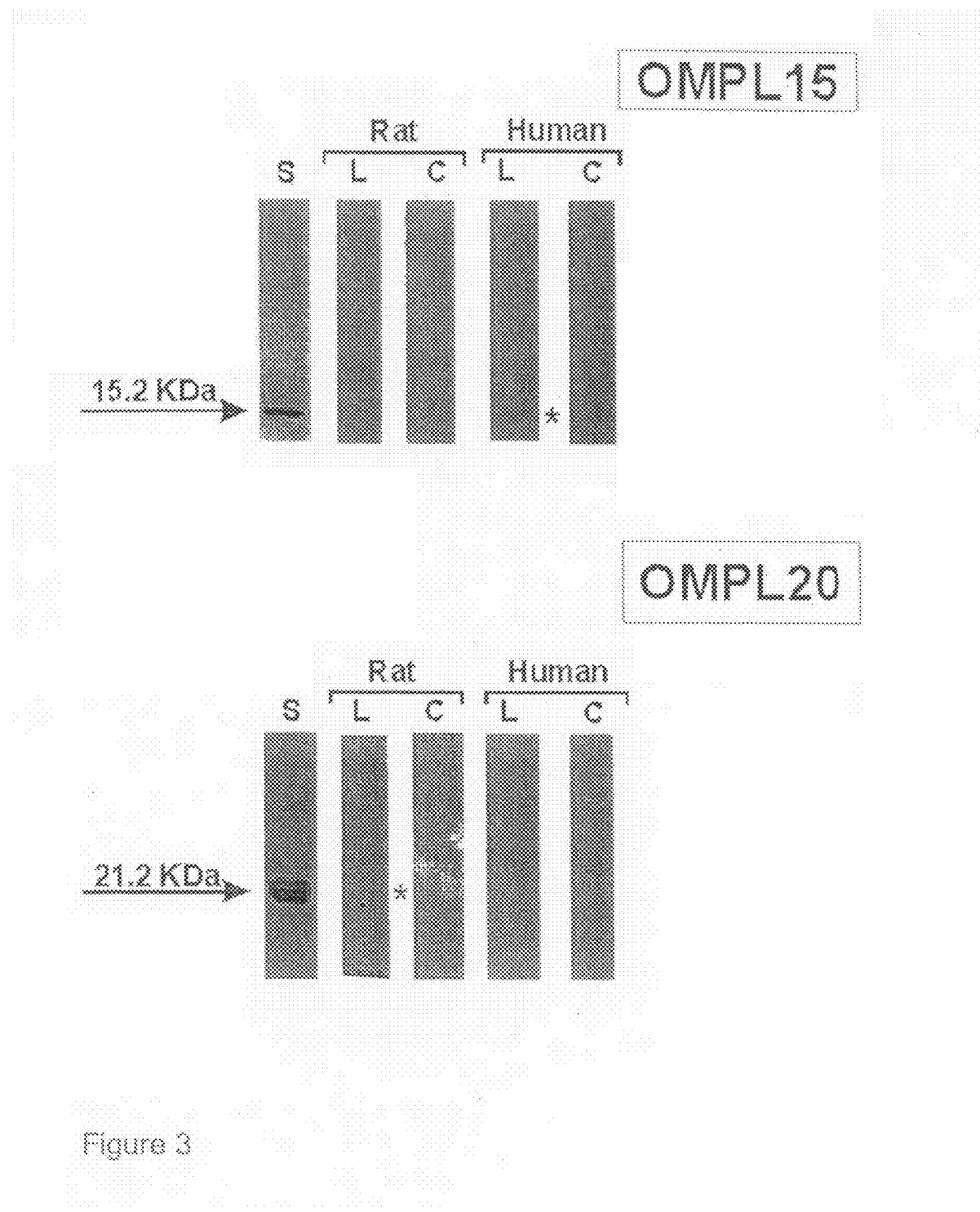
Figure 4:
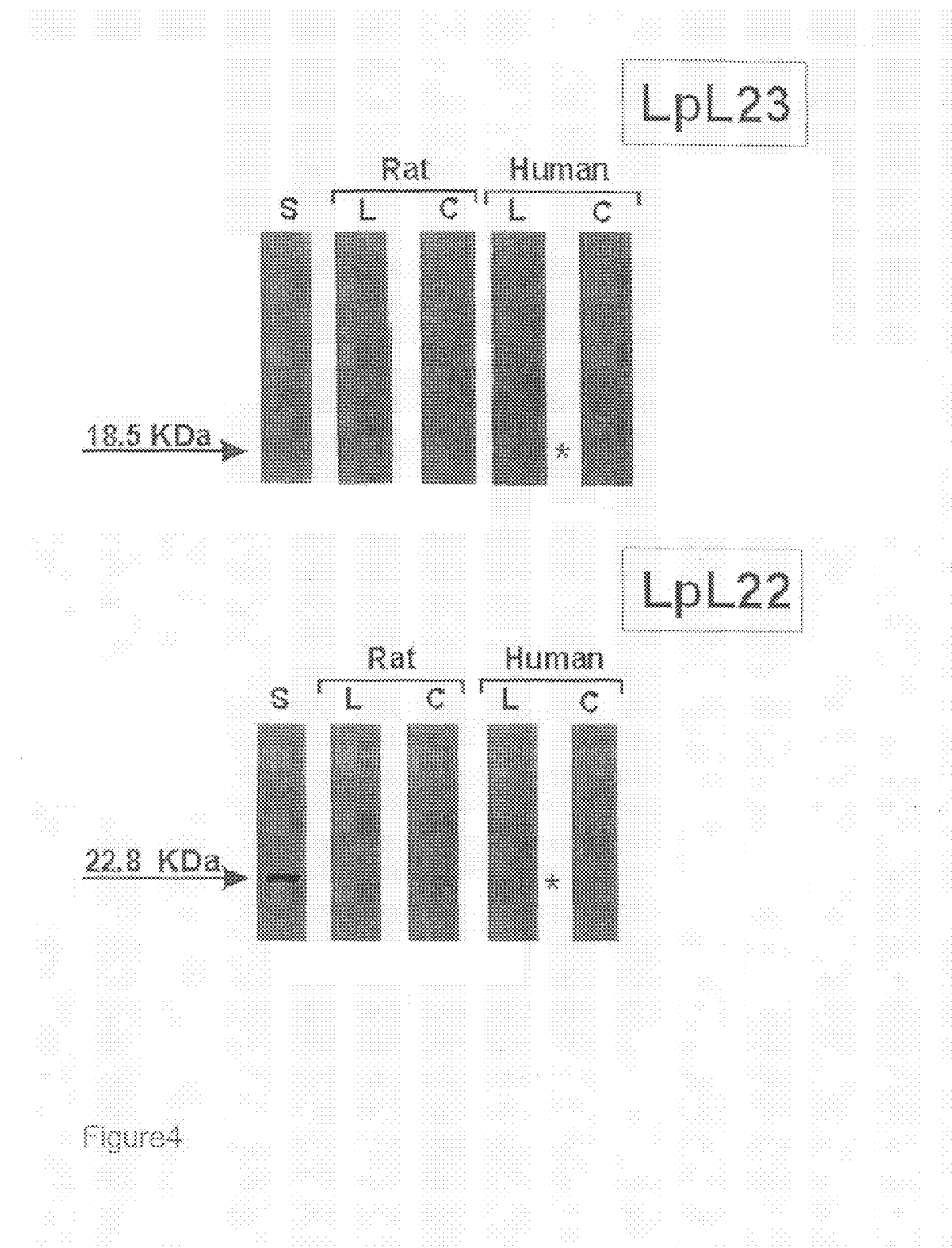
Figure 5:
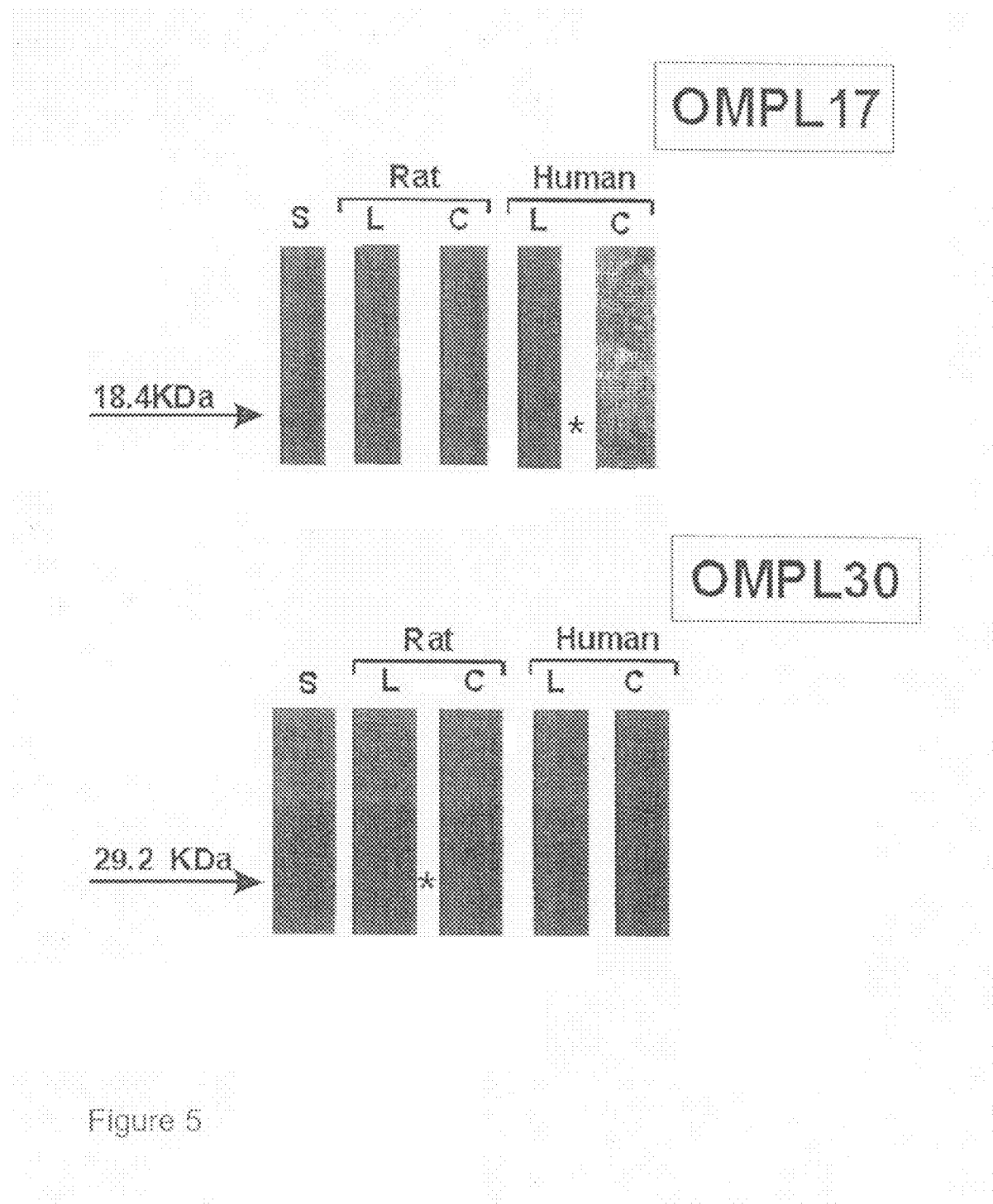
Figure 6:
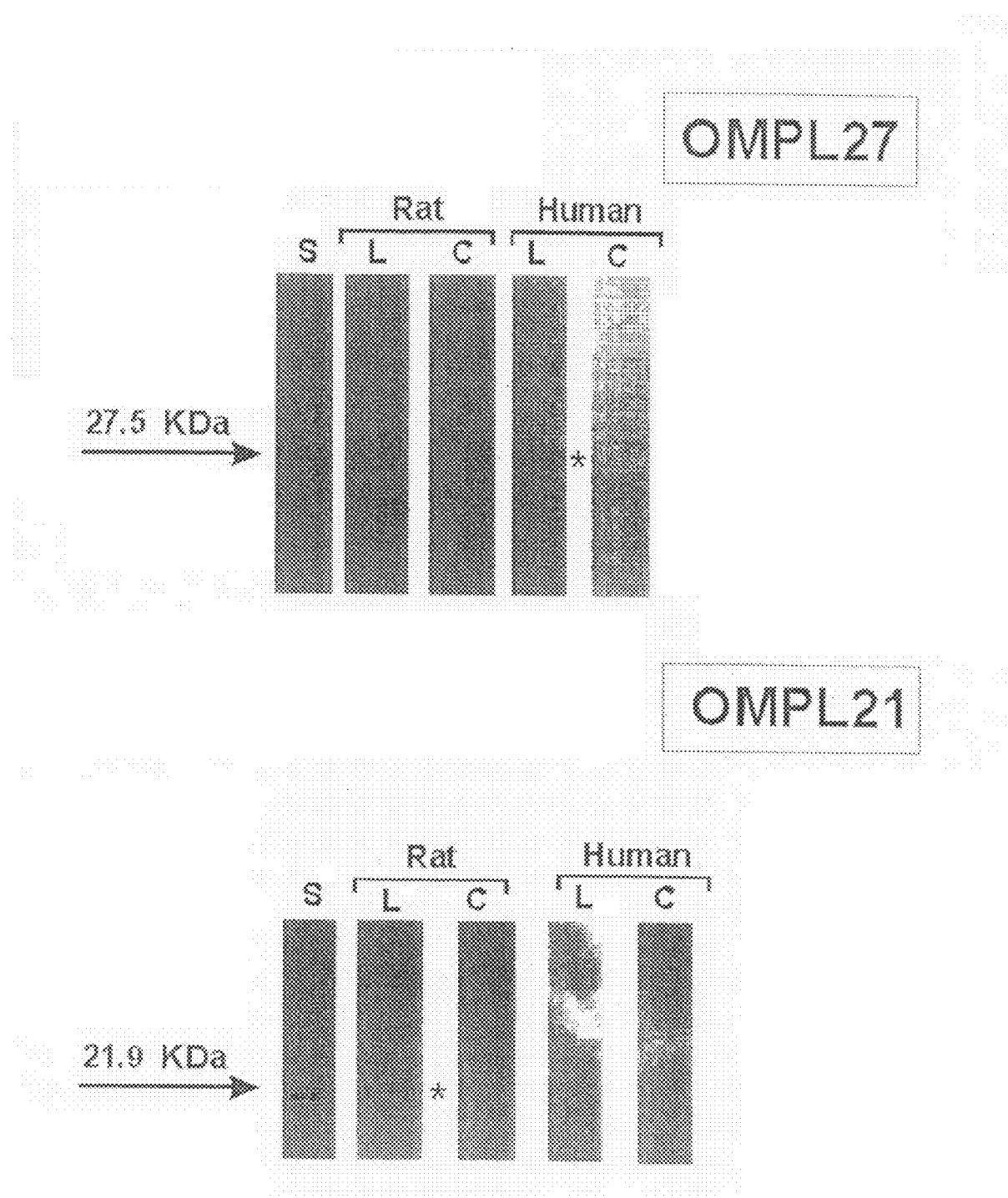
Figure 7:
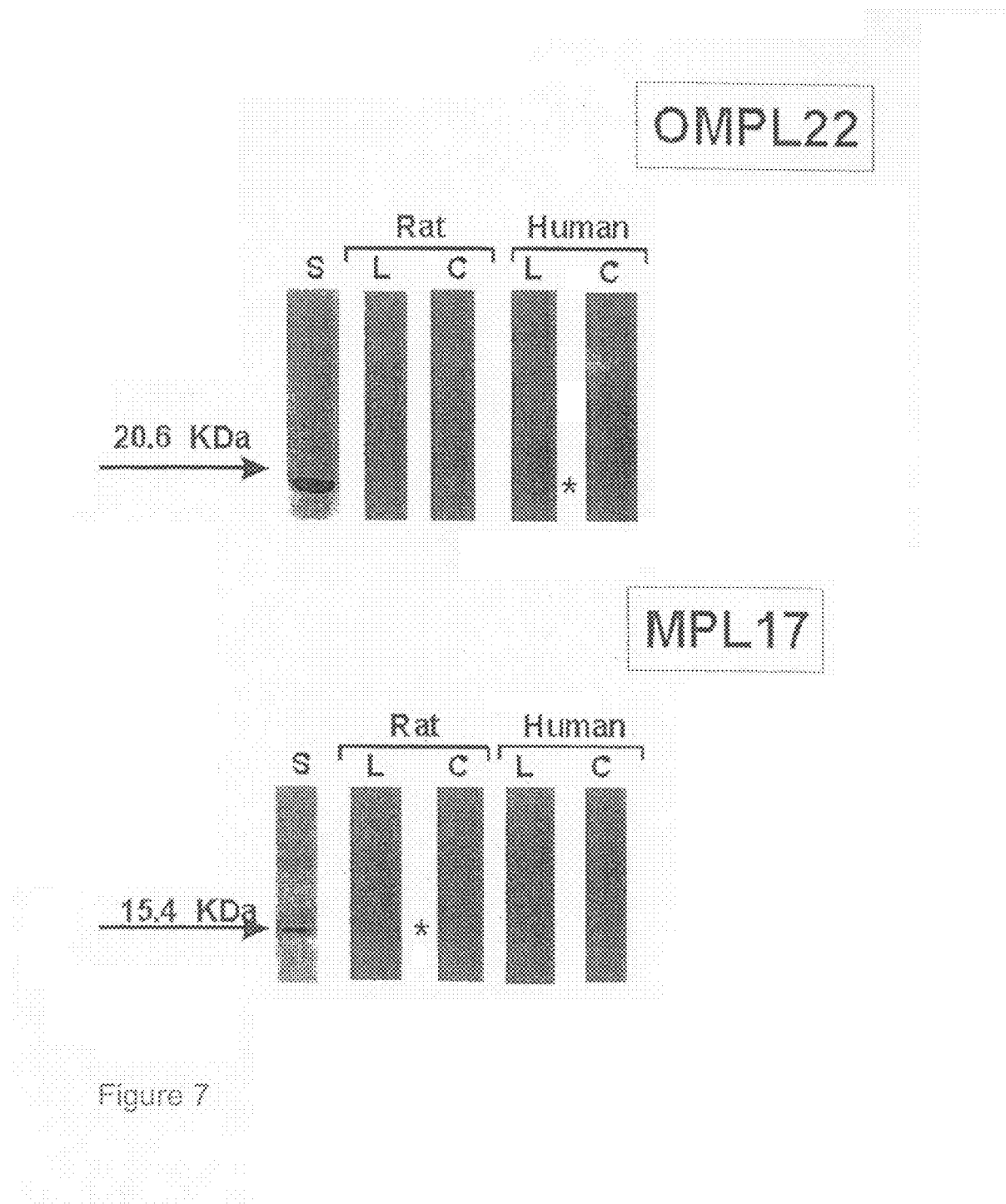
Figure 8:
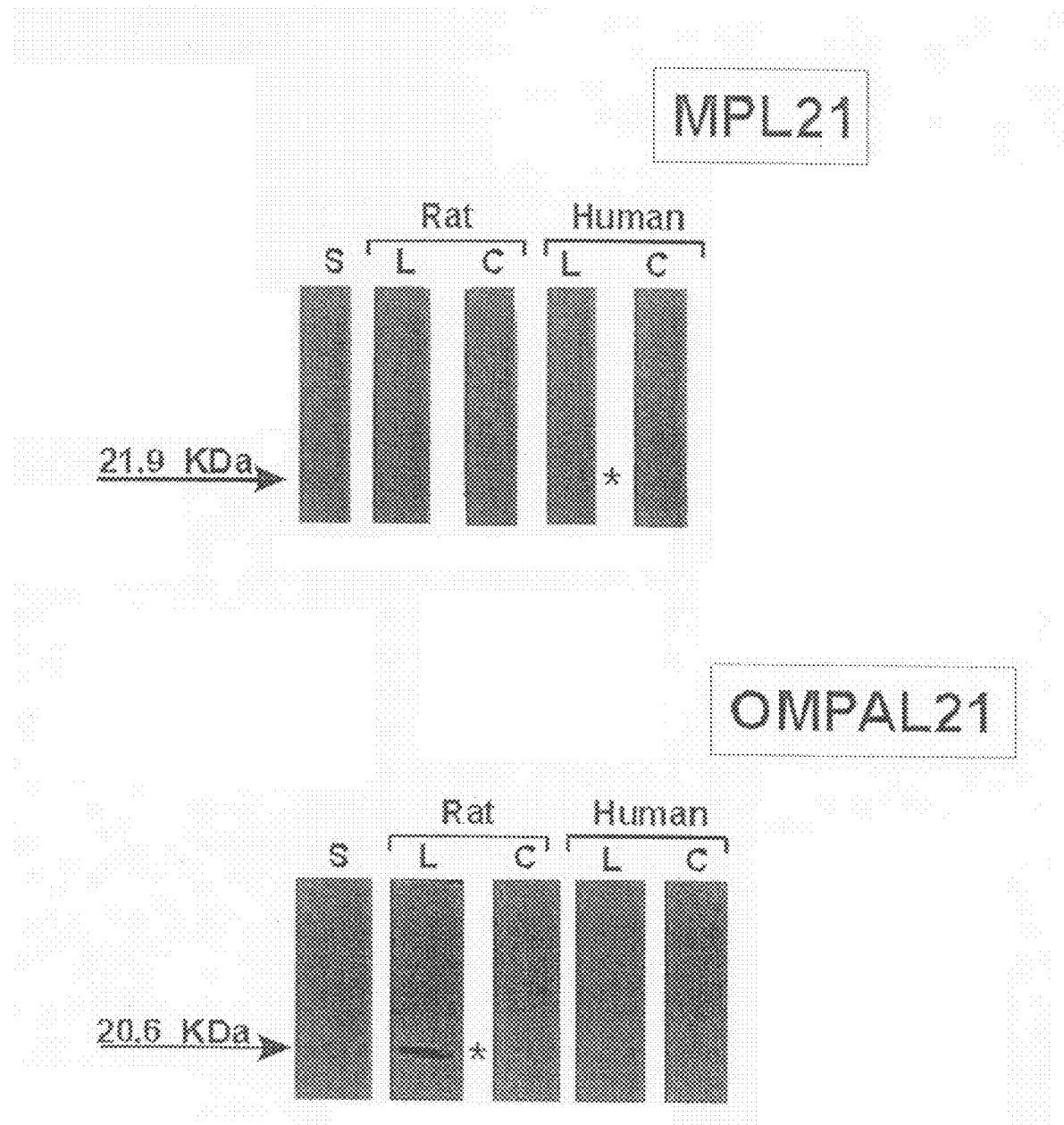
Figure 9:
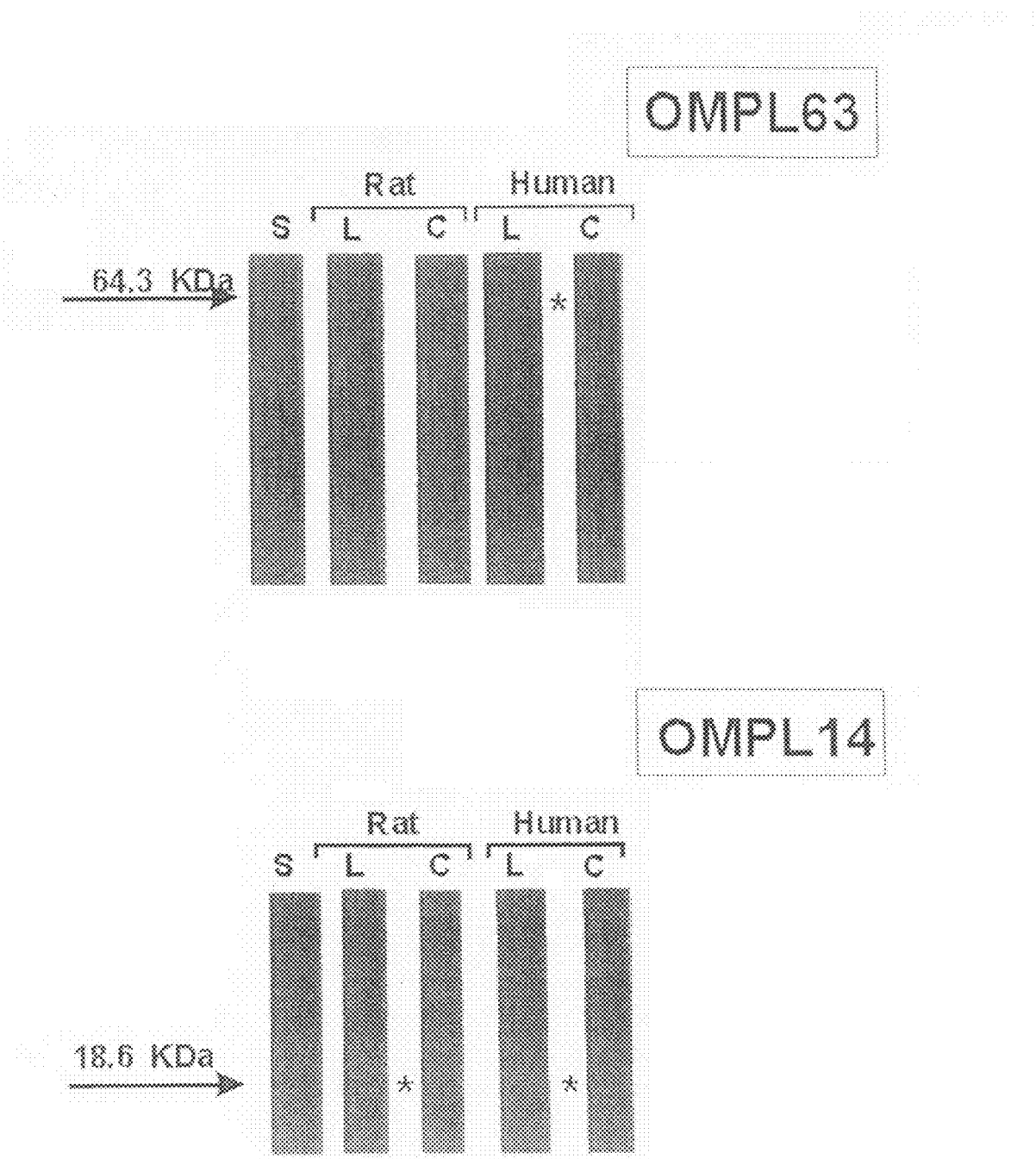
Figure 10:
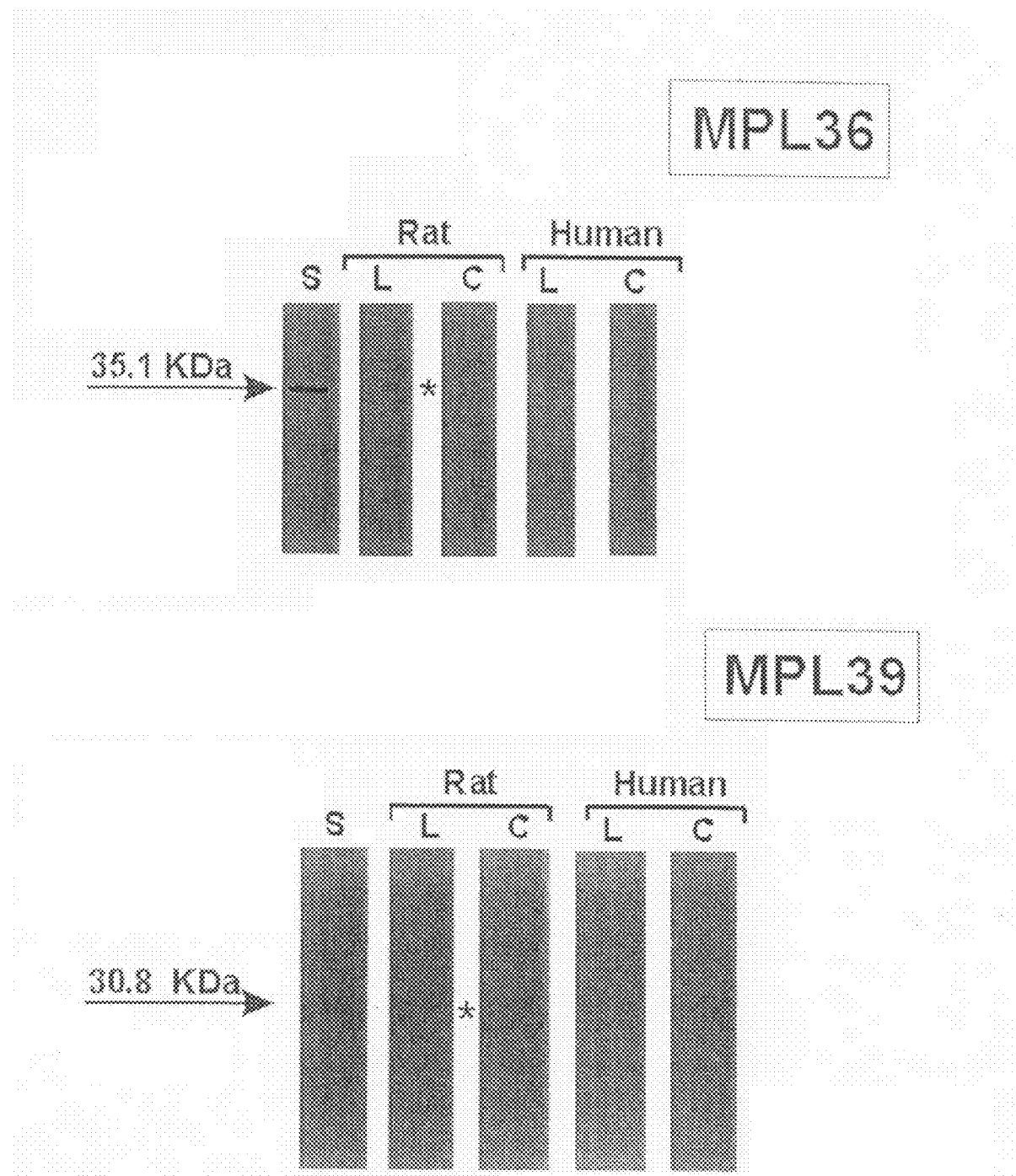
Figure 11:
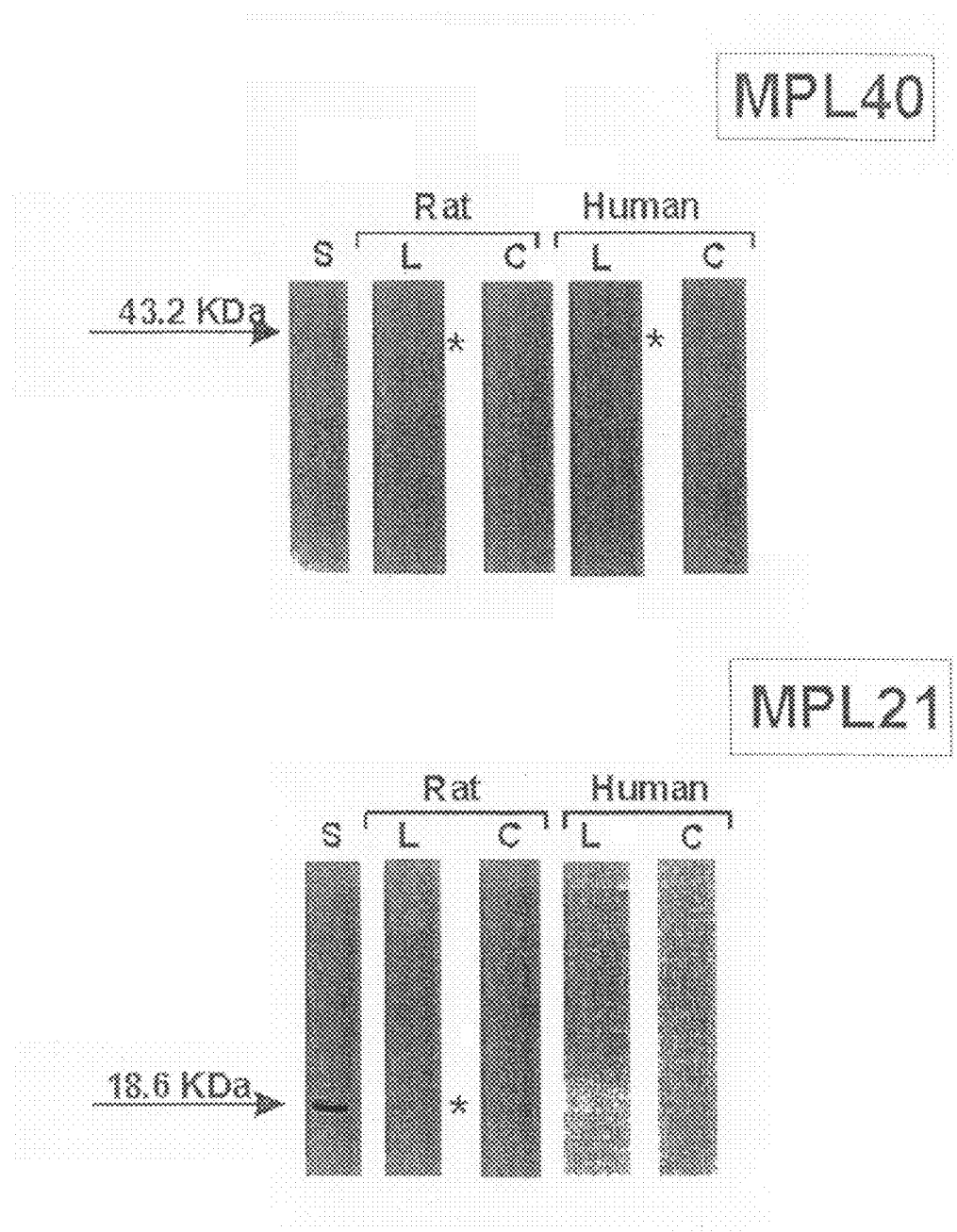

The expression vectors resulting from the preceding examples were used to express the relevant proteins. *E. coli* strains BL21(DE3) or BL21SI were used under inducing conditions, including 1 mM IPTG, or 300 mM NaCl, respectively, using standard methods. Proteins were then analyzed on 10-20% SDS-PAGE gels, under denaturing conditions. Each of FIGS. 1-22 presents an SDS-PAGE pattern for the proteins.

In addition to the SDS-PAGE work, the proteins were purified, by using $Ni^{2+}$ chelating sepharose. Either proteins were mixed with charged beads, or were applied onto columns in a balanced salt buffer (0.1M Tris/0.3 M NaCl, pH 8.0). Any impurities were washed away using the same buffer, with a low concentration of imidazole (20-60 mM). Proteins of interest were then eluted, using a buffer containing imidazole at a concentration of from 0.75 to 1.0M.

Example 4

Once the proteins were purified, they were tested for their ability to bind to antibodies in the sera of infected subjects.

Proteins were purified on 10-15% SDS-PAGE, and then blot transferred to nitrocellulose membranes. Protein was visualized with Ponceau staining.

The proteins were then contacted with either pooled sera obtained from patients who had been diagnosed with leptospiroses, or with rats immunized with *Leptospira interrogans* serovar *Copenhageni*. In the case of rats, dilutions varied from 1/500 to 1/1000. For patients, dilutions ranged from 1/100 to 1/1000. As controls, sera from healthy individuals and non-immunized rats were used.

After contact with the sera, a second antibody, either anti-rat or anti-human IgG, labeled with peroxidase was added, followed by O-phenyl diamine benzidine and hydrogen peroxide.

The results, shown in FIGS. 1-22, inclusive, show that all of the proteins reacted with sera from both sources.

In the discussion of the proteins which follows, signal and transmembrane regions were based upon the presence of hydrophobic amino acids, including Ile, Tyr, Val, Phe, Leu, Met and Ala, and Nielsen, et al., Protein Engineering 12:3-9 (1999), incorporated by reference. Each description is followed by reference to where the sequence appeared in the provisional application.

SEQ ID NO: 1 sets forth a polynucleotide segment encoding an amino acid sequence as set forth in SEQ ID NO: 2 with a predicted molecular weight of 52.7 KDa. It is a new Leptospiral lipoprotein, LpL53, according to the rules described in Haake, Microbiology 146:1491-1504 (2000), incorporated by reference. It has a hydrophobic region of a signal peptide from amino acid 4 to 10 characterized by the presence of Tyr, Leu, Ile, Phe, Leu, Phe, Ile, the lipoprotein signal peptidase cleavage site from amino acid 11-14, with Leu, Phe, Ser, Asn, and the cysteine to be lipidated at position 15 of the polypeptide sequence. (3909 & 3910)

SEQ ID NO: 3 sets forth a polynucleotide segment encoding an amino acid sequence as set forth in SEQ ID NO: 4 with a predicted molecular weight of 55 KDa. It has a signal peptide cleavage site from amino acid 1 to 28. (3531 & 3532)

SEQ ID NO: 5 sets forth a polynucleotide segment encoding an amino acid sequence as set forth in SEQ ID NO: 6 with a predicted molecular weight of 15.8 KDa. It has a signal peptide cleavage site from amino acid 1 to 38. (3489 & 3490)

SEQ ID NO: 7 sets forth a polynucleotide segment encoding an amino acid sequence as set forth in SEQ ID NO: 8 with a predicted molecular weight of 30.9 KDa. It has a signal peptide cleavage site from amino acid 1 to 19. (3871 & 3872)

SEQ ID NO: 9 sets forth a polynucleotide segment encoding an amino acid sequence as set forth in SEQ ID NO: 10 with a predicted molecular weight of 15 KDa. No match with any deposited protein in gene bank was found with this amino acid sequence. It has a signal peptide cleavage site from amino acid 1 to 19 and a transmembrane segment from amino acid 7 to 29, partially overlapping the signal peptide sequence. (3973 & 3974)

SEQ ID NO: 11 is a polynucleotide segment encoding an amino acid sequence as set forth in SEQ ID NO: 12 with a predicted molecular weight of 20.1 KDa. It has a signal peptide cleavage site from amino acid 1 to 20. (3679 & 3680)

SEQ ID NO: 13 corresponds to a polynucleotide segment encoding an amino acid sequence as set forth in SEQ ID NO: 14 with a predicted molecular weight of 23 KDa. This polypeptide sequence is a newly identified Leptospiral lipoprotein, according to Haake, supra. It has a signal peptide hydrophobic region from amino acid 6 to 15 (Ile, Val, Tyr, Val, Ile, Tyr, Leu, Phe, Leu, Ile), characterized by a higher proportion of hydrophobic amino acids, a lipoprotein signal peptides from amino acid 16 to 19 (Ser, Leu, Tyr, Gly) and a cysteine to be lipidated at position 20 of the polypeptide sequence. (81 & 82)

SEQ ID NO: 15 sets forth a polynucleotide segment encoding an amino acid sequence as set forth in SEQ ID NO: 16 with a predicted molecular weight of 40.6 KDa. This polypeptide sequence is a newly isolated Leptospiral lipoprotein, according to the rules described in Haake, supra. It has a signal peptide hydrophobic region from amino acid 7 to 16 (Ile, Leu, Phe, Val, Leu, Thr, Gly, Phe, Ile, Phe), characterized by a higher proportion of hydrophobic amino acids, a lipoprotein signal peptides from amino acid 1 to 20 (Phe, Val, Ser, Ala) and a cysteine to be lipidated at position 21 of the polypeptide sequence. (43 & 44)

SEQ ID NO: 17 corresponds to a polynucleotide segment encoding an amino acid sequence as set forth in SEQ ID NO: 18 with a predicted molecular weight of 22.6 KDa. This polypeptide sequence is a new Leptospiral lipoprotein, according to Haake, supra. It has a signal peptide hydrophobic region from amino acid 8 to 18 (Ile, Asn, Ile, Leu, Phe, Phe, Phe, Leu, Val, Tyr, Phe), a lipoprotein signal peptidase from amino acid 19 to 22 (Leu, Leu, Phe, Gly) that conforms to the rules described in Haake and a cysteine to be lipidated at position 23 of the polypeptide sequence. (125 & 126)

SEQ ID NO: 19 corresponds to a polynucleotide segment encoding an amino acid sequence as set forth in SEQ ID NO: 20 with a predicted molecular weight of 17.3 KDa. It has a signal peptide cleavage site from amino acid 1 to 20. (3991 & 3992)

SEQ ID NO: 21 sets forth a polynucleotide sequence encoding an amino acid sequence as set forth in SEQ ID NO: 22 with a predicted molecular weight of 30.9 KDa. It has a signal peptide cleavage site from amino acid 1 to 27. (3521 & 3522)

SEQ ID NO: 23 sets forth a polynucleotide sequence encoding an amino acid sequence as set forth in SEQ ID NO: 24 with a predicted molecular weight of 27.1 KDa. It has a signal peptide cleavage site from amino acid 1 to 20. It has some similarity to proteins belonging to cytochrome c family. Examples are: di-haem cytochrome c peroxidase and cytochrome c, class I found in bacteria, such as *Bacillus subtilis*. (3533 & 3534)

SEQ ID NO: 25 corresponds to a polynucleotide sequence encoding an amino acid sequence as set forth in SEQ ID NO: 26 with a predicted molecular weight of 20.9 KDa. It has a signal peptide cleavage site from amino acid 1 to 20. (3561 & 3562)

SEQ ID NO: 27 corresponds to a polynucleotide segment encoding an amino acid sequence as set forth in SEQ ID NO: 28 with a predicted molecular weight of 21.2 KDa. It has a signal peptide cleavage site from amino acid 1 to 34. It has some similarity to prokaryotic N-terminal methylation site found in bacterial general secretion pathway protein G and bacterial type II secretion system protein I/J. Examples of bacteria are *E. coli, Xanthomonas canipestris* and *Pseudomonas aeruginosa*. (3675 & 3676)

SEQ ID NO: 29 corresponds to a polynucleotide sequence encoding an amino acid sequence as set forth in SEQ ID NO: 30 with a predicted molecular weight of 16.6 KDa. It has a signal peptide cleavage site from amino acid 1 to 36. (3819 & 3820)

SEQ ID NO: 31 corresponds to a polynucleotide sequence encoding an amino acid sequence as set forth in SEQ ID NO: 32 with a predicted molecular weight of 20.5 KDa. It has a signal peptide cleavage site from amino acid 1 to 22. (3829 & 3830)

SEQ ID NO: 33 is a polynucleotide sequence encoding an amino acid sequence as set forth in SEQ ID NO: 34 with a predicted molecular weight of 20.9 KDa. It has a signal peptide cleavage site from amino acid 1 to 22. This polypeptide has some similarity to proteins having an outer membrane domain (from amino acid 77 to 182) that belong to the OmpA family. Most of these bacterial outer membrane proteins in this group are porin-like, integral membrane proteins, but some are small peptidoglycan-associated lipoprotein (such as pal). *Escherichia coli* is an example of a bacterium expressing a protein and having this domain. (3793 & 3794)

SEQ ID NO: 35 is a polynucleotide sequence encoding an amino acid sequence as set forth in SEQ ID NO: 36 with a predicted molecular weight of 63.5 KDa. It has a signal peptide cleavage site from amino acid 1 to 29. This polypeptide has some similarity to outer membrane efflux protein identified in other bacteria. Examples include the *E. coli* TolC outer membrane protein; the *Rhizobium* nodulation protein; and the *Pseudomonas* FusA protein. (4007 & 4008)

SEQ ID NO: 37 is a polynucleotide sequence encoding an amino acid sequence as set forth in SEQ ID NO: 38 with a predicted molecular weight of 14 KDa. It has a signal peptide cleavage site from amino acid 1 to 23. (3883 & 3884)

SEQ ID NO: 39 is a polynucleotide sequence encoding an amino acid sequence as set forth in SEQ ID NO: 40 with a predicted molecular weight of 35.6 KDa. It has a signal peptide cleavage site from amino acid 1 to 36. This polypeptide sequence has some similarity to bacterial lipoproteins family identified in bacteria, such as, *Escherichia coli*. (2019 & 2020)

SEQ ID NO: 41 is a polynucleotide sequence encoding an amino acid sequence as set forth in SEQ ID NO: 42 with a predicted molecular weight of 39.8 KDa. This protein has a transmembrane region from amino acid 68 to 90. This sequence has similarity to DshA protein of *Leptospira* with unknown function. (1031 & 1032)

SEQ ID NO: 43 is a polynucleotide sequence encoding an amino acid sequence as set forth in SEQ ID NO: 44 with a predicted molecular weight of 40 KDa. It is a cytoplasmic membrane protein, with one transmembrane segment from amino acid 63 to 79. This polypeptide sequence has some homology to the MoxR protein identified in *Borrelia burgdorferi*. The protein family (St. Louis Pfam Web site) (http://pfam.wustl.edu/) predicted two domains in this protein: (i) ATPase family domain associated with various cellular activities (AAA), such as chaperone-like functions that assist in the assembly, operation, or disassembly of protein complexes. (2517 & 2518)

SEQ ID NO: 45 corresponds to a polynucleotide segment encoding an amino acid sequence as set forth in SEQ ID NO: 46 with a predicted molecular weight of 21 KDa. This protein has a signal peptide cleavage site from amino acid 1 to 40 and a transmembrane domain from amino acid 20 to 40. The polypeptide sequence has some similarity to bacterial signal peptidases identified in bacteria, such as, *Sinorhizobium meliloti* and *Bacillus subtilis*. This is a Leptospiral membrane protein MPL21. (1991 & 1992)

The foregoing disclosure set forth various aspects of the invention, including the isolated, *Leptospira* surface proteins, the amino acid sequences of which are set forth as an attachment hereto, and isolated nucleic acid molecules which encode these proteins such as those set forth herein. It will be understood that once an amino acid sequence is known, various degenerate nucleotide sequences can be provided which encode that sequence. All of those are encompassed by this invention.

Also a part of the invention are antibodies which bind specifically to the proteins of the invention, monoclonal antibodies in particular, and the hybridoma which produce them.

"Surface protein" as used herein, refers to proteins which are associated and/or exposed to the surface of the organism.

The proteins of the invention may be used, alone or in combination with each other, as or as components of vaccines. Further, they can be used as immunogens, so as to generate an antibody response. The antibodies thus generated can be used, e.g., as diagnostic tools to determine *Leptospira* infection or presence, as well as components of vaccines used to generate passive immunity. Proteins and antibodies may be administered "neat" or "compounded" with other standard materials used in preparing vaccines, such as carriers, adjuvants, and other materials. Intravenous formulations are one embodiment and, it will be understood that other formulations of vaccines are possible, including intradermal, subcutaneous, oral, such as sublingual forms, and others. The vaccines may be in liquid or "dry" form, such as in lyophilized form. This type of vaccine is especially suitable when it must be carried "in the field," and used at some point in time later than when carried.

The nucleic acid molecules of the invention, as will be understood by the skilled artisan, can be used to produce the proteins described supra, via any of the recombinant methodologies well known to the skilled artisan. They can be placed in, e.g., expression vectors, under control of a promoter or other regulatory element, or they can be used "as is" to transfect or to transform cells. Eukaryotic cells, such as yeast cells, CHO cells, fibroblasts, insect cells, etc., are among the eukaryotes which can be transformed or transfected. Prokaryotes, such as *E. coli* or other bacteria can also be used. The choice of host cell will depend upon many factors, including whether or not glycosylation is desired, and to what end the transformant or transfectant will be used. One way these recombinant cells can be used is as in the form of a cell based vaccine, such as a whole cell vaccine. As the recombinant proteins of the invention are all surface proteins, it is to be expected that they will be expressed on the surface of host cells. If the cells are then processed so as to become non-proliferative, the cells present an ideal vaccine, especially if the host cell is one that is not normally the target of immune surveillance in the host.

Another aspect of the invention is the use of membrane preparations, or cellular "ghosts" of transformants or tranfectants. Such approaches have been used with other bacterial species, so preparation of these is well known. Transformants or transfectants which express the surface proteins of the invention can be used to prepare these materials in a fashion taught by the art.

The proteins have been discussed as vaccines, supra. It is to be understood that the vaccines of the invention can be formulated for any subject. Human vaccines are, of course, included, but so are vaccines for livestock animals, such as sheep, bovine animals, goats, pigs and so forth, and domesticated animals such as pets, confined zoo animals, etcetera. The vaccines may be used prophylactically, e.g., by administering them prior to possible exposure to *Leptospira*, and may also be used post exposure, in order to treat a pre-existing infection.

As will be recognized by the skilled artisan, the use of the proteins of the invention, or portions thereof, constitutes vaccination, and the protein or portion of the protein constitutes the vaccine. Upon administration to the individual or subject, in any of the ways described supra, an immune response results which protects the individual or subject when confronted with the pathogen. Such an approach, i.e., the immunization with one or more proteins or portions of proteins, can be used therapeutically or prophylactically. Passive immunization, as described supra, can also be used. In such a case, antibodies are developed against the proteins or protein portions, and via passive transfer serve a role in, e.g., prophylaxis.

It is to be understood that, while immunization with the proteins or portions of proteins can serve to stimulate an antibody response, cellular immune responses are also a part of the response of the subject to the immunization. It is well within the skill of the artisan to determine which proteins or portions of proteins function as antibody or cellular immune vaccine agents and that artisan can then formulate, e.g., "cocktails" of appropriate mixes of proteins which have the desired, immune effect.

In addition to the use of the proteins as vaccines, it is to be understood that the nucleic acid molecules described herein can also be used as vaccines. Via targeted delivery of nucleic acid molecules, one can assure an "in vivo" supply of the desired protein or protein portion molecules at a site of relevance. The artisan of delivery systems, such as liposomes, adenoviruses, retroviruses, and other formats for the delivery of DNA as immunoprophylactic or a therapeutic agents, and all are envisioned as methods for administering the vaccine. It should be kept in mind that the nucleic acid molecules of the invention include those which encode the proteins of the invention, but differ in nucleotide sequence due to codon degeneracy. Indeed, due to patterns of codon usage, which vary from organism to organism, it may be desirable to alter the sequence to maximize expression of the desired vaccine in the treated subject.

To prepare a vaccine the purified polypeptide can be isolated, lyophilized and/or stabilized, as described supra. The protein may then be adjusted to an appropriate concentration, optionally combined with a suitable vaccine adjuvant, and packaged for use. Suitable adjuvants include but are not limited to: surfactants and pluronic polyols; polyanions, e.g., pyran, dextran sulfate, poly IC; polyacrylics, carbopol; peptides, e.g., muramyl dipeptide, dimethylglycine, oil emulsions, vitamins, cytokines, hormones, aluminum, calcium salts, and mixtures thereof, bacterial and plant products, e.g., *Bacillus* Calmette-Guerin (BCG), complete Freund's adjuvant, and threalose. Alternatively, the immunogenic protein may be incorporated into liposomes for use in a vaccine formulation, may be fused to other immunogenic proteins, or may be conjugated to polysaccharides or other polymers. See Edelman, in New Generation Vaccines (Marshall Decker, N.Y. 1997), incorporated by reference.

The weight of the immunogenic protein included in a given dosage of vaccine can vary widely, e.g., from 5 ug-300 mg., and depends on: the age, weight, and physical condition of the animal or the human subject considered for vaccination.

In addition, the nucleic acid molecules of the invention can be used as vaccines. The rational of this approach is that the DNA will produce the protein following injection thus in turn inducing the desired immune response.

For such vaccines, a pharmaceutical composition can include either a mammalian recombinant expression vector, such as pTARGET, or a construct such as an expression vector, which includes a nucleic acid molecule encoding the protein, operatively linked to transcription control/terminator sequences, combined with a pharmaceutically acceptable carrier. These may include, but are not limited to, aqueous physiologically balanced solutions, artificial lipid-containing substrates, natural lipid-containing substrates, oils, esters, and glycols. Pharmaceutically acceptable carriers can also include a suitable delivery vehicle, such as liposomes, micelles, and cells. Adjuvants for DNA based vaccines can be used, such as CpG oligonucleotides and cytokines. The vaccines can also be delivered by attenuated bacteria, such as *Salmonella*.

Another feature of the invention is the use of the proteins, or portions of the proteins of the invention, as well as nucleic acid molecules and portions of nucleic acid molecules, in the manufacture of kits useful for diagnosis of *Leptospira* infection, either "in the field" or in the laboratory. Such kits involve, e.g., the protein, protein portion, nucleic acid molecule, or nucleic acid molecule portion, in combination with, e.g., a solid phase, such as a bead, mutltiwell plate, etc., to which the component is affixed. The kit can then be used by contacting a sample of interest thereto, followed by a second component, which can also be included in the kit, such as a labeled protein or proteins portion, or labeled nucleic acid molecule or portion of a nucleic acid molecule. When nucleic acid molecules are used in the diagnostic kits of the invention, it is desirable that each portion hybridize to a separate portion of a target nucleic acid molecule.

It may be desirable to screen the proteins and nucleic acid molecules of the invention in, e.g., and animal or cellular model prior to administration to large animals or humans. Standard practice tests a potential vaccine in, e.g., a hamster, mouse, rat or other rodent model to determine it efficacy and strength, and the molecules of this invention may be so tested as well. Testing of the DNA molecules in, e.g., microorganisms such as *E. coli* or other prokaryotes or eukaryote organisms can be carried out to deter mine which are, in fact, good producers, i.e., molecules which produce high yields, and/or produce transformants which react well to culture.

Other aspects of the inventions will be clear to the skilled artisan, and need not be reiterated here.

SEQUENCE LISTING

<160> NUMBER OF SEQ ID NOS: 46

<210> SEQ ID NO 1
<211> LENGTH: 1431
<212> TYPE: DNA
<213> ORGANISM: Leptospira interrogans serovar copenhageni
<220> FEATURE:
<221> NAME/KEY: CDS
<222> LOCATION: (1)...(1428)

<400> SEQUENCE: 1

```
ttg gtt cgt tat tta att ttt ctt ttt att tta ttt tcg aat tgt tta      48
Leu Val Arg Tyr Leu Ile Phe Leu Phe Ile Leu Phe Ser Asn Cys Leu
 1               5                  10                  15 cct acc aat gtg ttt ggt ata gcg gcc ccc gaa aac att gat tat tgg      96
Pro Thr Asn Val Phe Gly Ile Ala Ala Pro Glu Asn Ile Asp Tyr Trp
             20                  25                  30 att cat ttt cta ctg aaa att ccg gat ttt ctt tta cag aat aac gat     144
Ile His Phe Leu Leu Lys Ile Pro Asp Phe Leu Leu Gln Asn Asn Asp
         35                  40                  45 cca ctt cac tca gat tct caa tct gac tca aga tta gat tgg acc tta     192
Pro Leu His Ser Asp Ser Gln Ser Asp Ser Arg Leu Asp Trp Thr Leu
```

-continued

```
            50                  55                  60
tta atc gga gct gaa aat gct caa acg gca agt aaa ggt atc tac gta         240
Leu Ile Gly Ala Glu Asn Ala Gln Thr Ala Ser Lys Gly Ile Tyr Val
 65                  70                  75                  80 gat caa aat ggt ttt atc tac gta gtt ggt gaa acc aat gga ggt gtt         288
Asp Gln Asn Gly Phe Ile Tyr Val Val Gly Glu Thr Asn Gly Gly Val
                 85                  90                  95 tat aat ccg aga cca atc gga atg aaa gat ctc att tta gga aag tat         336
Tyr Asn Pro Arg Pro Ile Gly Met Lys Asp Leu Ile Leu Gly Lys Tyr
            100                 105                 110 gat tct cat aaa aat aca atc tgg act caa caa att gga gct att gac         384
Asp Ser His Lys Asn Thr Ile Trp Thr Gln Gln Ile Gly Ala Ile Asp
                115                 120                 125 gta gca ttg aat gtt agc gct atg act gtc gat cat aac gga aat gtt         432
Val Ala Leu Asn Val Ser Ala Met Thr Val Asp His Asn Gly Asn Val
130                 135                 140 tac gtt acc ggt agt acg ggc aat gat gga ttt ttt ccc aac cca ctt         480
Tyr Val Thr Gly Ser Thr Gly Asn Asp Gly Phe Phe Pro Asn Pro Leu
145                 150                 155                 160 cgt agt tca gaa gat atg ttc gta att aaa ttc aac tcg gac gga acc         528
Arg Ser Ser Glu Asp Met Phe Val Ile Lys Phe Asn Ser Asp Gly Thr
                165                 170                 175 aga gat tgg act aca caa gcc ggc cca cag gaa aaa gaa tcc aga aca         576
Arg Asp Trp Thr Thr Gln Ala Gly Pro Gln Glu Lys Glu Ser Arg Thr
            180                 185                 190 act cca aca agt att tat ata gat aca tct gga aat att ttt gta gtt         624
Thr Pro Thr Ser Ile Tyr Ile Asp Thr Ser Gly Asn Ile Phe Val Val
                195                 200                 205 ggg ttt tca agc gga cct ttc gga ggt ccg gaa tta ggg gcg aac gga         672
Gly Phe Ser Ser Gly Pro Phe Gly Gly Pro Glu Leu Gly Ala Asn Gly
210                 215                 220 ttt ata gct aaa ttt gat cct caa gga aat caa act tgg gtc aga caa         720
Phe Ile Ala Lys Phe Asp Pro Gln Gly Asn Gln Thr Trp Val Arg Gln
225                 230                 235                 240 ctt ttc att agt aga cat act caa atc tcc aca cta tgt gcc gct ttc         768
Leu Phe Ile Ser Arg His Thr Gln Ile Ser Thr Leu Cys Ala Ala Phe
                245                 250                 255 gac aga gtt caa aat act tat gta acc ggt tcg gga aac gca aat ttt         816
Asp Arg Val Gln Asn Thr Tyr Val Thr Gly Ser Gly Asn Ala Asn Phe
            260                 265                 270 gaa acg aat aca gag ata aat gac ttc ggc gtg aaa aat ctt ttt att         864
Glu Thr Asn Thr Glu Ile Asn Asp Phe Gly Val Lys Asn Leu Phe Ile
                275                 280                 285 ttc aaa tat gat aac gat aat gga aac aaa caa ttt ttc gct caa ctt         912
Phe Lys Tyr Asp Asn Asp Asn Gly Asn Lys Gln Phe Phe Ala Gln Leu
290                 295                 300 agt ttc cct tca aga tca att gaa agt aat act ata aca gtt gat act         960
Ser Phe Pro Ser Arg Ser Ile Glu Ser Asn Thr Ile Thr Val Asp Thr
305                 310                 315                 320 tta gga aac gtt ttt gta ggt gga aat agc aac gct gat ttt gga tcc        1008
Leu Gly Asn Val Phe Val Gly Gly Asn Ser Asn Ala Asp Phe Gly Ser
                325                 330                 335 ggt gct gac aga acg tct cat ctt gca acc ttg gta aaa tac aat tct        1056
Gly Ala Asp Arg Thr Ser His Leu Ala Thr Leu Val Lys Tyr Asn Ser
            340                 345                 350 tta ggt gtt ctt caa tgg atc caa caa tta ggc ccg gca caa agc caa        1104
Leu Gly Val Leu Gln Trp Ile Gln Gln Leu Gly Pro Ala Gln Ser Gln
                355                 360                 365 gat cct caa aat aat tat cat act act att tct tct cta gat aca gat        1152
```

```
Asp Pro Gln Asn Asn Tyr His Thr Thr Ile Ser Ser Leu Asp Thr Asp
    370                 375                 380 act gag gga aat gtc tat tca ata ggt tct aca aat gga aat ata tta      1200
Thr Glu Gly Asn Val Tyr Ser Ile Gly Ser Thr Asn Gly Asn Ile Leu
385                 390                 395                 400 aaa gta cat gaa aac tct acc ggt att cga gat cta ttt ttt aca aaa      1248
Lys Val His Glu Asn Ser Thr Gly Ile Arg Asp Leu Phe Phe Thr Lys
                405                 410                 415 cac aat cct tcc gga gaa tta atc tgg tca cga caa ata ggc gct cct      1296
His Asn Pro Ser Gly Glu Leu Ile Trp Ser Arg Gln Ile Gly Ala Pro
            420                 425                 430 aat aga ctt aaa att ggt aat gga ata gca cat gac tta aat gga aat      1344
Asn Arg Leu Lys Ile Gly Asn Gly Ile Ala His Asp Leu Asn Gly Asn
        435                 440                 445 tta tat tac atg ggg aat aca aac gaa tat cta cat gaa gaa gcc gct      1392
Leu Tyr Tyr Met Gly Asn Thr Asn Glu Tyr Leu His Glu Glu Ala Ala
    450                 455                 460 gtg cat gac tta tat ata ttc atc gtc aaa tat aaa tga                  1431
Val His Asp Leu Tyr Ile Phe Ile Val Lys Tyr Lys
465                 470                 475

<210> SEQ ID NO 2
<211> LENGTH: 476
<212> TYPE: PRT
<213> ORGANISM: Leptospira interrogans serovar copenhageni

<400> SEQUENCE: 2

Leu Val Arg Tyr Leu Ile Phe Leu Phe Ile Leu Phe Ser Asn Cys Leu
  1               5                  10                  15

Pro Thr Asn Val Phe Gly Ile Ala Ala Pro Glu Asn Ile Asp Tyr Trp
             20                  25                  30

Ile His Phe Leu Leu Lys Ile Pro Asp Phe Leu Leu Gln Asn Asn Asp
         35                  40                  45

Pro Leu His Ser Asp Ser Gln Ser Asp Ser Arg Leu Asp Trp Thr Leu
     50                  55                  60

Leu Ile Gly Ala Glu Asn Ala Gln Thr Ala Ser Lys Gly Ile Tyr Val
 65                  70                  75                  80

Asp Gln Asn Gly Phe Ile Tyr Val Val Gly Glu Thr Asn Gly Gly Val
                 85                  90                  95

Tyr Asn Pro Arg Pro Ile Gly Met Lys Asp Leu Ile Leu Gly Lys Tyr
            100                 105                 110

Asp Ser His Lys Asn Thr Ile Trp Thr Gln Gln Ile Gly Ala Ile Asp
        115                 120                 125

Val Ala Leu Asn Val Ser Ala Met Thr Val Asp His Asn Gly Asn Val
    130                 135                 140

Tyr Val Thr Gly Ser Thr Gly Asn Asp Gly Phe Phe Pro Asn Pro Leu
145                 150                 155                 160

Arg Ser Ser Glu Asp Met Phe Val Ile Lys Phe Asn Ser Asp Gly Thr
                165                 170                 175

Arg Asp Trp Thr Thr Gln Ala Gly Pro Gln Glu Lys Glu Ser Arg Thr
            180                 185                 190

Thr Pro Thr Ser Ile Tyr Ile Asp Thr Ser Gly Asn Ile Phe Val Val
        195                 200                 205

Gly Phe Ser Ser Gly Pro Phe Gly Gly Pro Glu Leu Gly Ala Asn Gly
    210                 215                 220

Phe Ile Ala Lys Phe Asp Pro Gln Gly Asn Gln Thr Trp Val Arg Gln
225                 230                 235                 240
```

-continued

Leu Phe Ile Ser Arg His Thr Gln Ile Ser Thr Leu Cys Ala Ala Phe
            245                 250                 255

Asp Arg Val Gln Asn Thr Tyr Val Thr Gly Ser Gly Asn Ala Asn Phe
        260                 265                 270

Glu Thr Asn Thr Glu Ile Asn Asp Phe Gly Val Lys Asn Leu Phe Ile
    275                 280                 285

Phe Lys Tyr Asp Asn Asp Asn Gly Asn Lys Gln Phe Ala Gln Leu
290                 295                 300

Ser Phe Pro Ser Arg Ser Ile Glu Ser Asn Thr Ile Thr Val Asp Thr
305                 310                 315                 320

Leu Gly Asn Val Phe Val Gly Gly Asn Ser Asn Ala Asp Phe Gly Ser
                325                 330                 335

Gly Ala Asp Arg Thr Ser His Leu Ala Thr Leu Val Lys Tyr Asn Ser
            340                 345                 350

Leu Gly Val Leu Gln Trp Ile Gln Gln Leu Gly Pro Ala Gln Ser Gln
        355                 360                 365

Asp Pro Gln Asn Asn Tyr His Thr Thr Ile Ser Ser Leu Asp Thr Asp
    370                 375                 380

Thr Glu Gly Asn Val Tyr Ser Ile Gly Ser Thr Asn Gly Asn Ile Leu
385                 390                 395                 400

Lys Val His Glu Asn Ser Thr Gly Ile Arg Asp Leu Phe Phe Thr Lys
                405                 410                 415

His Asn Pro Ser Gly Glu Leu Ile Trp Ser Arg Gln Ile Gly Ala Pro
            420                 425                 430

Asn Arg Leu Lys Ile Gly Asn Gly Ile Ala His Asp Leu Asn Gly Asn
        435                 440                 445

Leu Tyr Tyr Met Gly Asn Thr Asn Glu Tyr Leu His Glu Glu Ala Ala
    450                 455                 460

Val His Asp Leu Tyr Ile Phe Ile Val Lys Tyr Lys
465                 470                 475

<210> SEQ ID NO 3
<211> LENGTH: 1470
<212> TYPE: DNA
<213> ORGANISM: Leptospira interrogans serovar copenhageni
<220> FEATURE:
<221> NAME/KEY: CDS
<222> LOCATION: (1)...(1467)

<400> SEQUENCE: 3

```
ttg ttc gag gga aac atg aga ata ttt caa att tat ata att cta ttg    48
Leu Phe Glu Gly Asn Met Arg Ile Phe Gln Ile Tyr Ile Ile Leu Leu
  1               5                  10                  15 ttg tcc tta ttc ctg gcc cga acg gca tat tcg gaa caa atc gta tcc    96
Leu Ser Leu Phe Leu Ala Arg Thr Ala Tyr Ser Glu Gln Ile Val Ser
             20                  25                  30 tca aaa aaa gac gaa ccg gat gct tac tac gga ctg gat gta aaa gcg   144
Ser Lys Lys Asp Glu Pro Asp Ala Tyr Tyr Gly Leu Asp Val Lys Ala
         35                  40                  45 gtc att tcc cct tcc tac gga gcc aga att aga gac ggc gca tct ggt   192
Val Ile Ser Pro Ser Tyr Gly Ala Arg Ile Arg Asp Gly Ala Ser Gly
     50                  55                  60 att tcc aac tcg gct cca aat gat aag aca ggg ttt tcc act cct tgg   240
Ile Ser Asn Ser Ala Pro Asn Asp Lys Thr Gly Phe Ser Thr Pro Trp
 65                  70                  75                  80 acc att ctt atg att tct aaa acg ttt gaa gaa acc gga atc caa gca   288
Thr Ile Leu Met Ile Ser Lys Thr Phe Glu Glu Thr Gly Ile Gln Ala
```

-continued

```
                    85                      90                      95
gaa ctc tgg ggg gaa ctt atc aga aac aac caa cta aca tcg gat aca      336
Glu Leu Trp Gly Glu Leu Ile Arg Asn Asn Gln Leu Thr Ser Asp Thr
            100                     105                     110 cga act gac tct gga aca aaa caa aat cct tat att cta aac gtt cgt      384
Arg Thr Asp Ser Gly Thr Lys Gln Asn Pro Tyr Ile Leu Asn Val Arg
            115                     120                     125 aga gcc agt att aaa aag aat tgg gaa act tct tcc tat ggc aat tat      432
Arg Ala Ser Ile Lys Lys Asn Trp Glu Thr Ser Ser Tyr Gly Asn Tyr
    130                     135                     140 tct atc ggt ttc gga att caa gaa tta cct cat aca tac act cag tgg      480
Ser Ile Gly Phe Gly Ile Gln Glu Leu Pro His Thr Tyr Thr Gln Trp
145                     150                     155                     160 agt aac tat tgg aga tgg aga tat att gac aaa ggt cct tta gaa tct      528
Ser Asn Tyr Trp Arg Trp Arg Tyr Ile Asp Lys Gly Pro Leu Glu Ser
                165                     170                     175 ctt ggt ttt gca cct caa ccc gcc gac ata gga ttg aat gcg acc gga      576
Leu Gly Phe Ala Pro Gln Pro Ala Asp Ile Gly Leu Asn Ala Thr Gly
            180                     185                     190 aaa tgg tcc att ttc agc gca caa att atg atc agt aac gga gaa ggt      624
Lys Trp Ser Ile Phe Ser Ala Gln Ile Met Ile Ser Asn Gly Glu Gly
            195                     200                     205 tat aga gaa acc caa aac aca aat tct tcc gga atg gac gtt tcc tcc      672
Tyr Arg Glu Thr Gln Asn Thr Asn Ser Ser Gly Met Asp Val Ser Ser
    210                     215                     220 aga ttt tcc att gaa cct atg tta ggc gaa aaa acc aaa acg ggg ctt      720
Arg Phe Ser Ile Glu Pro Met Leu Gly Glu Lys Thr Lys Thr Gly Leu
225                     230                     235                     240 cat tta ttt tat aga aaa gaa aac gct ttc ggc ttt gga gga aac gaa      768
His Leu Phe Tyr Arg Lys Glu Asn Ala Phe Gly Phe Gly Gly Asn Glu
                245                     250                     255 tgt ttc gaa ggg aaa aca aac tgt ctt cca aac gat cta aat ccg gct      816
Cys Phe Glu Gly Lys Thr Asn Cys Leu Pro Asn Asp Leu Asn Pro Ala
            260                     265                     270 act tca tta tat aga caa att caa agt tta cag tcc gac act ttt ggt      864
Thr Ser Leu Tyr Arg Gln Ile Gln Ser Leu Gln Ser Asp Thr Phe Gly
            275                     280                     285 tca gaa tcc aat ttg att tgg aat ggt ttt ttg act tgg aat cta ggt      912
Ser Glu Ser Asn Leu Ile Trp Asn Gly Phe Leu Thr Trp Asn Leu Gly
    290                     295                     300 ttg ggc gga att ctc aaa aaa caa aac agc gga gaa atc cga gat aga      960
Leu Gly Gly Ile Leu Lys Lys Gln Asn Ser Gly Glu Ile Arg Asp Arg
305                     310                     315                     320 ctt cag ccg ttt gca cct ccg att gct ttc gga aaa gac ggt ttc gga     1008
Leu Gln Pro Phe Ala Pro Pro Ile Ala Phe Gly Lys Asp Gly Phe Gly
                325                     330                     335 aag gcg tta tac att tgg tta tcc ata ggc atc gaa aaa ttt cat ctt     1056
Lys Ala Leu Tyr Ile Trp Leu Ser Ile Gly Ile Glu Lys Phe His Leu
            340                     345                     350 ctg ggg aga ata gaa caa ggc aca gga aac aac gga att atg ggt gtc     1104
Leu Gly Arg Ile Glu Gln Gly Thr Gly Asn Asn Gly Ile Met Gly Val
            355                     360                     365 acc gac acg gta caa aaa gaa ttt cta cct ggt tta gga att cca aat     1152
Thr Asp Thr Val Gln Lys Glu Phe Leu Pro Gly Leu Gly Ile Pro Asn
    370                     375                     380 gta gat gct aca tta caa att cgg aat att ctc cca gaa acc aga gca     1200
Val Asp Ala Thr Leu Gln Ile Arg Asn Ile Leu Pro Glu Thr Arg Ala
385                     390                     395                     400 ggt gga tat tcc agt aaa agt tca ttt aga agg atc agt gtg ttt ttc     1248
Gly Gly Tyr Ser Ser Lys Ser Ser Phe Arg Arg Ile Ser Val Phe Phe
```

```
Gly Gly Tyr Ser Ser Lys Ser Ser Phe Arg Arg Ile Ser Val Phe
                405                 410                 415 gaa tgg att gta aat ccc aga ttt aga atg gca atc ggc tat atc gaa      1296
Glu Trp Ile Val Asn Pro Arg Phe Arg Met Ala Ile Gly Tyr Ile Glu
            420                 425                 430 aat aaa aat tat gat ttg aac gga ata tcc caa cgc gct tat atc gat      1344
Asn Lys Asn Tyr Asp Leu Asn Gly Ile Ser Gln Arg Ala Tyr Ile Asp
            435                 440                 445 cca ctc ggg aat gaa aga act gaa aaa gaa tat ctt tct caa tgg aaa      1392
Pro Leu Gly Asn Glu Arg Thr Glu Lys Glu Tyr Leu Ser Gln Trp Lys
        450                 455                 460 gag tca gga aac tta gga att gtt tct tat tcg gtt ttg gat aaa caa      1440
Glu Ser Gly Asn Leu Gly Ile Val Ser Tyr Ser Val Leu Asp Lys Gln
465                 470                 475                 480 ata ctt tta aga act aca ata gaa ttc taa                              1470
Ile Leu Leu Arg Thr Thr Ile Glu Phe
                485
```

<210> SEQ ID NO 4
<211> LENGTH: 489
<212> TYPE: PRT
<213> ORGANISM: Leptospira interrogans serovar copenhageni

<400> SEQUENCE: 4

```
Leu Phe Glu Gly Asn Met Arg Ile Phe Gln Ile Tyr Ile Ile Leu Leu
 1               5                  10                  15

Leu Ser Leu Phe Leu Ala Arg Thr Ala Tyr Ser Glu Gln Ile Val Ser
            20                  25                  30

Ser Lys Lys Asp Glu Pro Asp Ala Tyr Tyr Gly Leu Asp Val Lys Ala
        35                  40                  45

Val Ile Ser Pro Ser Tyr Gly Ala Arg Ile Arg Asp Gly Ala Ser Gly
    50                  55                  60

Ile Ser Asn Ser Ala Pro Asn Asp Lys Thr Gly Phe Ser Thr Pro Trp
65                  70                  75                  80

Thr Ile Leu Met Ile Ser Lys Thr Phe Glu Glu Thr Gly Ile Gln Ala
                85                  90                  95

Glu Leu Trp Gly Glu Leu Ile Arg Asn Asn Gln Leu Thr Ser Asp Thr
            100                 105                 110

Arg Thr Asp Ser Gly Thr Lys Gln Asn Pro Tyr Ile Leu Asn Val Arg
        115                 120                 125

Arg Ala Ser Ile Lys Lys Asn Trp Glu Thr Ser Ser Tyr Gly Asn Tyr
    130                 135                 140

Ser Ile Gly Phe Gly Ile Gln Glu Leu Pro His Thr Tyr Thr Gln Trp
145                 150                 155                 160

Ser Asn Tyr Trp Arg Trp Arg Tyr Ile Asp Lys Gly Pro Leu Glu Ser
                165                 170                 175

Leu Gly Phe Ala Pro Gln Pro Ala Asp Ile Gly Leu Asn Ala Thr Gly
            180                 185                 190

Lys Trp Ser Ile Phe Ser Ala Gln Ile Met Ile Ser Asn Gly Glu Gly
        195                 200                 205

Tyr Arg Glu Thr Gln Asn Thr Asn Ser Ser Gly Met Asp Val Ser Ser
    210                 215                 220

Arg Phe Ser Ile Glu Pro Met Leu Gly Glu Lys Thr Lys Thr Gly Leu
225                 230                 235                 240

His Leu Phe Tyr Arg Lys Glu Asn Ala Phe Gly Phe Gly Gly Asn Glu
                245                 250                 255
```

```
Cys Phe Glu Gly Lys Thr Asn Cys Leu Pro Asn Asp Leu Asn Pro Ala
            260                 265                 270

Thr Ser Leu Tyr Arg Gln Ile Gln Ser Leu Gln Ser Asp Thr Phe Gly
        275                 280                 285

Ser Glu Ser Asn Leu Ile Trp Asn Gly Phe Leu Thr Trp Asn Leu Gly
    290                 295                 300

Leu Gly Gly Ile Leu Lys Lys Gln Asn Ser Gly Glu Ile Arg Asp Arg
305                 310                 315                 320

Leu Gln Pro Phe Ala Pro Ile Ala Phe Gly Lys Asp Gly Phe Gly
                325                 330                 335

Lys Ala Leu Tyr Ile Trp Leu Ser Ile Gly Ile Glu Lys Phe His Leu
            340                 345                 350

Leu Gly Arg Ile Glu Gln Gly Thr Gly Asn Asn Gly Ile Met Gly Val
        355                 360                 365

Thr Asp Thr Val Gln Lys Glu Phe Leu Pro Gly Leu Gly Ile Pro Asn
    370                 375                 380

Val Asp Ala Thr Leu Gln Ile Arg Asn Ile Leu Pro Glu Thr Arg Ala
385                 390                 395                 400

Gly Gly Tyr Ser Ser Lys Ser Ser Phe Arg Arg Ile Ser Val Phe Phe
                405                 410                 415

Glu Trp Ile Val Asn Pro Arg Phe Arg Met Ala Ile Gly Tyr Ile Glu
            420                 425                 430

Asn Lys Asn Tyr Asp Leu Asn Gly Ile Ser Gln Arg Ala Tyr Ile Asp
        435                 440                 445

Pro Leu Gly Asn Glu Arg Thr Glu Lys Glu Tyr Leu Ser Gln Trp Lys
    450                 455                 460

Glu Ser Gly Asn Leu Gly Ile Val Ser Tyr Ser Val Leu Asp Lys Gln
465                 470                 475                 480

Ile Leu Leu Arg Thr Thr Ile Glu Phe
                485

<210> SEQ ID NO 5
<211> LENGTH: 420
<212> TYPE: DNA
<213> ORGANISM: Leptospira interrogans serovar copenhageni
<220> FEATURE:
<221> NAME/KEY: CDS
<222> LOCATION: (1)...(417)

<400> SEQUENCE: 5 atg aga ttc aaa tcg aga tta ttt ttt tct tgt atg atc gtt ttt ttg    48
Met Arg Phe Lys Ser Arg Leu Phe Phe Ser Cys Met Ile Val Phe Leu
 1               5                  10                  15 agc aca act ctg ata gca tat aca atc ctt ccg tgt tct ttt ggt tta    96
Ser Thr Thr Leu Ile Ala Tyr Thr Ile Leu Pro Cys Ser Phe Gly Leu
                20                  25                  30 gat gct tgt tcc tgt gaa cca act cgg gga gaa acg ttg att agt tct   144
Asp Ala Cys Ser Cys Glu Pro Thr Arg Gly Glu Thr Leu Ile Ser Ser
            35                  40                  45 ctc tta ttt tta aca act aac tct gat aaa acg tcc tgt cat agt att   192
Leu Leu Phe Leu Thr Thr Asn Ser Asp Lys Thr Ser Cys His Ser Ile
        50                  55                  60 acg gat tct gta tgt tac gaa agt ttt cat tcc gat tcg ttt tca att   240
Thr Asp Ser Val Cys Tyr Glu Ser Phe His Ser Asp Ser Phe Ser Ile
 65                  70                  75                  80 tta tgc aaa atg tct aat gct gaa atc cgt tta aat gac gtc tgt tct   288
Leu Cys Lys Met Ser Asn Ala Glu Ile Arg Leu Asn Asp Val Cys Ser
                85                  90                  95
```

```
gat caa aat tca gtt gga gat tgt tat cta gat aat tta cga ttg acg      336
Asp Gln Asn Ser Val Gly Asp Cys Tyr Leu Asp Asn Leu Arg Leu Thr
        100                 105                 110 ttt tat aac gat act tat act tct aag gcc gca gaa gat tat tgt aaa      384
Phe Tyr Asn Asp Thr Tyr Thr Ser Lys Ala Ala Glu Asp Tyr Cys Lys
            115                 120                 125 aat caa ctg aga gga ttt ttt tac aat aat aga tga                      420
Asn Gln Leu Arg Gly Phe Phe Tyr Asn Asn Arg
        130                 135

<210> SEQ ID NO 6
<211> LENGTH: 139
<212> TYPE: PRT
<213> ORGANISM: Leptospira interrogans serovar copenhageni

<400> SEQUENCE: 6

Met Arg Phe Lys Ser Arg Leu Phe Phe Ser Cys Met Ile Val Phe Leu
 1               5                  10                  15

Ser Thr Thr Leu Ile Ala Tyr Thr Ile Leu Pro Cys Ser Phe Gly Leu
                20                  25                  30

Asp Ala Cys Ser Cys Glu Pro Thr Arg Gly Glu Thr Leu Ile Ser Ser
            35                  40                  45

Leu Leu Phe Leu Thr Thr Asn Ser Asp Lys Thr Ser Cys His Ser Ile
        50                  55                  60

Thr Asp Ser Val Cys Tyr Glu Ser Phe His Ser Asp Ser Phe Ser Ile
 65                 70                  75                  80

Leu Cys Lys Met Ser Asn Ala Glu Ile Arg Leu Asn Asp Val Cys Ser
                85                  90                  95

Asp Gln Asn Ser Val Gly Asp Cys Tyr Leu Asp Asn Leu Arg Leu Thr
            100                 105                 110

Phe Tyr Asn Asp Thr Tyr Thr Ser Lys Ala Ala Glu Asp Tyr Cys Lys
        115                 120                 125

Asn Gln Leu Arg Gly Phe Phe Tyr Asn Asn Arg
    130                 135

<210> SEQ ID NO 7
<211> LENGTH: 918
<212> TYPE: DNA
<213> ORGANISM: Leptospira interrogans serovar copenhageni
<220> FEATURE:
<221> NAME/KEY: CDS
<222> LOCATION: (1)...(915)

<400> SEQUENCE: 7 gtg ttt gaa aac aat gta gga gaa aat atg att caa aaa tcg att tta       48
Val Phe Glu Asn Asn Val Gly Glu Asn Met Ile Gln Lys Ser Ile Leu
 1               5                  10                  15 ata ttt ctg gtc ttt ctt tcc ttc gtg gtt tgt aag aag gat tcc aac       96
Ile Phe Leu Val Phe Leu Ser Phe Val Val Cys Lys Lys Asp Ser Asn
                20                  25                  30 gat gat gat ctt act gta gct gct ttg gcc gcg ctt tct ggc gga tat      144
Asp Asp Asp Leu Thr Val Ala Ala Leu Ala Ala Leu Ser Gly Gly Tyr
            35                  40                  45 tgt aat gga agt tca gct aat acg gga att aca gta tct aag ggt acg      192
Cys Asn Gly Ser Ser Ala Asn Thr Gly Ile Thr Val Ser Lys Gly Thr
        50                  55                  60 gca act ttg gat gca tcc tca ggt tgt gtt acc gga gtg act act tgt      240
Ala Thr Leu Asp Ala Ser Ser Gly Cys Val Thr Gly Val Thr Thr Cys
 65                 70                  75                  80
```

-continued

```
atg gat tca gcg ctt cct act tgg atc aag aat aac ttt aaa tgt tcc    288
Met Asp Ser Ala Leu Pro Thr Trp Ile Lys Asn Asn Phe Lys Cys Ser
            85                  90                  95 gta gct tat gta tct ggt tcc agt tat ata ttt aaa tct cag aac gtt    336
Val Ala Tyr Val Ser Gly Ser Ser Tyr Ile Phe Lys Ser Gln Asn Val
            100                 105                 110 ccc aat acg aaa agt tat tat tac ggt tca agt tct cct ttg ttt gaa    384
Pro Asn Thr Lys Ser Tyr Tyr Tyr Gly Ser Ser Ser Pro Leu Phe Glu
        115                 120                 125 aca ctt ccg aca gga aat atg cct gca gga aat aat tcc gtt tcg agt    432
Thr Leu Pro Thr Gly Asn Met Pro Ala Gly Asn Asn Ser Val Ser Ser
    130                 135                 140 caa aaa ttc gtt tat acg att cct tcc agt ccc ata aaa gga agt gga    480
Gln Lys Phe Val Tyr Thr Ile Pro Ser Ser Pro Ile Lys Gly Ser Gly
145                 150                 155                 160 act gtc gga aca caa ggc gga ctt gtg tcg ata gga att aca gta aac    528
Thr Val Gly Thr Gln Gly Gly Leu Val Ser Ile Gly Ile Thr Val Asn
                165                 170                 175 ggt ctt gcg att ttt aat aac gca gcc aat cca cct gat act ctc gca    576
Gly Leu Ala Ile Phe Asn Asn Ala Ala Asn Pro Pro Asp Thr Leu Ala
            180                 185                 190 gtg gag gct cag act ttt gat aac ttt gga ggc cat cct caa aat aca    624
Val Glu Ala Gln Thr Phe Asp Asn Phe Gly Gly His Pro Gln Asn Thr
        195                 200                 205 ggg gtt tat cac cat cac gca gcg gta aca aag gtg agt aac aac gat    672
Gly Val Tyr His His His Ala Ala Val Thr Lys Val Ser Asn Asn Asp
    210                 215                 220 tca aat ttg atc gga gtg att ttg gat ggt tac gca att tac gga aaa    720
Ser Asn Leu Ile Gly Val Ile Leu Asp Gly Tyr Ala Ile Tyr Gly Lys
225                 230                 235                 240 aaa tgc gat aac gga act tcg tca act gga gat gac ttt gtc cca act    768
Lys Cys Asp Asn Gly Thr Ser Ser Thr Gly Asp Asp Phe Val Pro Thr
                245                 250                 255 gat ttg gat aat ttg cat ggg cat aca aaa gct acg gtt cac ttt tct    816
Asp Leu Asp Asn Leu His Gly His Thr Lys Ala Thr Val His Phe Ser
            260                 265                 270 act cca act tat cac tat cac ttt gct cct gat gct act gca ggg att    864
Thr Pro Thr Tyr His Tyr His Phe Ala Pro Asp Ala Thr Ala Gly Ile
        275                 280                 285 gac act ttg atg ggt tcc ttt ttt tac gga acg ata gga agt gtt tcc    912
Asp Thr Leu Met Gly Ser Phe Phe Tyr Gly Thr Ile Gly Ser Val Ser
    290                 295                 300 aac taa                                                            918
Asn
305
```

<210> SEQ ID NO 8
<211> LENGTH: 305
<212> TYPE: PRT
<213> ORGANISM: Leptospira interrogans serovar copenhageni

<400> SEQUENCE: 8

```
Val Phe Glu Asn Asn Val Gly Glu Asn Met Ile Gln Lys Ser Ile Leu
 1               5                  10                  15

Ile Phe Leu Val Phe Leu Ser Phe Val Val Cys Lys Lys Asp Ser Asn
            20                  25                  30

Asp Asp Asp Leu Thr Val Ala Ala Leu Ala Ala Leu Ser Gly Gly Tyr
        35                  40                  45

Cys Asn Gly Ser Ser Ala Asn Thr Gly Ile Thr Val Ser Lys Gly Thr
    50                  55                  60
```

```
Ala Thr Leu Asp Ala Ser Ser Gly Cys Val Thr Gly Val Thr Thr Cys
 65                  70                  75                  80

Met Asp Ser Ala Leu Pro Thr Trp Ile Lys Asn Asn Phe Lys Cys Ser
                 85                  90                  95

Val Ala Tyr Val Ser Gly Ser Ser Tyr Ile Phe Lys Ser Gln Asn Val
            100                 105                 110

Pro Asn Thr Lys Ser Tyr Tyr Gly Ser Ser Pro Leu Phe Glu
            115                 120             125

Thr Leu Pro Thr Gly Asn Met Pro Ala Gly Asn Asn Ser Val Ser Ser
        130                 135                 140

Gln Lys Phe Val Tyr Thr Ile Pro Ser Ser Pro Ile Lys Gly Ser Gly
145                 150                 155                 160

Thr Val Gly Thr Gln Gly Gly Leu Val Ser Ile Gly Ile Thr Val Asn
                165                 170                 175

Gly Leu Ala Ile Phe Asn Asn Ala Ala Asn Pro Pro Asp Thr Leu Ala
            180                 185                 190

Val Glu Ala Gln Thr Phe Asp Asn Phe Gly Gly His Pro Gln Asn Thr
            195                 200                 205

Gly Val Tyr His His His Ala Ala Val Thr Lys Val Ser Asn Asn Asp
    210                 215                 220

Ser Asn Leu Ile Gly Val Ile Leu Asp Gly Tyr Ala Ile Tyr Gly Lys
225                 230                 235                 240

Lys Cys Asp Asn Gly Thr Ser Ser Thr Gly Asp Asp Phe Val Pro Thr
                245                 250                 255

Asp Leu Asp Asn Leu His Gly His Thr Lys Ala Thr Val His Phe Ser
            260                 265                 270

Thr Pro Thr Tyr His Tyr His Phe Ala Pro Asp Ala Thr Ala Gly Ile
            275                 280                 285

Asp Thr Leu Met Gly Ser Phe Phe Tyr Gly Thr Ile Gly Ser Val Ser
        290                 295                 300

Asn
305

<210> SEQ ID NO 9
<211> LENGTH: 399
<212> TYPE: DNA
<213> ORGANISM: Leptospira interrogans serovar copenhageni
<220> FEATURE:
<221> NAME/KEY: CDS
<222> LOCATION: (1)...(396)

<400> SEQUENCE: 9 atg cgt ata aga tat atc aca ttt ctt att ttc atg atc cca gcc att     48
Met Arg Ile Arg Tyr Ile Thr Phe Leu Ile Phe Met Ile Pro Ala Ile
  1               5                  10                  15 cta aca atc tcg gtt att tta gct tat ata att gta atg cgt gct gtc     96
Leu Thr Ile Ser Val Ile Leu Ala Tyr Ile Ile Val Met Arg Ala Val
             20                  25                  30 agt aga gaa act tgt gaa aaa aat ctc cga gga ctt tgg tat ttg act    144
Ser Arg Glu Thr Cys Glu Lys Asn Leu Arg Gly Leu Trp Tyr Leu Thr
         35                  40                  45 tct ata ggg agt cgt tgt gtt ctt gct act gaa tgt ttt tat cgt ggc    192
Ser Ile Gly Ser Arg Cys Val Leu Ala Thr Glu Cys Phe Tyr Arg Gly
     50                  55                  60 aac tgt ttg cca tcg tac gat gca gtt act aat tgc gaa cgg ctt ttg    240
Asn Cys Leu Pro Ser Tyr Asp Ala Val Thr Asn Cys Glu Arg Leu Leu
 65                  70                  75                  80
```

```
atc ggc gaa gaa agg aaa tat gtg tat tta cag ttg gga atg cct gta      288
Ile Gly Glu Glu Arg Lys Tyr Val Tyr Leu Gln Leu Gly Met Pro Val
                85                  90                  95 aga agt gga agt ggt cat gag tat ttt gac gga ggt gct atg aat cgt      336
Arg Ser Gly Ser Gly His Glu Tyr Phe Asp Gly Gly Ala Met Asn Arg
            100                 105                 110 tct gaa tta tcc gtt gaa ttc aat cat aat cga tta gtt aaa aaa aat      384
Ser Glu Leu Ser Val Glu Phe Asn His Asn Arg Leu Val Lys Lys Asn
        115                 120                 125 tgt aga ttt gaa tag                                                  399
Cys Arg Phe Glu
    130

<210> SEQ ID NO 10
<211> LENGTH: 132
<212> TYPE: PRT
<213> ORGANISM: Leptospira interrogans serovar copenhageni

<400> SEQUENCE: 10

Met Arg Ile Arg Tyr Ile Thr Phe Leu Ile Phe Met Ile Pro Ala Ile
 1               5                  10                  15

Leu Thr Ile Ser Val Ile Leu Ala Tyr Ile Ile Val Met Arg Ala Val
                20                  25                  30

Ser Arg Glu Thr Cys Glu Lys Asn Leu Arg Gly Leu Trp Tyr Leu Thr
            35                  40                  45

Ser Ile Gly Ser Arg Cys Val Leu Ala Thr Glu Cys Phe Tyr Arg Gly
        50                  55                  60

Asn Cys Leu Pro Ser Tyr Asp Ala Val Thr Asn Cys Glu Arg Leu Leu
65                  70                  75                  80

Ile Gly Glu Glu Arg Lys Tyr Val Tyr Leu Gln Leu Gly Met Pro Val
                85                  90                  95

Arg Ser Gly Ser Gly His Glu Tyr Phe Asp Gly Gly Ala Met Asn Arg
            100                 105                 110

Ser Glu Leu Ser Val Glu Phe Asn His Asn Arg Leu Val Lys Lys Asn
        115                 120                 125

Cys Arg Phe Glu
    130

<210> SEQ ID NO 11
<211> LENGTH: 543
<212> TYPE: DNA
<213> ORGANISM: Leptospira interrogans serovar copenhageni
<220> FEATURE:
<221> NAME/KEY: CDS
<222> LOCATION: (1)...(540)

<400> SEQUENCE: 11 atg ttt aga tta aaa ata ttc att tta ctt tgt att tat tct ttt tcc      48
Met Phe Arg Leu Lys Ile Phe Ile Leu Leu Cys Ile Tyr Ser Phe Ser
 1               5                  10                  15 att ttt gca caa tcc aaa gag aaa tgt tta ttc gga gat tgt aag gat      96
Ile Phe Ala Gln Ser Lys Glu Lys Cys Leu Phe Gly Asp Cys Lys Asp
                20                  25                  30 gga aga ggt att ttt ata gac atc cat gga aac gaa ttc ggc gga gtt     144
Gly Arg Gly Ile Phe Ile Asp Ile His Gly Asn Glu Phe Gly Gly Val
            35                  40                  45 ttc gta aac gga aag tta gaa gga gtg ggt gaa atc aaa ttt aaa aac     192
Phe Val Asn Gly Lys Leu Glu Gly Val Gly Glu Ile Lys Phe Lys Asn
        50                  55                  60
```

-continued

```
gac gga aaa ttt tcc ggc gtt tat aaa aat ccc tca tac cgt gga aaa       240
Asp Gly Lys Phe Ser Gly Val Tyr Lys Asn Pro Ser Tyr Arg Gly Lys
 65                  70                  75                  80 tct aaa ttc att gat tca gat gga aaa gtt gta tat gga acc gag ttt       288
Ser Lys Phe Ile Asp Ser Asp Gly Lys Val Val Tyr Gly Thr Glu Phe
                 85                  90                  95 acg ggt gga tct tgt ggt gac tac gga tgt gaa act tgg act aaa ttt       336
Thr Gly Gly Ser Cys Gly Asp Tyr Gly Cys Glu Thr Trp Thr Lys Phe
            100                 105                 110 ata ttc gat tcg aat gtg aaa tgt gtt ttt cta ggg acg ttt caa aac       384
Ile Phe Asp Ser Asn Val Lys Cys Val Phe Leu Gly Thr Phe Gln Asn
        115                 120                 125 ggt caa aaa acc ggg aaa ggt agt tat act tgt gat aac cat gaa cgt       432
Gly Gln Lys Thr Gly Lys Gly Ser Tyr Thr Cys Asp Asn His Glu Arg
130                 135                 140 ttt gaa gga act tac tca aac gat ttg gcc aat gga atg gga aaa tta       480
Phe Glu Gly Thr Tyr Ser Asn Asp Leu Ala Asn Gly Met Gly Lys Leu
145                 150                 155                 160 acc tat tcc gat gga acc att tgg gaa gga aaa ttt aaa aac ggt cat       528
Thr Tyr Ser Asp Gly Thr Ile Trp Glu Gly Lys Phe Lys Asn Gly His
                165                 170                 175 ccg gtt cgg aaa tga                                                   543
Pro Val Arg Lys
            180
```

<210> SEQ ID NO 12
<211> LENGTH: 180
<212> TYPE: PRT
<213> ORGANISM: Leptospira interrogans serovar copenhageni

<400> SEQUENCE: 12

```
Met Phe Arg Leu Lys Ile Phe Ile Leu Leu Cys Ile Tyr Ser Phe Ser
  1               5                  10                  15

Ile Phe Ala Gln Ser Lys Glu Lys Cys Leu Phe Gly Asp Cys Lys Asp
                 20                  25                  30

Gly Arg Gly Ile Phe Ile Asp Ile His Gly Asn Glu Phe Gly

<212> TYPE: DNA
<213> ORGANISM: Leptospira interrogans serovar copenhageni
<220> FEATURE:
<221> NAME/KEY: C

```
Lys Lys Val Ala Trp Ala Cys Leu Asp Phe Lys Pro Asn Glu Asn Arg
 65                  70                  75                  80

Ala Ile Ile Lys Tyr Tyr Asn Phe Pro Asn Arg Tyr Glu Val Arg Val
                 85                  90                  95

Glu Ala Ile Asn Glu Leu Glu Tyr Lys Leu Asn Tyr Ser Asp Arg Glu
            100                 105                 110

Ala Ser Met Lys Leu Glu Val Thr Gly Asp Tyr Pro Val Lys Glu Gly
        115                 120                 125

Ser Met Gly Phe Leu Thr Ser Thr Val Ser Leu Ser Phe Lys Gly Asp
    130                 135                 140

Ser Lys Val Tyr Asn Asp Val Gly Arg Met Asp Leu Ile Tyr Gly Ser
145                 150                 155                 160

Asp Ser Val Ala Arg Ser Arg His Gly Arg Phe Lys Thr Leu Glu Glu
                165                 170                 175

Cys Glu Ala Gln Ile Ser Ala Asp Glu Glu Leu Ser Glu Thr Leu Arg
            180                 185                 190

Lys Gln Asp Gly Ala Cys Glu Gly Pro Gly Cys
        195                 200

<210> SEQ ID NO 15
<211> LENGTH: 1044
<212> TYPE: DNA
<213> ORGANISM: Leptospira interrogans serovar copenhageni
<220> FEATURE:
<221> NAME/KEY: CDS
<222> LOCATION: (1)...(1041)

<400> SEQUENCE: 15 atg ttt cat ttt aaa acg atc ctg ttt gtt tta act gga ttt att ttt    48
Met Phe His Phe Lys Thr Ile Leu Phe Val Leu Thr Gly Phe Ile Phe
 1               5                  10                  15 ttc gtt tcg gct tgt aaa acg cct cct cct aaa gat ccg tgg atc gtt    96
Phe Val Ser Ala Cys Lys Thr Pro Pro Pro Lys Asp Pro Trp Ile Val
             20                  25                  30 cct tct ctt aaa gag aat gaa aaa cta ttt tta gct cct ttg aaa gtt   144
Pro Ser Leu Lys Glu Asn Glu Lys Leu Phe Leu Ala Pro Leu Lys Val
         35                  40                  45 gat gag ttt gtt tct aaa gat tta gga gga agg cat tat cct gca tcg   192
Asp Glu Phe Val Ser Lys Asp Leu Gly Gly Arg His Tyr Pro Ala Ser
     50                  55                  60 aac gaa ctc aga atc gat ctt ttc aaa ccg tat att gaa aat tta gaa   240
Asn Glu Leu Arg Ile Asp Leu Phe Lys Pro Tyr Ile Glu Asn Leu Glu
 65                  70                  75                  80 ggt ggt tat tta ggt gct gga acg gat cag aac ttt aca ttt atc gtt   288
Gly Gly Tyr Leu Gly Ala Gly Thr Asp Gln Asn Phe Thr Phe Ile Val
             85                  90                  95 tgg gca aag agt aaa tat gta tgg tta atg gat ttt gat tat acg att   336
Trp Ala Lys Ser Lys Tyr Val Trp Leu Met Asp Phe Asp Tyr Thr Ile
        100                 105                 110 tgt cta att aat cga att cat ctt ttg ttt ttt aga att gcc gta gat   384
Cys Leu Ile Asn Arg Ile His Leu Leu Phe Phe Arg Ile Ala Val Asp
    115                 120                 125 cct gaa tcg tat cgg gag ctt tgg gct cga aaa aat aaa cat act tct   432
Pro Glu Ser Tyr Arg Glu Leu Trp Ala Arg Lys Asn Lys His Thr Ser
130                 135                 140 ttt gaa atc ata aag aaa gaa tgg gag aaa gat cca gaa tgg cca ctc   480
Phe Glu Ile Ile Lys Lys Glu Trp Glu Lys Asp Pro Glu Trp Pro Leu
145                 150                 155                 160
```

```
att cga gaa gct tgg gaa gtg gct cat aga ggc aaa tca gac

```
Pro Glu Ser Tyr Arg Glu Leu Trp Ala Arg Lys Asn Lys His Thr Ser
    130                 135                 140

Phe Glu Ile Ile Lys Lys Glu Trp Glu Lys Asp Pro Glu Trp Pro Leu
145                 150                 155                 160

Ile Arg Glu Ala Trp Glu Val Ala His Arg Gly Lys Ser Asp Val Pro
                165                 170                 175

Gln Arg Trp Asn Glu Leu Asp Arg Thr Ser Gln Arg Phe Gly Leu Lys
            180                 185                 190

Thr Phe Ile His Ser Lys Glu Glu Tyr Asn Tyr Ile Arg Asn Met Val
        195                 200                 205

Leu Gln Gly Arg Ile Gln Ile Leu Lys Gly Asp Ile Asn Ala Glu Lys
    210                 215                 220

Ser Met Arg Ser Val Ala Glu Arg Ala Ala Arg Leu Asn Val Pro Ile
225                 230                 235                 240

Arg Val Val Tyr Leu Ser Asn Ile Glu Asp Tyr Phe Ser Tyr Ser Asp
                245                 250                 255

Ser Phe Arg Asp Asn Leu Leu Ser Leu Pro Thr Asp Glu Lys Gly Val
            260                 265                 270

Val Leu Arg Thr Met Gln Asn Gly Thr Lys Glu Glu Tyr Gly Ser Pro
        275                 280                 285

Asp Gly Glu Lys Ile Pro Val Asp Tyr Pro Leu His Tyr Asn Val Gln
    290                 295                 300

Pro Leu Glu Asn Leu Gln Asp Trp Met Leu Leu Ser Gly His Leu His
305                 310                 315                 320

Lys Gly Ile Leu Met Gln Phe Arg Thr Pro Ile Gln Lys Gly Phe Ser
                325                 330                 335

Ile Ile Lys Ser Gly Pro Val Glu Val Leu Lys
            340                 345

<210> SEQ ID NO 17
<211> LENGTH: 576
<212> TYPE: DNA
<213> ORGANISM: Leptospira interrogans serovar copenhageni
<220> FEATURE:
<221> NAME/KEY: CDS
<222> LOCATION: (1)...(573)

<400> SEQUENCE: 17 atg ttc aaa ata tta gta aaa att aat att cta ttt ttc ttt tta gtt     48
Met Phe Lys Ile Leu Val Lys Ile Asn Ile Leu Phe Phe Phe Leu Val
 1               5                  10                  15 tat ttt tta ttg ttt ggg tgt tgt gct cct tcg agg ttg gaa atc gtt     96
Tyr Phe Leu Leu Phe Gly Cys Cys Ala Pro Ser Arg Leu Glu Ile Val
                20                  25                  30 tct atg att ctt tgt gat cat ttc aat cgg gtt gga gaa tgt ctc gaa    144
Ser Met Ile Leu Cys Asp His Phe Asn Arg Val Gly Glu Cys Leu Glu
            35                  40                  45 cct gtg gaa aga aat cat cat tat aaa ata gaa att cca aat cac aaa    192
Pro Val Glu Arg Asn His His Tyr Lys Ile Glu Ile Pro Asn His Lys
        50                  55                  60 aaa ccg gat act tgg gaa aag ttt tct aat tat ctt tac ttt cat gcg    240
Lys Pro Asp Thr Trp Glu Lys Phe Ser Asn Tyr Leu Tyr Phe His Ala
65                  70                  75                  80 aga gaa act cct ggt ttt ctg att cga ttt aat cga aag ttg act cct    288
Arg Glu Thr Pro Gly Phe Leu Ile Arg Phe Asn Arg Lys Leu Thr Pro
                85                  90                  95 tcc gaa tct aaa atg atc aaa gat tct tat tac gcc acg atg agt ttt    336
```

```
Ser Glu Ser Lys Met Ile Lys Asp Ser Tyr Tyr Ala Thr Met Ser Phe
            100                 105                 110 tcc gga act gta gaa agg atg gaa ggt ttt gaa atg gga gaa gat tgg      384
Ser Gly Thr Val Glu Arg Met Glu Gly Phe Glu Met Gly Glu Asp Trp
        115                 120                 125 gtt ggt tcg ttt cag tat ctg ggt tct ata att aaa gaa aaa tta aaa      432
Val Gly Ser Phe Gln Tyr Leu Gly Ser Ile Ile Lys Glu Lys Leu Lys
130                 135                 140 aaa gaa aat cgc ctc tct tcc ttt cct tat aca aat tct atc ttt ccg      480
Lys Glu Asn Arg Leu Ser Ser Phe Pro Tyr Thr Asn Ser Ile Phe Pro
145                 150                 155                 160 gca gaa gtg gaa ttt aga ttc aat tct tct ctt ttt gaa ggg gaa gaa      528
Ala Glu Val Glu Phe Arg Phe Asn Ser Ser Leu Phe Glu Gly Glu Glu
                165                 170                 175 aaa acg aaa att aat cta agt ttt atc gtt ctt cct cca gaa aaa tga      576
Lys Thr Lys Ile Asn Leu Ser Phe Ile Val Leu Pro Pro Glu Lys
            180                 185                 190
```

<210> SEQ ID NO 18
<211> LENGTH: 191
<212> TYPE: PRT
<213> ORGANISM: Leptospira interrogans serovar copenhageni

<400> SEQUENCE: 18

```
Met Phe Lys Ile Leu Val Lys Ile Asn Ile Leu Phe Phe Phe Leu Val
1               5                   10                  15

Tyr Phe Leu Leu Phe Gly Cys Cys Ala Pro Ser Arg Leu Glu Ile Val
            20                  25                  30

Ser Met Ile Leu Cys Asp His Phe Asn Arg Val Gly Glu Cys Leu Glu
        35                  40                  45

Pro Val Glu Arg Asn His His Tyr Lys Ile Glu Ile Pro Asn His Lys
    50                  55                  60

Lys Pro Asp Thr Trp Glu Lys Phe Ser Asn Tyr Leu Tyr Phe His Ala
65                  70                  75                  80

Arg Glu Thr Pro Gly Phe Leu Ile Arg Phe Asn Arg Lys Leu Thr Pro
                85                  90                  95

Ser Glu Ser Lys Met Ile Lys Asp Ser Tyr Tyr Ala Thr Met Ser Phe
            100                 105                 110

Ser Gly Thr Val Glu Arg Met Glu Gly Phe Glu Met Gly Glu Asp Trp
        115                 120                 125

Val Gly Ser Phe Gln Tyr Leu Gly Ser Ile Ile Lys Glu Lys Leu Lys
130                 135                 140

Lys Glu Asn Arg Leu Ser Ser Phe Pro Tyr Thr Asn Ser Ile Phe Pro
145                 150                 155                 160

Ala Glu Val Glu Phe Arg Phe Asn Ser Ser Leu Phe Glu Gly Glu Glu
                165                 170                 175

Lys Thr Lys Ile Asn Leu Ser Phe Ile Val Leu Pro Pro Glu Lys
            180                 185                 190
```

<210> SEQ ID NO 19
<211> LENGTH: 483
<212> TYPE: DNA
<213> ORGANISM: Leptospira interrogans serovar copenhageni
<220> FEATURE:
<221> NAME/KEY: CDS
<222> LOCATION: (1)...(480)

<400> SEQUENCE: 19

```
atg aag aaa tta ttc gtt att gct ctg gct ctc ttt atg gtt tct aac       48
```

```
Met Lys Lys Leu Phe Val Ile Ala Leu Ala Leu Phe Met Val Ser Asn
  1               5                  10                  15 ctt tct gca aaa cct gga tat gga atg gcg gga tgc ggt tta gga tct    96
Leu Ser Ala Lys Pro Gly Tyr Gly Met Ala Gly Cys Gly Leu Gly Ser
             20                  25                  30 ata atc att aaa gat aat ggt ttt gtg caa att ttt gca act acc tca   144
Ile Ile Ile Lys Asp Asn Gly Phe Val Gln Ile Phe Ala Thr Thr Ser
             35                  40                  45 aat cta act tct tac aat caa act ttt gga att act tct ggc act tcc   192
Asn Leu Thr Ser Tyr Asn Gln Thr Phe Gly Ile Thr Ser Gly Thr Ser
         50                  55                  60 aat tgc agt tca gat gga atc gtg aac aat gac aaa gca aag gaa att   240
Asn Cys Ser Ser Asp Gly Ile Val Asn Asn Asp Lys Ala Lys Glu Ile
 65                  70                  75                  80 ttt gtt cat atg aac tac gaa agt ctt gaa caa gaa att gca atg gga   288
Phe Val His Met Asn Tyr Glu Ser Leu Glu Gln Glu Ile Ala Met Gly
                 85                  90                  95 aaa gga gag aaa ctt tcc agt tta gct gca ctt ttt gga tgt tct aac   336
Lys Gly Glu Lys Leu Ser Ser Leu Ala Ala Leu Phe Gly Cys Ser Asn
                100                 105                 110 gat tct aaa aga ttt aaa gaa gtt gct aaa gaa aat ttc tct aaa att   384
Asp Ser Lys Arg Phe Lys Glu Val Ala Lys Glu Asn Phe Ser Lys Ile
            115                 120                 125 ttc acg acg gca gca att aaa aat ccg act gta atg ctt tct aat tta   432
Phe Thr Thr Ala Ala Ile Lys Asn Pro Thr Val Met Leu Ser Asn Leu
        130                 135                 140 gaa ttg gaa gtt gga aaa gat aca gaa tta aag aac agc tgt aaa atc   480
Glu Leu Glu Val Gly Lys Asp Thr Glu Leu Lys Asn Ser Cys Lys Ile
145                 150                 155                 160 taa                                                               483

<210> SEQ ID NO 20
<211> LENGTH: 160
<212> TYPE: PRT
<213> ORGANISM: Leptospira interrogans serovar copenhageni

<400> SEQUENCE: 20

Met Lys Lys Leu Phe Val Ile Ala Leu Ala Leu Phe Met Val Ser Asn
  1               5                  10                  15

Leu Ser Ala Lys Pro

<210> SEQ ID NO 21
<211> LENGTH: 819
<212> TYPE: DNA
<213> ORGANISM: Leptospira interrogans serovar copenhageni
<220> FEATURE:
<221> NAME/KEY: CDS
<222> LOCATION: (1)...(816)

<400> SEQUENCE: 21

| | | | | | | | | | | | | | | | | |
|---|---|---|---|---|---|---|---|---|---|---|---|---|---|---|---|---|
| atg | ttt | tcc | cgg | tgt | cga | att | ttc | tta | aaa | cct | acg | acc | cta | att | tgg | 48 |
| Met | Phe | Ser | Arg | Cys | Arg | Ile | Phe | Leu | Lys | Pro | Thr | Thr | Leu | Ile | Trp | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ttt | gca | att | ctt | ccg | gga | gcc | tta | tct | gct | tct | cct | caa | aaa | cca | gga | 96 |
| Phe | Ala | Ile | Leu | Pro | Gly | Ala | Leu | Ser | Ala | Ser | Pro | Gln | Lys | Pro | Gly | |
| | | | 20 | | | | | 25 | | | | | 30 | | | |

| | | | | | | | | | | | | | | | | |
|---|---|---|---|---|---|---|---|---|---|---|---|---|---|---|---|---|
| acc | ttc | gaa | ttg | tta | ggt | ggt | tac | caa | ccc | aat | tgg | aat | cga | ctt | ttc | 144 |
| Thr | Phe | Glu | Leu | Leu | Gly | Gly | Tyr | Gln | Pro | Asn | Trp | Asn | Arg | Leu | Phe | |
| | | 35 | | | | | 40 | | | | | 45 | | | | |

| | | | | | | | | | | | | | | | | |
|---|---|---|---|---|---|---|---|---|---|---|---|---|---|---|---|---|
| act | gag | ttt | ctt | ccg | aaa | cgt | aca | gca | caa | act | ggt | aac | cta | cct | tct | 192 |
| Thr | Glu | Phe | Leu | Pro | Lys | Arg | Thr | Ala | Gln | Thr | Gly | Asn | Leu | Pro | Ser | |
| 50 | | | | | 55 | | | | | 60 | | | | | | |

| | | | | | | | | | | | | | | | | |
|---|---|---|---|---|---|---|---|---|---|---|---|---|---|---|---|---|
| agc | ggc | gtc | att | tcc | aga | gaa | gaa | gag | gac | ata | gaa | aat | cca | gag | gaa | 240 |
| Ser | Gly | Val | Ile | Ser | Arg | Glu | Glu | Glu | Asp | Ile | Glu | Asn | Pro | Glu | Glu | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| aca | gaa | gaa | gat | aaa | caa | gaa | gga | tac | caa | gac | aat | cga | aaa | acg | gaa | 288 |
| Thr | Glu | Glu | Asp | Lys | Gln | Glu | Gly | Tyr | Gln | Asp | Asn | Arg | Lys | Thr | Glu | |
| | | | | 85 | | | | | 90 | | | | | 95 | | |

| | | | | | | | | | | | | | | | | |
|---|---|---|---|---|---|---|---|---|---|---|---|---|---|---|---|---|
| gtt | gga | gtt | tgg | gta | gga | gct | tcc | aat | ccg | tta | ccc | gga | acc | gaa | act | 336 |
| Val | Gly | Val | Trp | Val | Gly | Ala | Ser | Asn | Pro | Leu | Pro | Gly | Thr | Glu | Thr | |
| | | | 100 | | | | | 105 | | | | | 110 | | | |

| | | | | | | | | | | | | | | | | |
|---|---|---|---|---|---|---|---|---|---|---|---|---|---|---|---|---|
| caa | aaa | tat | ctg | gat | act | acg | tta | ggt | ggc | ggt | ttc | ttt | ttt | aga | att | 384 |
| Gln | Lys | Tyr | Leu | Asp | Thr | Thr | Leu | Gly | Gly | Gly | Phe | Phe | Phe | Arg | Ile | |
| | | 115 | | | | | 120 | | | | | 125 | | | | |

| | | | | | | | | | | | | | | | | |
|---|---|---|---|---|---|---|---|---|---|---|---|---|---|---|---|---|
| ccc | tgg | cct | tgg | atc | ttt | tat | ctc | gaa | atg | gga | gcc | ttt | tac | gca | aat | 432 |
| Pro | Trp | Pro | Trp | Ile | Phe | Tyr | Leu | Glu | Met | Gly | Ala | Phe | Tyr | Ala | Asn | |
| | 130 | | | | | 135 | | | | | 140 | | | | | |

| | | | | | | | | | | | | | | | | |
|---|---|---|---|---|---|---|---|---|---|---|---|---|---|---|---|---|
| tat | ctt | tcg | gca | aca | gaa | aga | gct | ttg | act | aca | att | ccg | gtc | tat | ctt | 480 |
| Tyr | Leu | Ser | Ala | Thr | Glu | Arg | Ala | Leu | Thr | Thr | Ile | Pro | Val | Tyr | Leu | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| gct | ttg | ggt | tat | aaa | att | cct | tta | gat | ctt | cca | att | tcg | ttt | atc | ctt | 528 |
| Ala | Leu | Gly | Tyr | Lys | Ile | Pro | Leu | Asp | Leu | Pro | Ile | Ser | Phe | Ile | Leu | |
| | | | | 165 | | | | | 170 | | | | | 175 | | |

| | | | | | | | | | | | | | | | | |
|---|---|---|---|---|---|---|---|---|---|---|---|---|---|---|---|---|
| cgt | gcg | gga | ggt | gga | gaa | gcg | ttt | gta | gta | gca | aga | cct | tcc | aac | aca | 576 |
| Arg | Ala | Gly | Gly | Gly | Glu | Ala | Phe | Val | Val | Ala | Arg | Pro | Ser | Asn | Thr | |
| | | | 180 | | | | | 185 | | | | | 190 | | | |

| | | | | | | | | | | | | | | | | |
|---|---|---|---|---|---|---|---|---|---|---|---|---|---|---|---|---|
| tct | cgt | tgg | gat | cca | atg | atg | att | gta | gga | tta | gaa | act | agt | ttt | gta | 624 |
| Ser | Arg | Trp | Asp | Pro | Met | Met | Ile | Val | Gly | Leu | Glu | Thr | Ser | Phe | Val | |
| | | 195 | | | | | 200 | | | | | 205 | | | | |

| | | | | | | | | | | | | | | | | |
|---|---|---|---|---|---|---|---|---|---|---|---|---|---|---|---|---|
| gct | gga | aaa | aaa | atc | cga | atc | gga | att | cga | atc | gat | tac | aat | aaa | att | 672 |
| Ala | Gly | Lys | Lys | Ile | Arg | Ile | Gly | Ile | Arg | Ile | Asp | Tyr | Asn | Lys | Ile | |
| | 210 | | | | | 215 | | | | | 220 | | | | | |

| | | | | | | | | | | | | | | | | |
|---|---|---|---|---|---|---|---|---|---|---|---|---|---|---|---|---|
| tat | gag | tct | cgt | atg | gac | gcc | cca | gga | gaa | aca | aaa | tat | cct | tac | acg | 720 |
| Tyr | Glu | Ser | Arg | Met | Asp | Ala | Pro | Gly | Glu | Thr | Lys | Tyr | Pro | Tyr | Thr | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| agt | cct | tac | gaa | gat | tcc | aga | ttg | agt | aac | ccc | aat | tat | tac | aga | gta | 768 |
| Ser | Pro | Tyr | Glu | Asp | Ser | Arg | Leu | Ser | Asn | Pro | Asn | Tyr | Tyr | Arg | Val | |
| | | | | 245 | | | | | 250 | | | | | 255 | | |

| | | | | | | | | | | | | | | | | |
|---|---|---|---|---|---|---|---|---|---|---|---|---|---|---|---|---|
| gta | gat | act | gaa | ttt | ttt | cag | ttc | ggt | ttg | atg | gtg | agt | gta | ttt | tta | 816 |
| Val | Asp | Thr | Glu | Phe | Phe | Gln | Phe | Gly | Leu | Met | Val | Ser | Val | Phe | Leu | |
| | | | 260 | | | | | 265 | | | | | 270 | | | |

```
                                                                                  819
tga
```

<210> SEQ ID NO 22
<211> LENGTH: 272
<212> TYPE: PRT
<213> ORGANISM: Leptospira interrogans serovar copenhageni

<400> SEQUENCE: 22

Met Phe Ser Arg Cys Arg Ile Phe Leu Lys Pro Thr Thr Leu Ile Trp
 1               5                  10                  15

Phe Ala Ile Leu Pro Gly Ala Leu Ser Ala Ser Pro Gln Lys Pro Gly
            20                  25                  30

Thr Phe Glu Leu Leu Gly Gly Tyr Gln Pro Asn Trp Asn Arg Leu Phe
        35                  40                  45

Thr Glu Phe Leu Pro Lys Arg Thr Ala Gln Thr Gly Asn Leu Pro Ser
    50                  55                  60

Ser Gly Val Ile Ser Arg Glu Glu Asp Ile Glu Asn Pro Glu Glu
65                  70                  75                  80

Thr Glu Glu Asp Lys Gln Glu Gly Tyr Gln Asp Asn Arg Lys Thr Glu
                85                  90                  95

Val Gly Val Trp Val Gly Ala Ser Asn Pro Leu Pro Gly Thr Glu Thr
            100                 105                 110

Gln Lys Tyr Leu Asp Thr Thr Leu Gly Gly Phe Phe Arg Ile
        115                 120                 125

Pro Trp Pro Trp Ile Phe Tyr Leu Glu Met Gly Ala Phe Tyr Ala Asn
    130                 135                 140

Tyr Leu Ser Ala Thr Glu Arg Ala Leu Thr Thr Ile Pro Val Tyr Leu
145                 150                 155                 160

Ala Leu Gly Tyr Lys Ile Pro Leu Asp Leu Pro Ile Ser Phe Ile Leu
                165                 170                 175

Arg Ala Gly Gly Gly Glu Ala Phe Val Val Ala Arg Pro Ser Asn Thr
            180                 185                 190

Ser Arg Trp Asp Pro Met Met Ile Val Gly Leu Glu Thr Ser Phe Val
        195                 200                 205

Ala Gly Lys Lys Ile Arg Ile Gly Ile Arg Ile Asp Tyr Asn Lys Ile
    210                 215                 220

Tyr Glu Ser Arg Met Asp Ala Pro Gly Glu Thr Lys Tyr Pro Tyr Thr
225                 230                 235                 240

Ser Pro Tyr Glu Asp Ser Arg Leu Ser Asn Pro Asn Tyr Tyr Arg Val
                245                 250                 255

Val Asp Thr Glu Phe Phe Gln Phe Gly Leu Met Val Ser Val Phe Leu
            260                 265                 270

<210> SEQ ID NO 23
<211> LENGTH: 729
<212> TYPE: DNA
<213> ORGANISM: Leptospira interrogans serovar copenhageni
<220> FEATURE:
<221> NAME/KEY: CDS
<222> LOCATION: (1)...(726)

<400> SEQUENCE: 23

```
atg aat tac aaa ata aga ata tta ttt ctt atc att tta ctt tcg gct     48
Met Asn Tyr Lys Ile Arg Ile Leu Phe Leu Ile Ile Leu Leu Ser Ala
 1               5                  10                  15 ata gca agc tcg atc aca ctc ctg agc cag gaa acg gaa aac gct aaa     96
Ile Ala Ser Ser Ile Thr Leu Leu Ser Gln Glu Thr Glu Asn Ala Lys
            20                  25                  30
```

-continued

```
gta agt ttt tca tta ggt aaa tct tat gtt caa aaa tct ggt aaa agc      144
Val Ser Phe Ser Leu Gly Lys Ser Tyr Val Gln Lys Ser Gly Lys Ser
         35                  40                  45 tcc tgg gaa cct tta aaa cca aac gat ttt ttg gaa gaa gga gat tta      192
Ser Trp Glu Pro Leu Lys Pro Asn Asp Phe Leu Glu Glu Gly Asp Leu
 50                  55                  60 atc tcc acc gga aac ggt tct aga att acg gtt cat tac aaa ggt tcc      240
Ile Ser Thr Gly Asn Gly Ser Arg Ile Thr Val His Tyr Lys Gly Ser
 65                  70                  75                  80 gaa ttt aag att caa caa aac agc aaa gta aaa ctt tca aac ctt cct      288
Glu Phe Lys Ile Gln Gln Asn Ser Lys Val Lys Leu Ser Asn Leu Pro
                 85                  90                  95 gaa aaa tct aaa cga ggt gta tta gaa gta aat caa ggt ttc gca tgg      336
Glu Lys Ser Lys Arg Gly Val Leu Glu Val Asn Gln Gly Phe Ala Trp
            100                 105                 110 ttt aag atc gta aat ctc aaa ggg aaa aaa ttt gaa gtt aca aca cca      384
Phe Lys Ile Val Asn Leu Lys Gly Lys Lys Phe Glu Val Thr Thr Pro
        115                 120                 125 aat tcc acg gcg gga gtc aga ggc act tca ttt tct gct ttc tac gat      432
Asn Ser Thr Ala Gly Val Arg Gly Thr Ser Phe Ser Ala Phe Tyr Asp
130                 135                 140 cct aaa aca aga gaa tcg tct ttt tgc act tgc gaa ggc aag gta tct      480
Pro Lys Thr Arg Glu Ser Ser Phe Cys Thr Cys Glu Gly Lys Val Ser
145                 150                 155                 160 att tcc gat tct aca gga aaa gaa att ctt ttt caa gaa aaa ggc gaa      528
Ile Ser Asp Ser Thr Gly Lys Glu Ile Leu Phe Gln Glu Lys Gly Glu
                165                 170                 175 ggt aca atc gtc tct tca aaa gat ata gaa att aaa aaa ttt gaa tat      576
Gly Thr Ile Val Ser Ser Lys Asp Ile Glu Ile Lys Lys Phe Glu Tyr
            180                 185                 190 aaa gga att att aaa aaa tta aat acc cta tct ggc ttt gaa gag agg      624
Lys Gly Ile Ile Lys Lys Leu Asn Thr Leu Ser Gly Phe Glu Glu Arg
        195                 200                 205 cta aaa aaa aat cct ttt tta aaa aac tgt ctt tct tgt cac act cca      672
Leu Lys Lys Asn Pro Phe Leu Lys Asn Cys Leu Ser Cys His Thr Pro
210                 215                 220 gag ggt tgg att cca caa gaa gaa act ctt aag gac gaa acc tac ggc      720
Glu Gly Trp Ile Pro Gln Glu Glu Thr Leu Lys Asp Glu Thr Tyr Gly
225                 230                 235                 240 aaa caa taa                                                          729
Lys Gln <210> SEQ ID NO 24
<211> LENGTH: 242
<212> TYPE: PRT
<213> ORGANISM: Leptospira interrogans serovar copenhageni

<400> SEQUENCE: 24

Met Asn Tyr Lys Ile Arg Ile Leu Phe Leu Ile Ile Leu Leu Ser Ala
  1               5                  10                  15

Ile Ala Ser Ser Ile Thr Leu Leu Ser Gln Glu Thr Glu Asn Ala Lys
             20                  25                  30

Val Ser Phe Ser Leu Gly Lys Ser Tyr Val Gln Lys Ser Gly Lys Ser
         35                  40                  45

Ser Trp Glu Pro Leu Lys Pro Asn Asp Phe Leu Glu Glu Gly Asp Leu
     50                  55                  60

Ile Ser Thr Gly Asn Gly Ser Arg Ile Thr Val His Tyr Lys Gly Ser
 65                  70                  75                  80
```

```
Glu Phe Lys Ile Gln Gln Asn Ser Lys Val Lys Leu Ser Asn Leu Pro
                 85                  90                  95

Glu Lys Ser Lys Arg Gly Val Leu Glu Val Asn Gln Gly Phe Ala Trp
            100                 105                 110

Phe Lys Ile Val Asn Leu Lys Gly Lys Lys Phe Glu Val Thr Thr Pro
        115                 120                 125

Asn Ser Thr Ala Gly Val Arg Gly Thr Ser Phe Ser Ala Phe Tyr Asp
    130                 135                 140

Pro Lys Thr Arg Glu Ser Ser Phe Cys Thr Cys Glu Gly Lys Val Ser
145                 150                 155                 160

Ile Ser Asp Ser Thr Gly Lys Glu Ile Leu Phe Gln Glu Lys Gly Glu
                165                 170                 175

Gly Thr Ile Val Ser Ser Lys Asp Ile Glu Ile Lys Lys Phe Glu Tyr
            180                 185                 190

Lys Gly Ile Ile Lys Lys Leu Asn Thr Leu Ser Gly Phe Glu Glu Arg
        195                 200                 205

Leu Lys Lys Asn Pro Phe Leu Lys Asn Cys Leu Ser Cys His Thr Pro
    210                 215                 220

Glu Gly Trp Ile Pro Gln Glu Thr Leu Lys Asp Glu Thr Tyr Gly
225                 230                 235                 240

Lys Gln

<210> SEQ ID NO 25
<211> LENGTH: 546
<212> TYPE: DNA
<213> ORGANISM: Leptospira interrogans serovar copenhageni
<220> FEATURE:
<221> NAME/KEY: CDS
<222> LOCATION: (1)...(543)

<400> SEQUENCE: 25 atg aaa att ttt gca ctg agt att tta gtt tta gta gtt tta ctt gta      48
Met Lys Ile Phe Ala Leu Ser Ile Leu Val Leu Val Val Leu Leu Val
  1               5                  10                  15 gcg ttc ttg ttt tat atg ggc gct ttt aat cgg gtt ttg gtt caa gag      96
Ala Phe Leu Phe Tyr Met Gly Ala Phe Asn Arg Val Leu Val Gln Glu
             20                  25                  30 gaa atg aaa gga ccg ttt tac gtt ctt tcg cat gaa agg att gga gat     144
Glu Met Lys Gly Pro Phe Tyr Val Leu Ser His Glu Arg Ile Gly Asp
         35                  40                  45 tat aga aac gtt ggg ctt acg ttt gaa gcc ctt caa aaa gaa ctg cct     192
Tyr Arg Asn Val Gly Leu Thr Phe Glu Ala Leu Gln Lys Glu Leu Pro
     50                  55                  60 gaa aaa gga att cga aat ttt aaa ttg ttc tca ata tat ttg gat aat     240
Glu Lys Gly Ile Arg Asn Phe Lys Leu Phe Ser Ile Tyr Leu Asp Asn
 65                  70                  75                  80 cca aat gag gtt cct aaa gaa aaa cta cga tgt gaa gta gga gct ctt     288
Pro Asn Glu Val Pro Lys Glu Lys Leu Arg Cys Glu Val Gly Ala Leu
                 85                  90                  95 ttt tcg gaa cca tta gaa aaa att cca aat gga ctt tct tta gag tta     336
Phe Ser Glu Pro Leu Glu Lys Ile Pro Asn Gly Leu Ser Leu Glu Leu
            100                 105                 110 aaa ata aga acc att cct tct aaa aaa tat ctt acc gcg gaa ttt cca     384
Lys Ile Arg Thr Ile Pro Ser Lys Lys Tyr Leu Thr Ala Glu Phe Pro
        115                 120                 125 ttg aga aat ttt ctt tct att ttt ctt gga att tat aag gtt tat ccg     432
Leu Arg Asn Phe Leu Ser Ile Phe Leu Gly Ile Tyr Lys Val Tyr Pro
    130                 135                 140
```

-continued

```
aaa ctt ttc aga gcc tgt gaa gaa aga ggt tgt gat ctt aaa gga agg      480
Lys Leu Phe Arg Ala Cys Glu Glu Arg Gly Cys Asp Leu Lys Gly Arg
145                 150                 155                 160 gca tcc att gaa att tat gaa cct ctt acg gaa cat aag act aca tat      528
Ala Ser Ile Glu Ile Tyr Glu Pro Leu Thr Glu His Lys Thr Thr Tyr
                165                 170                 175 ctt ctg cct tta gat tag                                              546
Leu Leu Pro Leu Asp
            180
```

<210> SEQ ID NO 26
<211> LENGTH: 181
<212> TYPE: PRT
<213> ORGANISM: Leptospira interrogans serovar copenhageni

<400> SEQUENCE: 26

```
Met Lys Ile Phe Ala Leu Ser Ile Leu Val Leu Val Val Leu Leu Val
1               5                   10                  15

Ala Phe Leu Phe Tyr Met Gly Ala Phe Asn Arg Val Leu Val Gln Glu
                20                  25                  30

Glu Met Lys Gly Pro Phe Tyr Val Leu Ser His Glu Arg Ile Gly Asp
            35                  40                  45

Tyr Arg Asn Val Gly Leu Thr Phe Glu Ala Leu Gln Lys Glu Leu Pro
        50                  55                  60

Glu Lys Gly Ile Arg Asn Phe Lys Leu Phe Ser Ile Tyr Leu Asp Asn
65                  70                  75                  80

Pro Asn Glu Val Pro Lys Glu Lys Leu Arg Cys Glu Val Gly Ala Leu
                85                  90                  95

Phe Ser Glu Pro Leu Glu Lys Ile Pro Asn Gly Leu Ser Leu Glu Leu
            100                 105                 110

Lys Ile Arg Thr Ile Pro Ser Lys Lys Tyr Leu Thr Ala Glu Phe Pro
        115                 120                 125

Leu Arg Asn Phe Leu Ser Ile Phe Leu Gly Ile Tyr Lys Val Tyr Pro
130                 135                 140

Lys Leu Phe Arg Ala Cys Glu Glu Arg Gly Cys Asp Leu Lys Gly Arg
145                 150                 155                 160

Ala Ser Ile Glu Ile Tyr Glu Pro Leu Thr Glu His Lys Thr Thr Tyr
                165                 170                 175

Leu Leu Pro Leu Asp
            180
```

<210> SEQ ID NO 27
<211> LENGTH: 570
<212> TYPE: DNA
<213> ORGANISM: Leptospira interrogans serovar copenhageni
<220> FEATURE:
<221> NAME/KEY: CDS
<222> LOCATION: (1)...(567)

<400> SEQUENCE: 27

```
atg aag gtt aaa aat atc cgg aaa gga ttt acc ctg atc gag ttg atc       48
Met Lys Val Lys Asn Ile Arg Lys Gly Phe Thr Leu Ile Glu Leu Ile
1               5                   10                  15 gtg gtt atc gcg atc ctc gcg ggg tta att agt att ctt gca agt acc       96
Val Val Ile Ala Ile Leu Ala Gly Leu Ile Ser Ile Leu Ala Ser Thr
                20                  25                  30 gct gca aac ttt atc att cct tcg gga agt gac gcg gca caa act tta      144
Ala Ala Asn Phe Ile Ile Pro Ser Gly Ser Asp Ala Ala Gln Thr Leu
            35                  40                  45
```

```
aaa caa gcc gct gaa ttc tgt tat cga aaa tcc att ctt aca aac acc      192
Lys Gln Ala Ala Glu Phe Cys Tyr Arg Lys Ser Ile Leu Thr Asn Thr
     50                  55                  60 act atg gtt tta gaa ctg gat ata gac aac gat acc tat tct atc aaa      240
Thr Met Val Leu Glu Leu Asp Ile Asp Asn Asp Thr Tyr Ser Ile Lys
 65                  70                  75                  80 aaa tta ctt cga gac gaa agt gga att aaa gaa gtt ttg gtt ttt aaa      288
Lys Leu Leu Arg Asp Glu Ser Gly Ile Lys Glu Val Leu Val Phe Lys
                 85                  90                  95 cct cag aaa ctt cct tat act tcc gaa att ata gat ata act gat att      336
Pro Gln Lys Leu Pro Tyr Thr Ser Glu Ile Ile Asp Ile Thr Asp Ile
             100                 105                 110 aga ggt ttt aga tat acg aaa gga att att aaa gtt ccc tat acc tat      384
Arg Gly Phe Arg Tyr Thr Lys Gly Ile Ile Lys Val Pro Tyr Thr Tyr
         115                 120                 125 ctt ggg atc tcg gca gac tac agt gta cat tta gga agt gat cct tcc      432
Leu Gly Ile Ser Ala Asp Tyr Ser Val His Leu Gly Ser Asp Pro Ser
     130                 135                 140 att tat aga act ttg att ctt tat aga tac ggc gga aag gtt tcc gtt      480
Ile Tyr Arg Thr Leu Ile Leu Tyr Arg Tyr Gly Gly Lys Val Ser Val
145                 150                 155                 160 gtg gaa gga gag cag ttt cat act tct tcg aat ttg gca acc gat aaa      528
Val Glu Gly Glu Gln Phe His Thr Ser Ser Asn Leu Ala Thr Asp Lys
                 165                 170                 175 aat tgg aaa gaa cag gat gat aac gaa caa caa cag cct taa              570
Asn Trp Lys Glu Gln Asp Asp Asn Glu Gln Gln Gln Pro
             180                 185

<210> SEQ ID NO 28
<211> LENGTH: 189
<212> TYPE: PRT
<213> ORGANISM: Leptospira interrogans serovar copenhageni

<400> SEQUENCE: 28

Met Lys Val Lys Asn Ile Arg Lys Gly Phe Thr Leu Ile Glu Leu Ile
 1               5                  10                  15

Val Val Ile Ala Ile Leu Ala Gly Leu Ile Ser Ile Leu Ala Ser Thr
                 20                  25                  30

Ala Ala Asn Phe Ile Ile Pro Ser Gly Ser Asp Ala Ala Gln Thr Leu
             35                  40                  45

Lys Gln Ala Ala Glu Phe Cys Tyr Arg Lys Ser Ile Leu Thr Asn Thr
     50                  55                  60

Thr Met Val Leu Glu Leu Asp Ile Asp Asn Asp Thr Tyr Ser Ile Lys
 65                  70                  75                  80

Lys Leu Leu Arg Asp Glu Ser Gly Ile Lys Glu Val Leu Val Phe Lys
                 85                  90                  95

Pro Gln Lys Leu Pro Tyr Thr Ser Glu Ile Ile Asp Ile Thr Asp Ile
             100                 105                 110

Arg Gly Phe Arg Tyr Thr Lys Gly Ile Ile Lys Val Pro Tyr Thr Tyr
         115                 120                 125

Leu Gly Ile Ser Ala Asp Tyr Ser Val His Leu Gly Ser Asp Pro Ser
     130                 135                 140

Ile Tyr Arg Thr Leu Ile Leu Tyr Arg Tyr Gly Gly Lys Val Ser Val
145                 150                 155                 160

Val Glu Gly Glu Gln Phe His Thr Ser Ser Asn Leu Ala Thr Asp Lys
                 165                 170                 175

Asn Trp Lys Glu Gln Asp Asp Asn Glu Gln Gln Gln Pro
             180                 185
```

<210> SEQ ID NO 29
<211> LENGTH: 441
<212> TYPE: DNA
<213> ORGANISM: Leptospira interrogans serovar copenhageni
<220> FEATURE:
<221> NAME/KEY: CDS
<222> LOCATION: (1)...(438)

<400> SEQUENCE: 29

```
atg aag aat tct ttt cat aaa caa aac cgc aag gaa tcc tgt caa aat      48
Met Lys Asn Ser Phe His Lys Gln Asn Arg Lys Glu Ser Cys Gln Asn
 1               5                  10                  15 agt atg aaa aag tta tta ctc gtt tgt gtt tta gta tgt ttt gtt ggg      96
Ser Met Lys Lys Leu Leu Leu Val Cys Val Leu Val Cys Phe Val Gly
            20                  25                  30 gtt ttt gcc gaa gaa gaa agt ccc gta agg ttc aaa ctg gaa aaa agt     144
Val Phe Ala Glu Glu Glu Ser Pro Val Arg Phe Lys Leu Glu Lys Ser
         35                  40                  45 ttt ggt aat gcg tat att tta aaa att att cat ccg gct aac ttc ggt     192
Phe Gly Asn Ala Tyr Ile Leu Lys Ile Ile His Pro Ala Asn Phe Gly
     50                  55                  60 gtt caa aag gac gct cct cat aaa ata att tta aat cct agg aac gga     240
Val Gln Lys Asp Ala Pro His Lys Ile Ile Leu Asn Pro Arg Asn Gly
 65                  70                  75                  80 gta aag gtt gaa aaa gcg gat ctg aaa gta aaa gga aaa att tca gaa     288
Val Lys Val Glu Lys Ala Asp Leu Lys Val Lys Gly Lys Ile Ser Glu
                 85                  90                  95 aag aaa aaa gaa tat ttt gcc tcg gtg gat ccg att tct ctt gtt gtg     336
Lys Lys Lys Glu Tyr Phe Ala Ser Val Asp Pro Ile Ser Leu Val Val
            100                 105                 110 act ggt aaa gga gaa ttg gag att caa gga aag att tac tac tgt aac     384
Thr Gly Lys Gly Glu Leu Glu Ile Gln Gly Lys Ile Tyr Tyr Cys Asn
        115                 120                 125 ttt gat aaa aat atc tgc att cca ggt aag att cag caa gta gag atc     432
Phe Asp Lys Asn Ile Cys Ile Pro Gly Lys Ile Gln Gln Val Glu Ile
    130                 135                 140 att caa taa                                                          441
Ile Gln
145
```

<210> SEQ ID NO 30
<211> LENGTH: 146
<212> TYPE: PRT
<213> ORGANISM: Leptospira interrogans serovar copenhageni

<400> SEQUENCE: 30

```
Met Lys Asn Ser Phe His Lys Gln Asn Arg Lys Glu Ser Cys Gln Asn
 1               5                  10                  15

Ser Met Lys Lys Leu Leu Leu Val Cys Val Leu Val Cys Phe Val Gly
            20                  25                  30

Val Phe Ala Glu Glu Glu Ser Pro Val Arg Phe Lys Leu Glu Lys Ser
         35                  40                  45

Phe Gly Asn Ala Tyr Ile Leu Lys Ile Ile His Pro Ala Asn Phe Gly
     50                  55                  60

Val Gln Lys Asp Ala Pro His Lys Ile Ile Leu Asn Pro Arg Asn Gly
 65                  70                  75                  80

Val Lys Val Glu Lys Ala Asp Leu Lys Val Lys Gly Lys Ile Ser Glu
                 85                  90                  95

Lys Lys Lys Glu Tyr Phe Ala Ser Val Asp Pro Ile Ser Leu Val Val
```

-continued

```
                100                 105                 110
Thr Gly Lys Gly Glu Leu Glu Ile Gln Gly Lys Ile Tyr Tyr Cys Asn
            115                 120                 125

Phe Asp Lys Asn Ile Cys Ile Pro Gly Lys Ile Gln Gln Val Glu Ile
        130                 135                 140

Ile Gln
145

<210> SEQ ID NO 31
<211> LENGTH: 546
<212> TYPE: DNA
<213> ORGANISM: Leptospira interrogans serovar copenhageni
<220> FEATURE:
<221> NAME/KEY: CDS
<222> LOCATION: (1)...(543)

<400> SEQUENCE: 31 atg aaa cat ttt aac caa ctc gtt ttg tcg ttt ttg att ttt ttt acg        48
Met Lys His Phe Asn Gln Leu Val Leu Ser Phe Leu Ile Phe Phe Thr
  1               5                  10                  15 tct caa agt tac gct tca gag atc ctt aaa aaa gaa atc act ttt tta       96
Ser Gln Ser Tyr Ala Ser Glu Ile Leu Lys Lys Glu Ile Thr Phe Leu
             20                  25                  30 gca att cat cct atg aaa gaa gtt cat gga gct tgt aag gag ata caa      144
Ala Ile His Pro Met Lys Glu Val His Gly Ala Cys Lys Glu Ile Gln
         35                  40                  45 gta gat tct cct caa att caa acg agc gga acc gtt tat aaa ttg aat      192
Val Asp Ser Pro Gln Ile Gln Thr Ser Gly Thr Val Tyr Lys Leu Asn
     50                  55                  60 tct cct ttt aca att aaa att ccg att ttg aaa att cat tcg gga gat      240
Ser Pro Phe Thr Ile Lys Ile Pro Ile Leu Lys Ile His Ser Gly Asp
 65                  70                  75                  80 gaa aac aga gac tct cat atc atg gaa att tta ggt tat cct gat att      288
Glu Asn Arg Asp Ser His Ile Met Glu Ile Leu Gly Tyr Pro Asp Ile
                 85                  90                  95 ccg gaa att ata gtt gtc gta gaa tcc gcc gaa gcc gtt ggt gaa acg      336
Pro Glu Ile Ile Val Val Val Glu Ser Ala Glu Ala Val Gly Glu Thr
            100                 105                 110 tat tta att cgt ggt aaa ctt tcg att cac gga ttt act cgc gac ttt      384
Tyr Leu Ile Arg Gly Lys Leu Ser Ile His Gly Phe Thr Arg Asp Phe
        115                 120                 125 caa tct tct gga aaa gtt gag cca aat ggg gtg ggt cag att cgt ata      432
Gln Ser Ser Gly Lys Val Glu Pro Asn Gly Val Gly Gln Ile Arg Ile
    130                 135                 140 ttt gga aaa gtg aat att caa ttt tcc gat ttt aat ctc gaa aga ccc      480
Phe Gly Lys Val Asn Ile Gln Phe Ser Asp Phe Asn Leu Glu Arg Pro
145                 150                 155                 160 tct ctt tta ttt ata aaa aca aaa gaa gaa att gaa att gga tat gat      528
Ser Leu Leu Phe Ile Lys Thr Lys Glu Glu Ile Glu Ile Gly Tyr Asp
                165                 170                 175 ttt tta att aag ata taa                                              546
Phe Leu Ile Lys Ile
            180

<210> SEQ ID NO 32
<211> LENGTH: 181
<212> TYPE: PRT
<213> ORGANISM: Leptospira interrogans serovar copenhageni

<400> SEQUENCE: 32

Met Lys His Phe Asn Gln Leu Val Leu Ser Phe Leu Ile Phe Phe Thr
```

-continued

```
                1               5                  10                 15
Ser Gln Ser Tyr Ala Ser Glu Ile Leu Lys Lys Glu Ile Thr Phe Leu
                    20                  25                 30

Ala Ile His Pro Met Lys Glu Val His Gly Ala Cys Lys Glu Ile Gln
            35                  40                  45

Val Asp Ser Pro Gln Ile Gln Thr Ser Gly Thr Val Tyr Lys Leu Asn
        50                  55                  60

Ser Pro Phe Thr Ile Lys Ile Pro Ile Leu Lys Ile His Ser Gly Asp
65                  70                  75                  80

Glu Asn Arg Asp Ser His Ile Met Glu Ile Leu Gly Tyr Pro Asp Ile
                85                  90                  95

Pro Glu Ile Ile Val Val Val Glu Ser Ala Glu Ala Val Gly Glu Thr
            100                 105                 110

Tyr Leu Ile Arg Gly Lys Leu Ser Ile His Gly Phe Thr Arg Asp Phe
        115                 120                 125

Gln Ser Ser Gly Lys Val Glu Pro Asn Gly Val Gly Gln Ile Arg Ile
    130                 135                 140

Phe Gly Lys Val Asn Ile Gln Phe Ser Asp Phe Asn Leu Glu Arg Pro
145                 150                 155                 160

Ser Leu Leu Phe Ile Lys Thr Lys Glu Glu Ile Glu Ile Gly Tyr Asp
                165                 170                 175

Phe Leu Ile Lys Ile
            180

<210> SEQ ID NO 33
<211> LENGTH: 588
<212> TYPE: DNA
<213> ORGANISM: Leptospira interrogans serovar copenhageni
<220> FEATURE:
<221> NAME/KEY: CDS
<222> LOCATION: (1)...(585)

<400> SEQUENCE: 33 atg gtc aaa aag att ttg aat ctg att ctg ctc ggt gca att gca ttt      48
Met Val Lys Lys Ile Leu Asn Leu Ile Leu Leu Gly Ala Ile Ala Phe
1               5                  10                  15 tca ttc act ctc tgc tcc tct gct gaa aaa aaa gag gaa tcc gca gct      96
Ser Phe Thr Leu Cys Ser Ser Ala Glu Lys Lys Glu Glu Ser Ala Ala
            20                  25                  30 cct gag cct tca acg caa gag caa tcc gca gct gca aac aga aat gtt     144
Pro Glu Pro Ser Thr Gln Glu Gln Ser Ala Ala Ala Asn Arg Asn Val
        35                  40                  45 gac gtc aat tct ccg gaa gcg atc gca gat tct tta aac gaa aaa cta     192
Asp Val Asn Ser Pro Glu Ala Ile Ala Asp Ser Leu Asn Glu Lys Leu
    50                  55                  60 aaa gat ttc cga tat cca gac ggt tta act cgt cct gga ttt agt tat     240
Lys Asp Phe Arg Tyr Pro Asp Gly Leu Thr Arg Pro Gly Phe Ser Tyr
65                  70                  75                  80 aaa aaa gcg gat gtt acc cct ggt gat ttc agc gag tgg tct aaa aca     288
Lys Lys Ala Asp Val Thr Pro Gly Asp Phe Ser Glu Trp Ser Lys Thr
                85                  90                  95 aac gct cct gta atc aaa gaa ggt ctt gga aaa ctt cca gat agt tac     336
Asn Ala Pro Val Ile Lys Glu Gly Leu Gly Lys Leu Pro Asp Ser Tyr
            100                 105                 110 gct ctt gaa att aca gga cac acc gat gcg atc ggt ccc gaa caa gca     384
Ala Leu Glu Ile Thr Gly His Thr Asp Ala Ile Gly Pro Glu Gln Ala
        115                 120                 125 gaa ggt gct aaa aaa gga aat att ttt tac tct gag ctt cgt gca aat     432
Glu Gly Ala Lys Lys Gly Asn Ile Phe Tyr Ser Glu Leu Arg Ala Asn
```

```
               Glu Gly Ala Lys Lys Gly Asn Ile Phe Tyr Ser Glu Leu Arg Ala Asn
                   130                 135                 140 gca gtt aaa caa gct tta atc aaa caa ggg att cca gca aat cgt atc        480
Ala Val Lys Gln Ala Leu Ile Lys Gln Gly Ile Pro Ala Asn Arg Ile
145                 150                 155                 160 gtt act aaa ggt gcc ggt tct tcc gag cca gtt tct ggt ctt gat gcg        528
Val Thr Lys Gly Ala Gly Ser Ser Glu Pro Val Ser Gly Leu Asp Ala
                165                 170                 175 aaa gat gct aaa aat aga aga gtc act ttc cgt ttt gcg act tcc gca        576
Lys Asp Ala Lys Asn Arg Arg Val Thr Phe Arg Phe Ala Thr Ser Ala
            180                 185                 190 cca caa caa taa                                                         588
Pro Gln Gln
        195
```

<210> SEQ ID NO 34
<211> LENGTH: 195
<212> TYPE: PRT
<213> ORGANISM: Leptospira interrogans serovar copenhageni

<400> SEQUENCE: 34

```
Met Val Lys Lys Ile Leu Asn Leu Ile Leu Leu Gly Ala Ile Ala Phe
  1               5                  10                  15

Ser Phe Thr Leu Cys Ser Ser Ala Glu Lys Lys Glu Glu Ser Ala Ala
                 20                  25                  30

Pro Glu Pro Ser Thr Gln Glu Gln Ser Ala Ala Ala Asn Arg Asn Val
             35                  40                  45

Asp Val Asn Ser Pro Glu Ala Ile Ala Asp Ser Leu Asn Glu Lys Leu
         50                  55                  60

Lys Asp Phe Arg Tyr Pro Asp Gly Leu Thr Arg Pro Gly Phe Ser Tyr
 65                  70                  75                  80

Lys Lys Ala Asp Val Thr Pro Gly Asp Phe Ser Glu Trp Ser Lys Thr
                 85                  90                  95

Asn Ala Pro Val Ile Lys Glu Gly Leu Gly Lys Leu Pro Asp Ser Tyr
            100                 105                 110

Ala Leu Glu Ile Thr Gly His Thr Asp Ala Ile Gly Pro Glu Gln Ala
        115                 120                 125

Glu Gly Ala Lys Lys Gly Asn Ile Phe Tyr Ser Glu Leu Arg Ala Asn
    130                 135                 140

Ala Val Lys Gln Ala Leu Ile Lys Gln Gly Ile Pro Ala Asn Arg Ile
145                 150                 155                 160

Val Thr Lys Gly Ala Gly Ser Ser Glu Pro Val Ser Gly Leu Asp Ala
                165                 170                 175

Lys Asp Ala Lys Asn Arg Arg Val Thr Phe Arg Phe Ala Thr Ser Ala
            180                 185                 190

Pro Gln Gln
        195
```

<210> SEQ ID NO 35
<211> LENGTH: 1674
<212> TYPE: DNA
<213> ORGANISM: Leptospira interrogans serovar copenhageni
<220> FEATURE:
<221> NAME/KEY: CDS
<222> LOCATION: (1)...(1671)

<400> SEQUENCE: 35

```
atg tat tac aaa aag aaa agg aca tta gaa aaa ttt ctc gtt ttc gga         48
Met Tyr Tyr Lys Lys Lys Arg Thr Leu Glu Lys Phe Leu Val Phe Gly
```

-continued

```
        1               5               10              15
acc att cta ctc acg atg att cag cct act tgg agt gag gac ata ctt    96
Thr Ile Leu Leu Thr Met Ile Gln Pro Thr Trp Ser Glu Asp Ile Leu
                 20              25              30 ccg gaa gaa act gtt tta gaa gag aat aaa aaa tct ccc gtt gaa aat    144
Pro Glu Glu Thr Val Leu Glu Glu Asn Lys Lys Ser Pro Val Glu Asn
         35              40              45 tta ggt gac tcc aaa aaa ata ttg aga ctg act tta aaa gac gca gtc    192
Leu Gly Asp Ser Lys Lys Ile Leu Arg Leu Thr Leu Lys Asp Ala Val
         50              55              60 aat tat gtt ctt gaa aag aat att aca atc caa aac gct aaa atg gaa    240
Asn Tyr Val Leu Glu Lys Asn Ile Thr Ile Gln Asn Ala Lys Met Glu
 65              70              75              80 tat gta aaa gcg gac ggt gga gaa ctt aaa aac gaa tcc caa ttt act    288
Tyr Val Lys Ala Asp Gly Gly Glu Leu Lys Asn Glu Ser Gln Phe Thr
                 85              90              95 tgg aat cta atc ggt gga att acc gtt ttc agg aca act ctc cct gcc    336
Trp Asn Leu Ile Gly Gly Ile Thr Val Phe Arg Thr Thr Leu Pro Ala
                 100             105             110 aat aga aat aac atc ttt gcc gga acc aaa caa agc caa gat aaa tta    384
Asn Arg Asn Asn Ile Phe Ala Gly Thr Lys Gln Ser Gln Asp Lys Leu
         115             120             125 agc gtc gga att gag aaa aat ttt aga act gga acg tat gca aaa tta    432
Ser Val Gly Ile Glu Lys Asn Phe Arg Thr Gly Thr Tyr Ala Lys Leu
         130             135             140 gaa gca agt act act cgt ttt gat acg agc gct ttc gaa aac ccg tcc    480
Glu Ala Ser Thr Thr Arg Phe Asp Thr Ser Ala Phe Glu Asn Pro Ser
145             150             155             160 aca act cct tcc aac tta gcg gcg ctt gca att cct cct tta tat aca    528
Thr Thr Pro Ser Asn Leu Ala Ala Leu Ala Ile Pro Pro Leu Tyr Thr
                 165             170             175 ggc gct ttg acc atc act tta agc cag gaa atc tta aag tat agt ttt    576
Gly Ala Leu Thr Ile Thr Leu Ser Gln Glu Ile Leu Lys Tyr Ser Phe
                 180             185             190 gga aaa act cag aaa gaa aga gaa gcc att tta aga caa aat act gta    624
Gly Lys Thr Gln Lys Glu Arg Glu Ala Ile Leu Arg Gln Asn Thr Val
         195             200             205 atc aaa aga gaa gaa ttg att tat gta ctt tcg cag ctt gta gca caa    672
Ile Lys Arg Glu Glu Leu Ile Tyr Val Leu Ser Gln Leu Val Ala Gln
 210             215             220 aca ttg att caa tat tgg agt tta aat atc tac gac tcg aac gta aaa    720
Thr Leu Ile Gln Tyr Trp Ser Leu Asn Ile Tyr Asp Ser Asn Val Lys
225             230             235             240 acg ctg caa gat tta gaa tcc aat act aga aac atc aga gat ttg acc    768
Thr Leu Gln Asp Leu Glu Ser Asn Thr Arg Asn Ile Arg Asp Leu Thr
                 245             250             255 gtt aga aaa cga aac tta ggg ctt tcg gaa ggt ttt gaa gtc aat cta    816
Val Arg Lys Arg Asn Leu Gly Leu Ser Glu Gly Phe Glu Val Asn Leu
         260             265             270 tgg aat tct att ctt tct caa aca gca ggt aat tta gaa aaa gct aaa    864
Trp Asn Ser Ile Leu Ser Gln Thr Ala Gly Asn Leu Glu Lys Ala Lys
         275             280             285 gtg tct cgt aaa gaa gca gaa aga aat tta att cgg att tta aac gcg    912
Val Ser Arg Lys Glu Ala Glu Arg Asn Leu Ile Arg Ile Leu Asn Ala
 290             295             300 gat cct tct tct aaa atc gaa ggt gtt act gat ctt caa gaa aac gtt    960
Asp Pro Ser Ser Lys Ile Glu Gly Val Thr Asp Leu Gln Glu Asn Val
305             310             315             320 cct tta gat ttt aac gtg gaa aag gat tat atc tac gca ctt gat cat    1008
```

```
                    Pro Leu Asp Phe Asn Val Glu Lys Asp Tyr Ile Tyr Ala Leu Asp His
                                    325                 330                 335 aga acc gat cta aaa aat ctt cgc aaa caa agg gaa atc gca gaa tta          1056
Arg Thr Asp Leu Lys Asn Leu Arg Lys Gln Arg Glu Ile Ala Glu Leu
            340                 345                 350 aat ctt aag atc aaa gaa gca gaa gac atg cct tct tta aaa ctt tca          1104
Asn Leu Lys Ile Lys Glu Ala Glu Asp Met Pro Ser Leu Lys Leu Ser
            355                 360                 365 ggg gcc tat tct aca aga gga caa aat att gtt tct cct caa caa aat          1152
Gly Ala Tyr Ser Thr Arg Gly Gln Asn Ile Val Ser Pro Gln Gln Asn
    370                 375                 380 ctc acg gat gga aat aga gga gtc gcc tct ttt aaa tat ccg gaa gca          1200
Leu Thr Asp Gly Asn Arg Gly Val Ala Ser Phe Lys Tyr Pro Glu Ala
385                 390                 395                 400 tac gcg gct ttt caa ttt tct tat cct ctt tgg gat aaa ggg atc aag          1248
Tyr Ala Ala Phe Gln Phe Ser Tyr Pro Leu Trp Asp Lys Gly Ile Lys
                405                 410                 415 gca gat att cga aac gca aaa tta gac gta cag aat cta gaa aaa aaa          1296
Ala Asp Ile Arg Asn Ala Lys Leu Asp Val Gln Asn Leu Glu Lys Lys
            420                 425                 430 gaa gct gag tta aaa ctt tcc atc aaa gaa gaa tta gaa aat cgt tat          1344
Glu Ala Glu Leu Lys Leu Ser Ile Lys Glu Glu Leu Glu Asn Arg Tyr
            435                 440                 445 gct gcc atc gtt gcc gat aaa gat att ttc gaa ggt gct aaa aaa aga          1392
Ala Ala Ile Val Ala Asp Lys Asp Ile Phe Glu Gly Ala Lys Lys Arg
    450                 455                 460 aag gaa gaa gca aat aaa ttc tac aaa ggt ctt tcc gaa cgt ttt cgt          1440
Lys Glu Glu Ala Asn Lys Phe Tyr Lys Gly Leu Ser Glu Arg Phe Arg
465                 470                 475                 480 cag gga aga ttt acc gcg gtc gcg gtt aaa aac gcc tta gac aac gta          1488
Gln Gly Arg Phe Thr Ala Val Ala Val Lys Asn Ala Leu Asp Asn Val
                485                 490                 495 att caa tct gaa tta caa gtt acc cag gca aaa att caa ctg aac ata          1536
Ile Gln Ser Glu Leu Gln Val Thr Gln Ala Lys Ile Gln Leu Asn Ile
            500                 505                 510 gac att ctt cgt tat gaa ttg gca aaa aat cat atc ttc gaa agg ttc          1584
Asp Ile Leu Arg Tyr Glu Leu Ala Lys Asn His Ile Phe Glu Arg Phe
            515                 520                 525 ggc gtg aac gta aat gac atc atc gat cga ctg atg aag atg gtg gat          1632
Gly Val Asn Val Asn Asp Ile Ile Asp Arg Leu Met Lys Met Val Asp
    530                 535                 540 att gca caa tcc aaa tct tct acg gaa act tcc gaa aaa taa               1674
Ile Ala Gln Ser Lys Ser Ser Thr Glu Thr Ser Glu Lys
545                 550                 555

<210> SEQ ID NO 36
<211> LENGTH: 557
<212> TYPE: PRT
<213> ORGANISM: Leptospira interrogans serovar copenhageni

<400> SEQUENCE: 36

Met Tyr Tyr Lys Lys Lys Arg Thr Leu Glu Lys Phe Leu Val Phe Gly
1               5                   10                  15

Thr Ile Leu Leu Thr Met Ile Gln Pro Thr Trp Ser Glu Asp Ile Leu
            20                  25                  30

Pro Glu Glu Thr Val Leu Glu Gly Asn Lys Lys Ser Pro Val Glu Asn
        35                  40                  45

Leu Gly Asp Ser Lys Lys Ile Leu Arg Leu Thr Leu Lys Asp Ala Val
    50                  55                  60
```

```
Asn Tyr Val Leu Glu Lys Asn Ile Thr Ile Gln Asn Ala Lys Met Glu
 65                  70                  75                  80

Tyr Val Lys Ala Asp Gly Gly Glu Leu Lys Asn Glu Ser Gln Phe Thr
                 85                  90                  95

Trp Asn Leu Ile Gly Gly Ile Thr Val Phe Arg Thr Thr Leu Pro Ala
            100                 105                 110

Asn Arg Asn Asn Ile Phe Ala Gly Thr Lys Gln Ser Gln Asp Lys Leu
            115                 120                 125

Ser Val Gly Ile Glu Lys Asn Phe Arg Thr Gly Thr Tyr Ala Lys Leu
130                 135                 140

Glu Ala Ser Thr Thr Arg Phe Asp Thr Ser Ala Phe Glu Asn Pro Ser
145                 150                 155                 160

Thr Thr Pro Ser Asn Leu Ala Ala Leu Ala Ile Pro Pro Leu Tyr Thr
                165                 170                 175

Gly Ala Leu Thr Ile Thr Leu Ser Gln Glu Ile Leu Lys Tyr Ser Phe
            180                 185                 190

Gly Lys Thr Gln Lys Glu Arg Glu Ala Ile Leu Arg Gln Asn Thr Val
        195                 200                 205

Ile Lys Arg Glu Glu Leu Ile Tyr Val Leu Ser Gln Leu Val Ala Gln
210                 215                 220

Thr Leu Ile Gln Tyr Trp Ser Leu Asn Ile Tyr Asp Ser Asn Val Lys
225                 230                 235                 240

Thr Leu Gln Asp Leu Glu Ser Asn Thr Arg Asn Ile Arg Asp Leu Thr
                245                 250                 255

Val Arg Lys Arg Asn Leu Gly Leu Ser Glu Gly Phe Glu Val Asn Leu
            260                 265                 270

Trp Asn Ser Ile Leu Ser Gln Thr Ala Gly Asn Leu Glu Lys Ala Lys
        275                 280                 285

Val Ser Arg Lys Glu Ala Glu Arg Asn Leu Ile Arg Ile Leu Asn Ala
290                 295                 300

Asp Pro Ser Ser Lys Ile Glu Gly Val Thr Asp Leu Gln Glu Asn Val
305                 310                 315                 320

Pro Leu Asp Phe Asn Val Glu Lys Asp Tyr Ile Tyr Ala Leu Asp His
                325                 330                 335

Arg Thr Asp Leu Lys Asn Leu Arg Lys Gln Arg Glu Ile Ala Glu Leu
            340                 345                 350

Asn Leu Lys Ile Lys Glu Ala Glu Asp Met Pro Ser Leu Lys Leu Ser
        355                 360                 365

Gly Ala Tyr Ser Thr Arg Gly Gln Asn Ile Val Ser Pro Gln Gln Asn
370                 375                 380

Leu Thr Asp Gly Asn Arg Gly Val Ala Ser Phe Lys Tyr Pro Glu Ala
385                 390                 395                 400

Tyr Ala Ala Phe Gln Phe Ser Tyr Pro Leu Trp Asp Lys Gly Ile Lys
                405                 410                 415

Ala Asp Ile Arg Asn Ala Lys Leu Asp Val Gln Asn Leu Glu Lys Lys
            420                 425                 430

Glu Ala Glu Leu Lys Leu Ser Ile Lys Glu Glu Leu Glu Asn Arg Tyr
        435                 440                 445

Ala Ala Ile Val Ala Asp Lys Asp Ile Phe Gly Ala Lys Lys Arg
450                 455                 460

Lys Glu Glu Ala Asn Lys Phe Tyr Lys Gly Leu Ser Glu Arg Phe Arg
465                 470                 475                 480

Gln Gly Arg Phe Thr Ala Val Ala Val Lys Asn Ala Leu Asp Asn Val
```

```
                    485                 490                 495
Ile Gln Ser Glu Leu Gln Val Thr Gln Ala Lys Ile Gln Leu Asn Ile
            500                 505                 510

Asp Ile Leu Arg Tyr Glu Leu Ala Lys Asn His Ile Phe Glu Arg Phe
            515                 520                 525

Gly Val Asn Val Asn Asp Ile Ile Asp Arg Leu Met Lys Met Val Asp
            530                 535                 540

Ile Ala Gln Ser Lys Ser Ser Thr Glu Thr Ser Glu Lys
545                 550                 555

<210> SEQ ID NO 37
<211> LENGTH: 480
<212> TYPE: DNA
<213> ORGANISM: Leptospira interrogans serovar copenhageni
<220> FEATURE:
<221> NAME/KEY: CDS
<222> LOCATION: (1)...(477)

<400> SEQUENCE: 37 ttg atc ggt tta agt att gcg att ttg att cga tcc ttt ctt ttt ttt    48
Leu Ile Gly Leu Ser Ile Ala Ile Leu Ile Arg Ser Phe Leu Phe Phe
  1               5                  10                  15 cca ttt acg ttg gaa acc aaa gac atg ctt cct act tat tcc cct gga    96
Pro Phe Thr Leu Glu Thr Lys Asp Met Leu Pro Thr Tyr Ser Pro Gly
             20                  25                  30 aaa aga att tat ttc cat agg ttt gta aat cgt tcc aat ctc tat ctt   144
Lys Arg Ile Tyr Phe His Arg Phe Val Asn Arg Ser Asn Leu Tyr Leu
         35                  40                  45 gga gat tta gtt tta gtc aaa cat cca act caa gaa ggt aag gta gtt   192
Gly Asp Leu Val Leu Val Lys His Pro Thr Gln Glu Gly Lys Val Val
     50                  55                  60 ttt tcc agg atc tcc gga aaa cca gga gac aca gtt caa atg aaa aat   240
Phe Ser Arg Ile Ser Gly Lys Pro Gly Asp Thr Val Gln Met Lys Asn
 65                  70                  75                  80 aag atc ttg tat cgt aat aat cat cca gaa gat att tct ggt gtt ggg   288
Lys Ile Leu Tyr Arg Asn Asn His Pro Glu Asp Ile Ser Gly Val Gly
                 85                  90                  95 agt ggc ttt aca ctt cag ttc gaa gat aaa cga gga gca ttt ccc tcc   336
Ser Gly Phe Thr Leu Gln Phe Glu Asp Lys Arg Gly Ala Phe Pro Ser
            100                 105                 110 agt ttt tct ggc aga gac aac gga gaa cct ttg att ctt aaa gac cga   384
Ser Phe Ser Gly Arg Asp Asn Gly Glu Pro Leu Ile Leu Lys Asp Arg
        115                 120                 125 gat tat ttt ctt ctc tgc gac aac cga gat tct tgc tcc gac tcc aga   432
Asp Tyr Phe Leu Leu Cys Asp Asn Arg Asp Ser Cys Ser Asp Ser Arg
    130                 135                 140 gat ttt ggt cca att cct ata gaa aac ata tta gga aaa gcg ttc taa   480
Asp Phe Gly Pro Ile Pro Ile Glu Asn Ile Leu Gly Lys Ala Phe
145                 150                 155

<210> SEQ ID NO 38
<211> LENGTH: 159
<212> TYPE: PRT
<213> ORGANISM: Leptospira interrogans serovar copenhageni

<400> SEQUENCE: 38

Leu Ile Gly Leu Ser Ile Ala Ile Leu Ile Arg Ser Phe Leu Phe Phe
  1               5                  10                  15

Pro Phe Thr Leu Glu Thr Lys Asp Met Leu Pro Thr Tyr Ser Pro Gly
             20                  25                  30
```

```
Lys Arg Ile Tyr Phe His Arg Phe Val Asn Arg Ser Asn Leu Tyr Leu
            35                  40                  45

Gly Asp Leu Val Leu Val Lys His Pro Thr Gln Glu Gly Lys Val Val
 50                  55                  60

Phe Ser Arg Ile Ser Gly Lys Pro Gly Asp Thr Val Gln Met Lys Asn
 65                  70                  75                  80

Lys Ile Leu Tyr Arg Asn Asn His Pro Glu Asp Ile Ser Gly Val Gly
                 85                  90                  95

Ser Gly Phe Thr Leu Gln Phe Glu Asp Lys Arg Gly Ala Phe Pro Ser
                100                 105                 110

Ser Phe Ser Gly Arg Asp Asn Gly Glu Pro Leu Ile Leu Lys Asp Arg
            115                 120                 125

Asp Tyr Phe Leu Leu Cys Asp Asn Arg Asp Ser Cys Ser Asp Ser Arg
130                 135                 140

Asp Phe Gly Pro Ile Pro Ile Glu Asn Ile Leu Gly Lys Ala Phe
145                 150                 155

<210> SEQ ID NO 39
<211> LENGTH: 966
<212> TYPE: DNA
<213> ORGANISM: Leptospira interrogans serovar copenhageni
<220> FEATURE:
<221> NAME/KEY: CDS
<222> LOCATION: (1)...(963)

<400> SEQUENCE: 39 atg gtt ttt tcc aga tca acc gat ttg ttt aaa gga atc aat agg acc      48
Met Val Phe Ser Arg Ser Thr Asp Leu Phe Lys Gly Ile Asn Arg Thr
 1               5                  10                  15 gag gaa act atg aaa caa ata gca atc tta acc gcc ctg atc att ttt      96
Glu Glu Thr Met Lys Gln Ile Ala Ile Leu Thr Ala Leu Ile Ile Phe
                20                  25                  30 acg tct tgt gcg tcg gta gag tct aaa cga agc gtc agc gct tct gga     144
Thr Ser Cys Ala Ser Val Glu Ser Lys Arg Ser Val Ser Ala Ser Gly
            35                  40                  45 gat ccg tcg gag att ttt ttt gaa aaa gaa att att ccg atg gat tct     192
Asp Pro Ser Glu Ile Phe Phe Glu Lys Glu Ile Ile Pro Met Asp Ser
 50                  55                  60 aat tca aat ttc gtt tct caa aaa cct gca cgt aga tct ttc gaa gaa     240
Asn Ser Asn Phe Val Ser Gln Lys Pro Ala Arg Arg Ser Phe Glu Glu
 65                  70                  75                  80 gaa ttg agt gtt gaa aag tat gca aaa gct caa cca cct gaa aaa acc     288
Glu Leu Ser Val Glu Lys Tyr Ala Lys Ala Gln Pro Pro Glu Lys Thr
                85                  90                  95 aat tct tct gga gat ttt gac gaa gtt gga atg tct tcc tgg tat ggc     336
Asn Ser Ser Gly Asp Phe Asp Glu Val Gly Met Ser Ser Trp Tyr Gly
                100                 105                 110 gca aag ttt cac ggt aaa cca acg gca agc gga gaa aaa ttt gat aaa     384
Ala Lys Phe His Gly Lys Pro Thr Ala Ser Gly Glu Lys Phe Asp Lys
            115                 120                 125 aca aaa cta act gct gca cat cca aca ctt cct tta ggt tcc atc att     432
Thr Lys Leu Thr Ala Ala His Pro Thr Leu Pro Leu Gly Ser Ile Ile
130                 135                 140 aga gtt caa aat tta gaa aac caa aaa gaa gtt ata gtt cgt gtc aac     480
Arg Val Gln Asn Leu Glu Asn Gln Lys Glu Val Ile Val Arg Val Asn
145                 150                 155                 160 gat aga gga cct ttt gta aag gat aga atc att gat ctt tct gaa aaa     528
Asp Arg Gly Pro Phe Val Lys Asp Arg Ile Ile Asp Leu Ser Glu Lys
                165                 170                 175
```

```
gct gca gat act tta gat ttt aaa gat gta ggt att gct aaa gta ggt      576
Ala Ala Asp Thr Leu Asp Phe Lys Asp Val Gly Ile Ala Lys Val Gly
            180                 185                 190 att aaa gta gta aaa cgt gga gga gct gca aac gaa gaa tcc gaa gat      624
Ile Lys Val Val Lys Arg Gly Gly Ala Ala Asn Glu Glu Ser Glu Asp
        195                 200                 205 ctc gaa aat tct gac gat gaa gaa gct ctt tta gaa gat gga aaa cct      672
Leu Glu Asn Ser Asp Asp Glu Glu Ala Leu Leu Glu Asp Gly Lys Pro
    210                 215                 220 gaa aaa cta aat cct caa aaa tcg gat tat caa aac aaa ccg att gcc      720
Glu Lys Leu Asn Pro Gln Lys Ser Asp Tyr Gln Asn Lys Pro Ile Ala
225                 230                 235                 240 ggt gga aag tat atc aaa ggt gct cct aaa gga tat acg gtt caa gta      768
Gly Gly Lys Tyr Ile Lys Gly Ala Pro Lys Gly Tyr Thr Val Gln Val
                245                 250                 255 ggt gtt ttt cgg gaa caa tct aga gct gaa tct tat aaa tct aat ctt      816
Gly Val Phe Arg Glu Gln Ser Arg Ala Glu Ser Tyr Lys Ser Asn Leu
            260                 265                 270 gga caa gaa tac ggt gaa aaa act ttc cta ttt aca aga gat ggt tta      864
Gly Gln Glu Tyr Gly Glu Lys Thr Phe Leu Phe Thr Arg Asp Gly Leu
        275                 280                 285 ttt gta att cag tta ggg gat ttc gca agc aga act gag gcg gaa tcg      912
Phe Val Ile Gln Leu Gly Asp Phe Ala Ser Arg Thr Glu Ala Glu Ser
    290                 295                 300 ttg aaa tcg aaa tta aaa aac gat gga att gac tgt ttc att ccg aaa      960
Leu Lys Ser Lys Leu Lys Asn Asp Gly Ile Asp Cys Phe Ile Pro Lys
305                 310                 315                 320 aaa taa                                                              966
Lys

<210> SEQ ID NO 40
<211> LENGTH: 321
<212> TYPE: PRT
<213> ORGANISM: Leptospira interrogans serovar copenhageni

<400> SEQUENCE: 40

```
Ala Ala Asp Thr Leu Asp Phe Lys Asp Val Gly Ile Ala Lys Val Gly
            180                 185                 190

Ile Lys Val Val Lys Arg Gly Gly Ala Ala Asn Glu Glu Ser Glu Asp
        195                 200                 205

Leu Glu Asn Ser Asp Asp Glu Glu Ala Leu Leu Glu Asp Gly Lys Pro
    210                 215                 220

Glu Lys Leu Asn Pro Gln Lys Ser Asp Tyr Gln Asn Lys Pro Ile Ala
225                 230                 235                 240

Gly Gly Lys Tyr Ile Lys Gly Ala Pro Lys Gly Tyr Thr Val Gln Val
                245                 250                 255

Gly Val Phe Arg Glu Gln Ser Arg Ala Glu Ser Tyr Lys Ser Asn Leu
            260                 265                 270

Gly Gln Glu Tyr Gly Glu Lys Thr Phe Leu Phe Thr Arg Asp Gly Leu
        275                 280                 285

Phe Val Ile Gln Leu Gly Asp Phe Ala Ser Arg Thr Glu Ala Glu Ser
    290                 295                 300

Leu Lys Ser Lys Leu Lys Asn Asp Gly Ile Asp Cys Phe Ile Pro Lys
305                 310                 315                 320

Lys

<210> SEQ ID NO 41
<211> LENGTH: 1053
<212> TYPE: DNA
<213> ORGANISM: Leptospira interrogans serovar copenhageni
<220> FEATURE:
<221> NAME/KEY: CDS
<222> LOCATION: (1)...(1050)

<400> SEQUENCE: 41 atg gaa cct aat tca gat tca aat cga agg tca aat atg gaa cga gca      48
Met Glu Pro Asn Ser Asp Ser Asn Arg Arg Ser Asn Met Glu Arg Ala
  1               5                  10                  15 att tca aac gaa atg aca cgg cta gaa ctc agt gaa ttt tta tcg gat      96
Ile Ser Asn Glu Met Thr Arg Leu Glu Leu Ser Glu Phe Leu Ser Asp
             20                  25                  30 cca aga tct aga aaa gaa ttt ttt gag ttg atg aaa tta aag aat aaa     144
Pro Arg Ser Arg Lys Glu Phe Phe Glu Leu Met Lys Leu Lys Asn Lys
         35                  40                  45 atc gga cat tta gaa atg aat cta aag tta gga tcc gat gaa aac aaa     192
Ile Gly His Leu Glu Met Asn Leu Lys Leu Gly Ser Asp Glu Asn Lys
     50                  55                  60 agt aga act ttc tat att aga aat tca tta tta gct gct gct tgt gtt     240
Ser Arg Thr Phe Tyr Ile Arg Asn Ser Leu Leu Ala Ala Ala Cys Val
 65                  70                  75                  80 ctt ttg ctt tca gct cta gct ttt tat ttc aga ttt ttt tct tcg gaa     288
Leu Leu Leu Ser Ala Leu Ala Phe Tyr Phe Arg Phe Phe Ser Ser Glu
                 85                  90                  95 caa aac gaa ttt gaa att aca aaa tca gta act act ggt cag tgt aat     336
Gln Asn Glu Phe Glu Ile Thr Lys Ser Val Thr Thr Gly Gln Cys Asn
            100                 105                 110 gtt tct att aat aaa gaa aac att att ctg aaa tcg ggt aag gat tct     384
Val Ser Ile Asn Lys Glu Asn Ile Ile Leu Lys Ser Gly Lys Asp Ser
        115                 120                 125 tat tgt gat tat aca att tcg gga gaa tta gga cta acg ttg agg att     432
Tyr Cys Asp Tyr Thr Ile Ser Gly Glu Leu Gly Leu Thr Leu Arg Ile
    130                 135                 140 tta cca gaa tcc att ttt tca gct tct aaa aaa gga gat gaa gta aat     480
Leu Pro Glu Ser Ile Phe Ser Ala Ser Lys Lys Gly Asp Glu Val Asn
```

-continued

```
                145                 150                 155                 160
cta agt tta agt tcc gga aaa gtt tta ttc act acg aac aaa aaa aaa       528
Leu Ser Leu Ser Ser Gly Lys Val Leu Phe Thr Thr Asn Lys Lys Lys
                165                 170                 175 ata tct tta aaa att cgg tcg aaa gta gat act tta tct tcc gaa ctt       576
Ile Ser Leu Lys Ile Arg Ser Lys Val Asp Thr Leu Ser Ser Glu Leu
            180                 185                 190 ttg gga aca act ctc gtt ttg atc gca gat caa cat tct aaa aaa tat       624
Leu Gly Thr Thr Leu Val Leu Ile Ala Asp Gln His Ser Lys Lys Tyr
        195                 200                 205 caa att atg gtt ttg gaa gga gct ata cga gtc gat tct aca aaa tca       672
Gln Ile Met Val Leu Glu Gly Ala Ile Arg Val Asp Ser Thr Lys Ser
    210                 215                 220 aaa atg gat att tta cct ggt tat tcg gtt ttg aag gat gga tct tct       720
Lys Met Asp Ile Leu Pro Gly Tyr Ser Val Leu Lys Asp Gly Ser Ser
225                 230                 235                 240 gaa agt tct act caa tcc tct ggg caa gaa gtc gag gtt atg aaa att       768
Glu Ser Ser Thr Gln Ser Ser Gly Gln Glu Val Glu Val Met Lys Ile
                245                 250                 255 gag cca aaa gaa ttt aca aaa tac caa gcg ctt tcg gag aat tct aaa       816
Glu Pro Lys Glu Phe Thr Lys Tyr Gln Ala Leu Ser Glu Asn Ser Lys
            260                 265                 270 aag gtc tta aat gaa aac ttt act cat cac aat cgg gaa acg gat ttt       864
Lys Val Leu Asn Glu Asn Phe Thr His His Asn Arg Glu Thr Asp Phe
        275                 280                 285 tta atc aaa tcc gaa ata gaa gag aat tcg tat cct ata tat cgt atc       912
Leu Ile Lys Ser Glu Ile Glu Glu Asn Ser Tyr Pro Ile Tyr Arg Ile
    290                 295                 300 act ctt aaa aac aaa caa gtt gtt tct gga acg atc gaa gag act gaa       960
Thr Leu Lys Asn Lys Gln Val Val Ser Gly Thr Ile Glu Glu Thr Glu
305                 310                 315                 320 aaa ttt tat cta ctt aaa gat aaa gat ggg aat atc aaa gaa att gaa      1008
Lys Phe Tyr Leu Leu Lys Asp Lys Asp Gly Asn Ile Lys Glu Ile Glu
                325                 330                 335 aaa gag gat ata atc gaa tta gaa ctt gtt caa cca aag aac taa         1053
Lys Glu Asp Ile Ile Glu Leu Glu Leu Val Gln Pro Lys Asn
            340                 345                 350

<210> SEQ ID NO 42
<211> LENGTH: 350
<212> TYPE: PRT
<213> ORGANISM: Leptospira interrogans serovar copenhageni

<400> SEQUENCE: 42

Met Glu Pro Asn Ser Asp Ser Asn Arg Arg Ser Asn Met Glu Arg Ala
  1               5                  10                  15

Ile Ser Asn Glu Met Thr Arg Leu Glu Leu Ser Glu Phe Leu Ser Asp
                 20                  25                  30

Pro Arg Ser Arg Lys Glu Phe Phe Glu Leu Met Lys Leu Lys Asn Lys
             35                  40                  45

Ile Gly His Leu Glu Met Asn Leu Lys Leu Gly Ser Asp Glu Asn Lys
         50                  55                  60

Ser Arg Thr Phe Tyr Ile Arg Asn Ser Leu Leu Ala Ala Ala Cys Val
 65                  70                  75                  80

Leu Leu Leu Ser Ala Leu Ala Phe Tyr Phe Arg Phe Phe Ser Ser Glu
                 85                  90                  95

Gln Asn Glu Phe Glu Ile Thr Lys Ser Val Thr Thr Gly Gln Cys Asn
            100                 105                 110
```

```
Val Ser Ile Asn Lys Glu Asn Ile Ile Leu Lys Ser Gly Lys Asp Ser
        115                 120                 125

Tyr Cys Asp Tyr Thr Ile Ser Gly Glu Leu Gly Leu Thr Leu Arg Ile
130                 135                 140

Leu Pro Glu Ser Ile Phe Ser Ala Ser Lys Lys Gly Asp Glu Val Asn
145                 150                 155                 160

Leu Ser Leu Ser Ser Gly Lys Val Leu Phe Thr Thr Asn Lys Lys Lys
                165                 170                 175

Ile Ser Leu Lys Ile Arg Ser Lys Val Asp Thr Leu Ser Ser Glu Leu
            180                 185                 190

Leu Gly Thr Thr Leu Val Leu Ile Ala Asp Gln His Ser Lys Lys Tyr
        195                 200                 205

Gln Ile Met Val Leu Glu Gly Ala Ile Arg Val Asp Ser Thr Lys Ser
    210                 215                 220

Lys Met Asp Ile Leu Pro Gly Tyr Ser Val Leu Lys Asp Gly Ser Ser
225                 230                 235                 240

Glu Ser Ser Thr Gln Ser Ser Gly Gln Glu Val Val Met Lys Ile
                245                 250                 255

Glu Pro Lys Glu Phe Thr Lys Tyr Gln Ala Leu Ser Glu Asn Ser Lys
            260                 265                 270

Lys Val Leu Asn Glu Asn Phe Thr His His Asn Arg Glu Thr Asp Phe
        275                 280                 285

Leu Ile Lys Ser Glu Ile Glu Glu Asn Ser Tyr Pro Ile Tyr Arg Ile
    290                 295                 300

Thr Leu Lys Asn Lys Gln Val Val Ser Gly Thr Ile Glu Glu Thr Glu
305                 310                 315                 320

Lys Phe Tyr Leu Leu Lys Asp Lys Asp Gly Asn Ile Lys Glu Ile Glu
                325                 330                 335

Lys Glu Asp Ile Ile Glu Leu Glu Leu Val Gln Pro Lys Asn
            340                 345                 350

<210> SEQ ID NO 43
<211> LENGTH: 1074
<212> TYPE: DNA
<213> ORGANISM: Leptospira interrogans serovar copenhageni
<220> FEATURE:
<221> NAME/KEY: CDS
<222> LOCATION: (1)...(1071)

<400> SEQUENCE: 43 ttg ttt tta aaa aaa agg aaa gcg gtt tgt aaa gtt ttg tgt cct ttg      48
Leu Phe Leu Lys Lys Arg Lys Ala Val Cys Lys Val Leu Cys Pro Leu
  1               5                  10                  15 aat tcg ctt gaa gcg aat gat agg ttg tcg aat tct tac ctt atg gaa      96
Asn Ser Leu Glu Ala Asn Asp Arg Leu Ser Asn Ser Tyr Leu Met Glu
             20                  25                  30 aaa gaa aca ctg gaa gac tta gag ttt gcc agg atc aaa ctg gaa act     144
Lys Glu Thr Leu Glu Asp Leu Glu Phe Ala Arg Ile Lys Leu Glu Thr
         35                  40                  45 ctc aaa caa gaa ctg gga aaa gaa att aca gga caa gac gaa gtt att     192
Leu Lys Gln Glu Leu Gly Lys Glu Ile Thr Gly Gln Asp Glu Val Ile
     50                  55                  60 cga aac gta ttg gtt tgt ctg atc tgt caa ggt cat gta ctt tta gaa     240
Arg Asn Val Leu Val Cys Leu Ile Cys Gln Gly His Val Leu Leu Glu
 65                  70                  75                  80 ggg atg ccc ggg ctt gca aaa aca cta ctt gca agg tca ctt gca agt     288
Gly Met Pro Gly Leu Ala Lys Thr Leu Leu Ala Arg Ser Leu Ala Ser
                 85                  90                  95
```

```
gcg ctg gat tta aac ttt aaa aga att caa ttt aca cct gat ctt tta       336
Ala Leu Asp Leu Asn Phe Lys Arg Ile Gln Phe Thr Pro Asp Leu Leu
        100                 105                 110 cca gcc gat ctc gtc gga aca gta gta ttt aat cca aaa acc aca gaa       384
Pro Ala Asp Leu Val Gly Thr Val Val Phe Asn Pro Lys Thr Thr Glu
            115                 120                 125 ttt gaa act aga aag gga cca gtg ttt acc gga gtt tta ctc gcg gac       432
Phe Glu Thr Arg Lys Gly Pro Val Phe Thr Gly Val Leu Leu Ala Asp
        130                 135                 140 gaa att aat aga gct ccg gct aag gtt cag tct gct ctt cta gaa agt       480
Glu Ile Asn Arg Ala Pro Ala Lys Val Gln Ser Ala Leu Leu Glu Ser
145                 150                 155                 160 atg gaa gaa aag acc gtt acg att gga gac aaa acc tat aaa cta gac       528
Met Glu Glu Lys Thr Val Thr Ile Gly Asp Lys Thr Tyr Lys Leu Asp
                165                 170                 175 aaa ccg ttt tta gta atc gca act caa aat cca atc gat cag gac gga       576
Lys Pro Phe Leu Val Ile Ala Thr Gln Asn Pro Ile Asp Gln Asp Gly
            180                 185                 190 act tat cct ctt ccc gaa gct cag atg gac cga ttt ttg atg aag atc       624
Thr Tyr Pro Leu Pro Glu Ala Gln Met Asp Arg Phe Leu Met Lys Ile
        195                 200                 205 aac gta gat tac cca act ttg gaa gag gaa gtt tcc att ttg gat caa       672
Asn Val Asp Tyr Pro Thr Leu Glu Glu Glu Val Ser Ile Leu Asp Gln
210                 215                 220 cac gga aaa ata agt tcg gca aac gga aag att aaa aaa acc gtt tct       720
His Gly Lys Ile Ser Ser Ala Asn Gly Lys Ile Lys Lys Thr Val Ser
225                 230                 235                 240 tcc tct gaa att tta cga cta tct tct atg ctc gac gaa gta ttt atc       768
Ser Ser Glu Ile Leu Arg Leu Ser Ser Met Leu Asp Glu Val Phe Ile
                245                 250                 255 gaa gaa aaa atc aaa tcc tat att gta cga ttg gtt cga aat aca aga       816
Glu Glu Lys Ile Lys Ser Tyr Ile Val Arg Leu Val Arg Asn Thr Arg
            260                 265                 270 cca gaa gaa aga acc att ccg gaa ctc att ccg tat atc cga cac gga       864
Pro Glu Glu Arg Thr Ile Pro Glu Leu Ile Pro Tyr Ile Arg His Gly
        275                 280                 285 gct tct ccg aga gct tct tta agt ata tta aaa agt tct aaa gca aat       912
Ala Ser Pro Arg Ala Ser Leu Ser Ile Leu Lys Ser Ser Lys Ala Asn
    290                 295                 300 gct ctt ttg agt ggt agg aca tac gta act ccg gaa gac gta aaa acg       960
Ala Leu Leu Ser Gly Arg Thr Tyr Val Thr Pro Glu Asp Val Lys Thr
305                 310                 315                 320 tct ctt gtg gaa ata tta aga cat aga ata ctg ctt acc ttt gag gca      1008
Ser Leu Val Glu Ile Leu Arg His Arg Ile Leu Leu Thr Phe Glu Ala
                325                 330                 335 att tcg gaa gaa ttg aac gta gaa tct ttg atc cga act gtt gtg gag      1056
Ile Ser Glu Glu Leu Asn Val Glu Ser Leu Ile Arg Thr Val Val Glu
            340                 345                 350 gca act ccg gtt cct tag                                              1074
Ala Thr Pro Val Pro
        355

<210> SEQ ID NO 44
<211> LENGTH: 357
<212> TYPE: PRT
<213> ORGANISM: Leptospira interrogans serovar copenhageni

<400> SEQUENCE: 44

Leu Phe Leu Lys Lys Arg Lys Ala Val Cys Lys Val Leu Cys Pro Leu
 1               5                  10                  15
```

```
Asn Ser Leu Glu Ala Asn Asp Arg Leu Ser Asn Ser Tyr Leu Met Glu
             20                  25                  30

Lys Glu Thr Leu Glu Asp Leu Glu Phe Ala Arg Ile Lys Leu Glu Thr
         35                  40                  45

Leu Lys Gln Glu Leu Gly Lys Glu Ile Thr Gly Gln Asp Glu Val Ile
     50                  55                  60

Arg Asn Val Leu Val Cys Leu Ile Cys Gln Gly His Val Leu Leu Glu
 65                  70                  75                  80

Gly Met Pro Gly Leu Ala Lys Thr Leu Leu Ala Arg Ser Leu Ala Ser
             85                  90                  95

Ala Leu Asp Leu Asn Phe Lys Arg Ile Gln Phe Thr Pro Asp Leu Leu
            100                 105                 110

Pro Ala Asp Leu Val Gly Thr Val Phe Asn Pro Lys Thr Thr Glu
            115                 120                 125

Phe Glu Thr Arg Lys Gly Pro Val Phe Thr Gly Val Leu Leu Ala Asp
        130                 135                 140

Glu Ile Asn Arg Ala Pro Ala Lys Val Gln Ser Ala Leu Leu Glu Ser
145                 150                 155                 160

Met Glu Glu Lys Thr Val Thr Ile Gly Asp Lys Thr Tyr Lys Leu Asp
                165                 170                 175

Lys Pro Phe Leu Val Ile Ala Thr Gln Asn Pro Ile Asp Gln Asp Gly
            180                 185                 190

Thr Tyr Pro Leu Pro Glu Ala Gln Met Asp Arg Phe Leu Met Lys Ile
        195                 200                 205

Asn Val Asp Tyr Pro Thr Leu Glu Glu Glu Val Ser Ile Leu Asp Gln
    210                 215                 220

His Gly Lys Ile Ser Ser Ala Asn Gly Lys Ile Lys Lys Thr Val Ser
225                 230                 235                 240

Ser Ser Glu Ile Leu Arg Leu Ser Ser Met Leu Asp Glu Val Phe Ile
                245                 250                 255

Glu Glu Lys Ile Lys Ser Tyr Ile Val Arg Leu Val Arg Asn Thr Arg
            260                 265                 270

Pro Glu Glu Arg Thr Ile Pro Glu Leu Ile Pro Tyr Ile Arg His Gly
        275                 280                 285

Ala Ser Pro Arg Ala Ser Leu Ser Ile Leu Lys Ser Ser Lys Ala Asn
    290                 295                 300

Ala Leu Leu Ser Gly Arg Thr Tyr Val Thr Pro Glu Asp Val Lys Thr
305                 310                 315                 320

Ser Leu Val Glu Ile Leu Arg His Arg Ile Leu Leu Thr Phe Glu Ala
                325                 330                 335

Ile Ser Glu Glu Leu Asn Val Glu Ser Leu Ile Arg Thr Val Val Glu
            340                 345                 350

Ala Thr Pro Val Pro
        355

<210> SEQ ID NO 45
<211> LENGTH: 480
<212> TYPE: DNA
<213> ORGANISM: Leptospira interrogans serovar copenhageni
<220> FEATURE:
<221> NAME/KEY: CDS
<222> LOCATION: (1)...(477)

<400> SEQUENCE: 45 atg aaa aaa cat tct atc agt aaa atc att ata act gct tgt tgc att        48
```

```
                Met Lys Lys His Ser Ile Ser Lys Ile Ile Ile Thr Ala Cys Cys Ile
                 1               5                  10

We claim:

1. An isolated Leptospiral protein consisting of the amino acid sequence set forth in SEQ ID NO: 32.

2. Immunogenic composition comprising the isolated Leptospiral protein of claim 1, and a pharmaceutically acceptable carrier.

3. An isolated antibody which specifically binds to the Leptospiral protein of claim 1.

4. The isolated antibody of claim 3, wherein the antibody is a monoclonal antibody.

5. Hybridoma cell line which produces the isolated monoclonal antibody of claim 4.

* * * * *